United States Patent
Harvengt et al.

(10) Patent No.: US 12,016,919 B2
(45) Date of Patent: Jun. 25, 2024

(54) METHODS FOR MANUFACTURING AN ADJUVANT

(71) Applicant: GLAXOSMITHKLINE BIOLOGICALS S.A., Rixensart (BE)

(72) Inventors: Pol Harvengt, Rixensart (BE); Philippe Jehoulet, Rixensart (BE); Loic Le Gourrierec, Rixensart (BE); Demostene Sifakakis, Rixensart (BE); Laurent Strodiot, Rixensart (BE)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 957 days.

(21) Appl. No.: 16/616,999

(22) PCT Filed: Mar. 23, 2018

(86) PCT No.: PCT/EP2018/057488
§ 371 (c)(1),
(2) Date: Nov. 26, 2019

(87) PCT Pub. No.: WO2018/219521
PCT Pub. Date: Dec. 6, 2018

(65) Prior Publication Data
US 2021/0162042 A1   Jun. 3, 2021

Related U.S. Application Data

(60) Provisional application No. 62/512,352, filed on May 30, 2017.

(51) Int. Cl.
*A61K 39/00* (2006.01)
*A61K 39/39* (2006.01)
(Continued)

(52) U.S. Cl.
CPC .......... *A61K 39/39* (2013.01); *B01F 23/4105* (2022.01); *B01F 25/4334* (2022.01);
(Continued)

(58) Field of Classification Search
CPC ...................................................... A61K 39/39
See application file for complete search history.

(56) References Cited

U.S. PATENT DOCUMENTS 9,198,645 B2   12/2015  Jahn
2002/0097633 A1*  7/2002  O'Connor .......... B01D 17/0208
366/341

(Continued)

FOREIGN PATENT DOCUMENTS

CN   102133186 A   7/2011
CN   102302453 A   1/2012
(Continued)

OTHER PUBLICATIONS

Kastner et al., "High-throughput manufacturing of size-tuned liposomes by a new microfluidics method using enhanced tools for characterization," International Journal of Pharmaceutics, vol. 477, 2015, pp. 361-368.
(Continued)

*Primary Examiner* — Anshu Bhatia
(74) *Attorney, Agent, or Firm* — Birch, Stewart, Kolasch & Birch, LLP

(57) ABSTRACT

The present invention relates to compositions and methods for manufacturing an adjuvant comprising a saponin using a microfluidic device and to aspects thereof.

19 Claims, 35 Drawing Sheets
Specification includes a Sequence Listing.

(51) Int. Cl.
  *B01F 23/41* (2022.01)
  *B01F 25/433* (2022.01)
  *B01F 33/301* (2022.01)
  *B01F 101/22* (2022.01)

(52) U.S. Cl.
  CPC ............. *B01F 33/3017* (2022.01); *A61K 2039/55555* (2013.01); *A61K 2039/55572* (2013.01); *A61K 2039/55577* (2013.01); *B01F 23/4143* (2022.01); *B01F 2101/22* (2022.01); *B01F 2215/0431* (2013.01); *B01F 2215/044* (2013.01); *B01F 2215/045* (2013.01)

(56) References Cited

U.S. PATENT DOCUMENTS

| | | |
|---|---|---|
| 2010/0022007 A1 | 1/2010 | Kenis et al. |
| 2011/0212167 A1* | 9/2011 | Ali .................. A61K 8/4953 514/275 |
| 2013/0202684 A1 | 8/2013 | Geall et al. |
| 2015/0110854 A1* | 4/2015 | Shaw .................. A61K 39/39 514/25 |
| 2016/0051954 A1 | 2/2016 | Brujic et al. |
| 2016/0214103 A1 | 7/2016 | Cullis et al. |
| 2016/0276209 A1 | 9/2016 | Usenko |

FOREIGN PATENT DOCUMENTS

| | | |
|---|---|---|
| WO | 98/15287 A1 | 4/1998 |
| WO | 00/07621 A2 | 2/2000 |
| WO | 2007/062831 A1 | 6/2007 |
| WO | 2010/142686 A1 | 12/2010 |
| WO | WO 2012/030901 A1 | 3/2012 |
| WO | 2013/041572 A1 | 3/2013 |

OTHER PUBLICATIONS

Perrie et al., "Designing liposomal adjuvants for the next generation of vaccines," Advanced Drug Delivery Reviews, vol. 99, 2016, pp. 85-96.
Perrie et al., "Microfluidics production of liposomes—from low solubility drugs to vaccines," Nanomedicines: Materials, Manufacturing and Therapeutic Applications, Jul. 16, 2016, 42 pages total.
Yu et al., "Microfluidic Methods for Production of Liposomes," Methods in Enzymology, vol. 465, 2009, pp. 129-141.

* cited by examiner

FIG 8

| Day | DOPC concentration (ug/ml) | Flow rate ratio | Temperature (°C) | Total flow rate (ml/min) | Comment |
|---|---|---|---|---|---|
| 1 | 100 | 4 | 15 | 14 | |
| 1 | 100 | 4 | 25 | 20 | |
| 1 | 130 | 4 | 20 | 17 | |
| 1 | 130 | 5 | 15 | 17 | |
| 1 | 130 | 5 | 20 | 17 | Pt centre |
| 1 | 160 | 5 | 20 | 17 | |
| 1 | 160 | 6 | 15 | 14 | |
| 1 | 160 | 6 | 15 | 20 | |
| 1 | 160 | 6 | 25 | 20 | Day1 |
| 2 | 100 | 4 | 15 | 14 | RepeatDay2 |
| 2 | 100 | 5 | 20 | 17 | |
| 2 | 100 | 6 | 25 | 14 | |
| 2 | 100 | 6 | 25 | 20 | |
| 2 | 130 | 5 | 20 | 17 | Pt centre |
| 2 | 130 | 5 | 20 | 17 | Pt centre |
| 2 | 160 | 4 | 15 | 20 | |
| 2 | 160 | 4 | 25 | 14 | |
| 2 | 160 | 6 | 25 | 20 | RepeatDay2 |
| 3 | 100 | 4 | 15 | 14 | RepeatDay3 |
| 3 | 100 | 4 | 15 | 20 | |
| 3 | 100 | 4 | 25 | 14 | |
| 3 | 100 | 6 | 15 | 14 | |
| 3 | 130 | 5 | 20 | 17 | Pt centre |
| 3 | 130 | 5 | 20 | 17 | Pt centre |
| 3 | 130 | 6 | 20 | 17 | |
| 3 | 160 | 6 | 25 | 14 | |
| 3 | 160 | 6 | 25 | 20 | RepeatDay3 |
| 4 | 100 | 4 | 15 | 14 | RepeatDay4 |
| 4 | 100 | 6 | 15 | 20 | |
| 4 | 130 | 5 | 20 | 14 | |
| 4 | 130 | 5 | 20 | 17 | Pt centre |
| 4 | 130 | 5 | 20 | 20 | |
| 4 | 130 | 5 | 25 | 17 | |
| 4 | 160 | 4 | 15 | 14 | |
| 4 | 160 | 4 | 25 | 20 | |
| 4 | 160 | 6 | 25 | 20 | RepeatDay4 |

FIG 10

| Day | Concentration mg/ml | Ratio | Temp °C | Flow rate ml/min | Reynolds number | QS21 in aqueous phase mg/ml | Zav nm | PdI |
|---|---|---|---|---|---|---|---|---|
| 1 | 100 | 4 | 25 | 20 | 171 | 1.67 | 159.2 | 0.302 |
| 1 | 160 | 6 | 25 | 20 | 198 | 1.60 | 141.1 | 0.297 |
| 1 | 130 | 4 | 20 | 17 | 137 | 2.17 | 116.6 | 0.225 |
| 1 | 130 | 5 | 20 | 17 | 148 | 1.63 | 97.09 | 0.200 |
| 1 | 160 | 5 | 20 | 17 | 148 | 2.00 | 120.6 | 0.229 |
| 1 | 100 | 4 | 15 | 14 | 104 | 1.67 | 114.6 | 0.248 |
| 1 | 130 | 5 | 15 | 17 | 136 | 1.63 | 94.41 | 0.167 |
| 1 | 160 | 6 | 15 | 14 | 118 | 1.60 | 110.8 | 0.213 |
| 1 | 160 | 6 | 15 | 20 | 169 | 1.60 | 100.1 | 0.166 |
| 2 | 100 | 6 | 25 | 14 | 139 | 1.00 | 115.2 | 0.21 |
| 2 | 100 | 6 | 25 | 20 | 198 | 1.00 | 123.5 | 0.237 |
| 2 | 160 | 4 | 25 | 14 | 120 | 2.67 | 128.1 | 0.162 |
| 2 | 160 | 6 | 25 | 20 | 198 | 1.60 | 127.5 | 0.204 |
| 2 | 100 | 5 | 20 | 17 | 148 | 1.25 | 87.42 | 0.157 |
| 2 | 130 | 5 | 20 | 17 | 148 | 1.63 | 95.35 | 0.158 |
| 2 | 130 | 5 | 20 | 17 | 148 | 1.63 | 95.36 | 0.167 |
| 2 | 100 | 4 | 15 | 14 | 104 | 1.67 | 103 | 0.183 |
| 2 | 160 | 4 | 15 | 20 | 149 | 2.67 | 107.7 | 0.187 |
| 3 | 100 | 4 | 25 | 14 | 120 | 1.67 | 131.6 | 0.2 |
| 3 | 160 | 6 | 25 | 14 | 139 | 1.60 | 115.7 | 0.178 |
| 3 | 160 | 6 | 25 | 20 | 198 | 1.60 | 132.6 | 0.24 |
| 3 | 130 | 5 | 20 | 17 | 148 | 1.63 | 96.19 | 0.169 |
| 3 | 130 | 5 | 20 | 17 | 148 | 1.63 | 98.51 | 0.183 |
| 3 | 130 | 6 | 20 | 17 | 157 | 1.30 | 97.39 | 0.171 |
| 3 | 100 | 4 | 15 | 14 | 104 | 1.67 | 97.85 | 0.182 |
| 3 | 100 | 6 | 15 | 14 | 118 | 1.00 | 98.3 | 0.189 |
| 3 | 100 | 4 | 15 | 20 | 149 | 1.67 | 88.89 | 0.186 |
| 4 | 130 | 5 | 25 | 17 | 158 | 1.63 | 105 | 0.16 |
| 4 | 160 | 4 | 25 | 20 | 171 | 2.67 | 134 | 0.183 |
| 4 | 160 | 6 | 25 | 20 | 198 | 1.60 | 127.3 | 0.194 |
| 4 | 130 | 5 | 20 | 14 | 122 | 1.63 | 110.7 | 0.159 |
| 4 | 130 | 5 | 20 | 17 | 148 | 1.63 | 96.91 | 0.154 |
| 4 | 130 | 5 | 20 | 20 | 174 | 1.63 | 100.2 | 0.168 |
| 4 | 100 | 4 | 15 | 14 | 104 | 1.67 | 103.9 | 0.194 |
| 4 | 100 | 6 | 15 | 20 | 169 | 1.00 | 77.07 | 0.177 |
| 4 | 160 | 4 | 15 | 14 | 104 | 2.67 | 115.5 | 0.191 |

SEQUENCE LISTING

<160> NUMBER OF SEQ ID NOS: 9

<210> SEQ ID NO 1
<211> LENGTH: 424
<212> TYPE: PRT
<213> ORGANISM: Artificial

<220> FEATURE:
<223> OTHER INFORMATION: RTS

<400> SEQUENCE: 1

```
Met Met Ala Pro Asp Pro Asn Ala Asn Pro Asn Ala Asn Pro Asn Ala
1               5                   10                  15

Asn Pro Asn Ala Asn Pro Asn Ala Asn Pro Asn Ala Asn Pro Asn Ala
            20                  25                  30

Asn Pro Asn Ala Asn Pro Asn Ala Asn Pro Asn Ala Asn Pro Asn Ala
        35                  40                  45

Asn Pro Asn Ala Asn Pro Asn Ala Asn Pro Asn Ala Asn Pro Asn Ala
    50                  55                  60

Asn Pro Asn Ala Asn Pro Asn Ala Asn Pro Asn Ala Asn Pro Asn Lys
65                  70                  75                  80

Asn Asn Gln Gly Asn Gly Gln Gly His Asn Met Pro Asn Asp Pro Asn
                85                  90                  95

Arg Asn Val Asp Glu Asn Ala Asn Ala Asn Ser Ala Val Lys Asn Asn
            100                 105                 110

Asn Asn Glu Glu Pro Ser Asp Lys His Ile Lys Glu Tyr Leu Asn Lys
        115                 120                 125

Ile Gln Asn Ser Leu Ser Thr Glu Trp Ser Pro Cys Ser Val Thr Cys
    130                 135                 140

Gly Asn Gly Ile Gln Val Arg Ile Lys Pro Gly Ser Ala Asn Lys Pro
145                 150                 155                 160

Lys Asp Glu Leu Asp Tyr Ala Asn Asp Ile Glu Lys Lys Ile Cys Lys
                165                 170                 175

Met Glu Lys Cys Ser Ser Val Phe Asn Val Val Asn Ser Ser Ile Gly
            180                 185                 190

Leu Gly Pro Val Thr Asn Met Glu Asn Ile Thr Ser Gly Phe Leu Gly
        195                 200                 205

Pro Leu Leu Val Leu Gln Ala Gly Phe Phe Leu Leu Thr Arg Ile Leu
    210                 215                 220

Thr Ile Pro Gln Ser Leu Asp Ser Trp Trp Thr Ser Leu Asn Phe Leu
225                 230                 235                 240

Gly Gly Ser Pro Val Cys Leu Gly Gln Asn Ser Gln Ser Pro Thr Ser
                245                 250                 255

Asn His Ser Pro Thr Ser Cys Pro Pro Ile Cys Pro Gly Tyr Arg Trp
            260                 265                 270

Met Cys Leu Arg Arg Phe Ile Ile Phe Leu Phe Ile Leu Leu Leu Cys
        275                 280                 285

Leu Ile Phe Leu Leu Val Leu Leu Asp Tyr Gln Gly Met Leu Pro Val
    290                 295                 300

Cys Pro Leu Ile Pro Gly Ser Thr Thr Thr Asn Thr Gly Pro Cys Lys
305                 310                 315                 320

Thr Cys Thr Thr Pro Ala Gln Gly Asn Ser Met Phe Pro Ser Cys Cys
                325                 330                 335

Cys Thr Lys Pro Thr Asp Gly Asn Cys Thr Cys Ile Pro Ile Pro Ser
            340                 345                 350

Ser Trp Ala Phe Ala Lys Tyr Leu Trp Glu Trp Ala Ser Val Arg Phe
        355                 360                 365

Ser Trp Leu Ser Leu Leu Val Pro Phe Val Gln Trp Phe Val Gly Leu
    370                 375                 380

Ser Pro Thr Val Trp Leu Ser Ala Ile Trp Met Met Trp Tyr Trp Gly
385                 390                 395                 400
```

Pro Ser Leu Tyr Ser Ile Val Ser Pro Phe Ile Pro Leu Leu Pro Ile
            405                 410                 415

Phe Phe Cys Leu Trp Val Tyr Ile
            420

<210> SEQ ID NO 2
<211> LENGTH: 391
<212> TYPE: PRT
<213> ORGANISM: Mycobacterium tuberculosis

<400> SEQUENCE: 2

Met Val Asp Phe Gly Ala Leu Pro Pro Glu Ile Asn Ser Ala Arg Met
1               5                   10                  15

Tyr Ala Gly Pro Gly Ser Ala Ser Leu Val Ala Ala Gln Met Trp
            20                  25                  30

Asp Ser Val Ala Ser Asp Leu Phe Ser Ala Ala Ser Ala Phe Gln Ser
            35                  40                  45

Val Val Trp Gly Leu Thr Val Gly Ser Trp Ile Gly Ser Ser Ala Gly
        50                  55                  60

Leu Met Val Ala Ala Ser Pro Tyr Val Ala Trp Met Ser Val Thr
65                  70                  75                  80

Ala Gly Gln Ala Glu Leu Thr Ala Ala Gln Val Arg Val Ala Ala Ala
                85                  90                  95

Ala Tyr Glu Thr Ala Tyr Gly Leu Thr Val Pro Pro Val Ile Ala
            100                 105                 110

Glu Asn Arg Ala Glu Leu Met Ile Leu Ile Ala Thr Asn Leu Leu Gly
            115                 120                 125

Gln Asn Thr Pro Ala Ile Ala Val Asn Glu Ala Glu Tyr Gly Glu Met
        130                 135                 140

Trp Ala Gln Asp Ala Ala Ala Met Phe Gly Tyr Ala Ala Ala Thr Ala
145                 150                 155                 160

Thr Ala Thr Ala Thr Leu Leu Pro Phe Glu Glu Ala Pro Glu Met Thr
                165                 170                 175

Ser Ala Gly Gly Leu Leu Glu Gln Ala Ala Val Glu Glu Ala Ser
            180                 185                 190

Asp Thr Ala Ala Ala Asn Gln Leu Met Asn Asn Val Pro Gln Ala Leu
            195                 200                 205

Gln Gln Leu Ala Gln Pro Thr Gln Gly Thr Thr Pro Ser Ser Lys Leu
        210                 215                 220

Gly Gly Leu Trp Lys Thr Val Ser Pro His Arg Ser Pro Ile Ser Asn
225                 230                 235                 240

Met Val Ser Met Ala Asn Asn His Met Ser Met Thr Asn Ser Gly Val
                245                 250                 255

Ser Met Thr Asn Thr Leu Ser Ser Met Leu Lys Gly Phe Ala Pro Ala
            260                 265                 270

Ala Ala Ala Gln Ala Val Gln Thr Ala Gln Asn Gly Val Arg Ala
            275                 280                 285

Met Ser Ser Leu Gly Ser Ser Leu Gly Ser Ser Gly Leu Gly Gly Gly
        290                 295                 300

Val Ala Ala Asn Leu Gly Arg Ala Ala Ser Val Gly Ser Leu Ser Val
305                 310                 315                 320

Pro Gln Ala Trp Ala Ala Ala Asn Gln Ala Val Thr Pro Ala Ala Arg
                325                 330                 335

Ala Leu Pro Leu Thr Ser Leu Thr Ser Ala Ala Glu Arg Gly Pro Gly

```
                    340              345              350
Gln Met Leu Gly Gly Leu Pro Val Gly Gln Met Gly Ala Arg Ala Gly
            355              360              365

Gly Gly Leu Ser Gly Val Leu Arg Val Pro Pro Arg Pro Tyr Val Met
            370              375              380

Pro His Ser Pro Ala Ala Gly
385             390

<210> SEQ ID NO 3
<211> LENGTH: 323
<212> TYPE: PRT
<213> ORGANISM: Mycobacterium tuberculosis

<400> SEQUENCE: 3

Ala Pro Pro Ala Leu Ser Gln Asp Arg Phe Ala Asp Phe Pro Ala Leu
1               5                   10                  15

Pro Leu Asp Pro Ser Ala Met Val Ala Gln Val Gly Pro Gln Val Val
            20                  25                  30

Asn Ile Asn Thr Lys Leu Gly Tyr Asn Asn Ala Val Gly Ala Gly Thr
        35                  40                  45

Gly Ile Val Ile Asp Pro Asn Gly Val Val Leu Thr Asn Asn His Val
    50                  55                  60

Ile Ala Gly Ala Thr Asp Ile Asn Ala Phe Ser Val Gly Ser Gly Gln
65                  70                  75                  80

Thr Tyr Gly Val Asp Val Val Gly Tyr Asp Arg Thr Gln Asp Val Ala
                85                  90                  95

Val Leu Gln Leu Arg Gly Ala Gly Gly Leu Pro Ser Ala Ala Ile Gly
            100                 105                 110

Gly Gly Val Ala Val Gly Glu Pro Val Val Ala Met Gly Asn Ser Gly
        115                 120                 125

Gly Gln Gly Gly Thr Pro Arg Ala Val Pro Gly Arg Val Val Ala Leu
    130                 135                 140

Gly Gln Thr Val Gln Ala Ser Asp Ser Leu Thr Gly Ala Glu Glu Thr
145                 150                 155                 160

Leu Asn Gly Leu Ile Gln Phe Asp Ala Ala Ile Gln Pro Gly Asp Ser
                165                 170                 175

Gly Gly Pro Val Val Asn Gly Leu Gly Gln Val Val Gly Met Asn Thr
            180                 185                 190

Ala Ala Ser Asp Asn Phe Gln Leu Ser Gln Gly Gly Gln Gly Phe Ala
        195                 200                 205

Ile Pro Ile Gly Gln Ala Met Ala Ile Ala Gly Gln Ile Arg Ser Gly
    210                 215                 220

Gly Gly Ser Pro Thr Val His Ile Gly Pro Thr Ala Phe Leu Gly Leu
225                 230                 235                 240

Gly Val Val Asp Asn Asn Gly Asn Gly Ala Arg Val Gln Arg Val Val
                245                 250                 255

Gly Ser Ala Pro Ala Ala Ser Leu Gly Ile Ser Thr Gly Asp Val Ile
            260                 265                 270

Thr Ala Val Asp Gly Ala Pro Ile Asn Ser Ala Thr Ala Met Ala Asp
        275                 280                 285

Ala Leu Asn Gly His His Pro Gly Asp Val Ile Ser Val Thr Trp Gln
    290                 295                 300

Thr Lys Ser Gly Gly Thr Arg Thr Gly Asn Val Thr Leu Ala Glu Gly
305                 310                 315                 320
```

Pro Pro Ala

<210> SEQ ID NO 4
<211> LENGTH: 723
<212> TYPE: PRT
<213> ORGANISM: Artificial
<220> FEATURE:
<223> OTHER INFORMATION: M72

<400> SEQUENCE: 4

```
Met Thr Ala Ala Ser Asp Asn Phe Gln Leu Ser Gln Gly Gly Gln Gly
1               5                   10                  15

Phe Ala Ile Pro Ile Gly Gln Ala Met Ala Ile Ala Gly Gln Ile Arg
            20                  25                  30

Ser Gly Gly Gly Ser Pro Thr Val His Ile Gly Pro Thr Ala Phe Leu
        35                  40                  45

Gly Leu Gly Val Val Asp Asn Asn Gly Asn Gly Ala Arg Val Gln Arg
    50                  55                  60

Val Val Gly Ser Ala Pro Ala Ala Ser Leu Gly Ile Ser Thr Gly Asp
65                  70                  75                  80

Val Ile Thr Ala Val Asp Gly Ala Pro Ile Asn Ser Ala Thr Ala Met
                85                  90                  95

Ala Asp Ala Leu Asn Gly His His Pro Gly Asp Val Ile Ser Val Thr
            100                 105                 110

Trp Gln Thr Lys Ser Gly Gly Thr Arg Thr Gly Asn Val Thr Leu Ala
        115                 120                 125

Glu Gly Pro Pro Ala Glu Phe Met Val Asp Phe Gly Ala Leu Pro Pro
    130                 135                 140

Glu Ile Asn Ser Ala Arg Met Tyr Ala Gly Pro Gly Ser Ala Ser Leu
145                 150                 155                 160

Val Ala Ala Ala Gln Met Trp Asp Ser Val Ala Ser Asp Leu Phe Ser
                165                 170                 175

Ala Ala Ser Ala Phe Gln Ser Val Val Trp Gly Leu Thr Val Gly Ser
            180                 185                 190

Trp Ile Gly Ser Ser Ala Gly Leu Met Val Ala Ala Ser Pro Tyr
        195                 200                 205

Val Ala Trp Met Ser Val Thr Ala Gly Gln Ala Glu Leu Thr Ala Ala
    210                 215                 220

Gln Val Arg Val Ala Ala Ala Tyr Glu Thr Ala Tyr Gly Leu Thr
225                 230                 235                 240

Val Pro Pro Pro Val Ile Ala Glu Asn Arg Ala Glu Leu Met Ile Leu
                245                 250                 255

Ile Ala Thr Asn Leu Leu Gly Gln Asn Thr Pro Ala Ile Ala Val Asn
            260                 265                 270

Glu Ala Glu Tyr Gly Glu Met Trp Ala Gln Asp Ala Ala Ala Met Phe
        275                 280                 285

Gly Tyr Ala Ala Ala Thr Ala Thr Ala Thr Leu Leu Pro Phe
    290                 295                 300

Glu Glu Ala Pro Glu Met Thr Ser Ala Gly Gly Leu Leu Glu Gln Ala
305                 310                 315                 320

Ala Ala Val Glu Glu Ala Ser Asp Thr Ala Ala Asn Gln Leu Met
                325                 330                 335

Asn Asn Val Pro Gln Ala Leu Gln Gln Leu Ala Gln Pro Thr Gln Gly
            340                 345                 350

Thr Thr Pro Ser Ser Lys Leu Gly Gly Leu Trp Lys Thr Val Ser Pro
```

```
                355                 360                 365
His Arg Ser Pro Ile Ser Asn Met Val Ser Met Ala Asn Asn His Met
    370                 375                 380
Ser Met Thr Asn Ser Gly Val Ser Met Thr Asn Thr Leu Ser Ser Met
385                 390                 395                 400
Leu Lys Gly Phe Ala Pro Ala Ala Ala Gln Ala Val Gln Thr Ala
            405                 410                 415
Ala Gln Asn Gly Val Arg Ala Met Ser Ser Leu Gly Ser Ser Leu Gly
        420                 425                 430
Ser Ser Gly Leu Gly Gly Val Ala Ala Asn Leu Gly Arg Ala Ala
        435                 440                 445
Ser Val Gly Ser Leu Ser Val Pro Gln Ala Trp Ala Ala Ala Asn Gln
    450                 455                 460
Ala Val Thr Pro Ala Ala Arg Ala Leu Pro Leu Thr Ser Leu Thr Ser
465                 470                 475                 480
Ala Ala Glu Arg Gly Pro Gly Gln Met Leu Gly Gly Leu Pro Val Gly
            485                 490                 495
Gln Met Gly Ala Arg Ala Gly Gly Leu Ser Gly Val Leu Arg Val
        500                 505                 510
Pro Pro Arg Pro Tyr Val Met Pro His Ser Pro Ala Ala Gly Asp Ile
        515                 520                 525
Ala Pro Pro Ala Leu Ser Gln Asp Arg Phe Ala Asp Phe Pro Ala Leu
        530                 535                 540
Pro Leu Asp Pro Ser Ala Met Val Ala Gln Val Gly Pro Gln Val Val
545                 550                 555                 560
Asn Ile Asn Thr Lys Leu Gly Tyr Asn Asn Ala Val Gly Ala Gly Thr
            565                 570                 575
Gly Ile Val Ile Asp Pro Asn Gly Val Val Leu Thr Asn Asn His Val
        580                 585                 590
Ile Ala Gly Ala Thr Asp Ile Asn Ala Phe Ser Val Gly Ser Gly Gln
        595                 600                 605
Thr Tyr Gly Val Asp Val Val Gly Tyr Asp Arg Thr Gln Asp Val Ala
    610                 615                 620
Val Leu Gln Leu Arg Gly Ala Gly Gly Leu Pro Ser Ala Ala Ile Gly
625                 630                 635                 640
Gly Gly Val Ala Val Gly Glu Pro Val Val Ala Met Gly Asn Ser Gly
            645                 650                 655
Gly Gln Gly Gly Thr Pro Arg Ala Val Pro Gly Arg Val Val Ala Leu
        660                 665                 670
Gly Gln Thr Val Gln Ala Ser Asp Ser Leu Thr Gly Ala Glu Glu Thr
        675                 680                 685
Leu Asn Gly Leu Ile Gln Phe Asp Ala Ala Ile Gln Pro Gly Asp Ala
    690                 695                 700
Gly Gly Pro Val Val Asn Gly Leu Gly Gln Val Val Gly Met Asn Thr
705                 710                 715                 720
Ala Ala Ser

<210> SEQ ID NO 5
<211> LENGTH: 725
<212> TYPE: PRT
<213> ORGANISM: Artificial
<220> FEATURE:
<223> OTHER INFORMATION: M72-2His

<400> SEQUENCE: 5
```

```
Met His His Thr Ala Ala Ser Asp Asn Phe Gln Leu Ser Gln Gly Gly
1               5                   10                  15

Gln Gly Phe Ala Ile Pro Ile Gly Gln Ala Met Ala Ile Ala Gly Gln
            20                  25                  30

Ile Arg Ser Gly Gly Gly Ser Pro Thr Val His Ile Gly Pro Thr Ala
            35                  40                  45

Phe Leu Gly Leu Gly Val Val Asp Asn Asn Gly Asn Gly Ala Arg Val
        50                  55                  60

Gln Arg Val Val Gly Ser Ala Pro Ala Ala Ser Leu Gly Ile Ser Thr
65                  70                  75                  80

Gly Asp Val Ile Thr Ala Val Asp Gly Ala Pro Ile Asn Ser Ala Thr
                85                  90                  95

Ala Met Ala Asp Ala Leu Asn Gly His His Pro Gly Asp Val Ile Ser
            100                 105                 110

Val Thr Trp Gln Thr Lys Ser Gly Gly Thr Arg Thr Gly Asn Val Thr
        115                 120                 125

Leu Ala Glu Gly Pro Pro Ala Glu Phe Met Val Asp Phe Gly Ala Leu
    130                 135                 140

Pro Pro Glu Ile Asn Ser Ala Arg Met Tyr Ala Gly Pro Gly Ser Ala
145                 150                 155                 160

Ser Leu Val Ala Ala Ala Gln Met Trp Asp Ser Val Ala Ser Asp Leu
                165                 170                 175

Phe Ser Ala Ala Ser Ala Phe Gln Ser Val Val Trp Gly Leu Thr Val
            180                 185                 190

Gly Ser Trp Ile Gly Ser Ser Ala Gly Leu Met Val Ala Ala Ala Ser
        195                 200                 205

Pro Tyr Val Ala Trp Met Ser Val Thr Ala Gly Gln Ala Glu Leu Thr
210                 215                 220

Ala Ala Gln Val Arg Val Ala Ala Ala Tyr Glu Thr Ala Tyr Gly
225                 230                 235                 240

Leu Thr Val Pro Pro Pro Val Ile Ala Glu Asn Arg Ala Glu Leu Met
            245                 250                 255

Ile Leu Ile Ala Thr Asn Leu Leu Gly Gln Asn Thr Pro Ala Ile Ala
            260                 265                 270

Val Asn Glu Ala Glu Tyr Gly Glu Met Trp Ala Gln Asp Ala Ala Ala
        275                 280                 285

Met Phe Gly Tyr Ala Ala Ala Thr Ala Thr Ala Thr Ala Thr Leu Leu
    290                 295                 300

Pro Phe Glu Glu Ala Pro Glu Met Thr Ser Ala Gly Gly Leu Leu Glu
305                 310                 315                 320

Gln Ala Ala Ala Val Glu Glu Ala Ser Asp Thr Ala Ala Ala Asn Gln
                325                 330                 335

Leu Met Asn Asn Val Pro Gln Ala Leu Gln Gln Leu Ala Gln Pro Thr
            340                 345                 350

Gln Gly Thr Thr Pro Ser Ser Lys Leu Gly Gly Leu Trp Lys Thr Val
        355                 360                 365

Ser Pro His Arg Ser Pro Ile Ser Asn Met Val Ser Met Ala Asn Asn
370                 375                 380

His Met Ser Met Thr Asn Ser Gly Val Ser Met Thr Asn Thr Leu Ser
385                 390                 395                 400

Ser Met Leu Lys Gly Phe Ala Pro Ala Ala Ala Gln Ala Val Gln
                405                 410                 415
```

```
Thr Ala Ala Gln Asn Gly Val Arg Ala Met Ser Ser Leu Gly Ser Ser
                420                 425                 430

Leu Gly Ser Ser Gly Leu Gly Gly Val Ala Ala Asn Leu Gly Arg
        435                 440                 445

Ala Ala Ser Val Gly Ser Leu Ser Val Pro Gln Ala Trp Ala Ala Ala
    450                 455                 460

Asn Gln Ala Val Thr Pro Ala Arg Ala Leu Pro Leu Thr Ser Leu
465                 470                 475                 480

Thr Ser Ala Ala Glu Arg Gly Pro Gly Gln Met Leu Gly Gly Leu Pro
                485                 490                 495

Val Gly Gln Met Gly Ala Arg Ala Gly Gly Leu Ser Gly Val Leu
            500                 505                 510

Arg Val Pro Pro Arg Pro Tyr Val Met Pro His Ser Pro Ala Ala Gly
            515                 520                 525

Asp Ile Ala Pro Pro Ala Leu Ser Gln Asp Arg Phe Ala Asp Phe Pro
        530                 535                 540

Ala Leu Pro Leu Asp Pro Ser Ala Met Val Ala Gln Val Gly Pro Gln
545                 550                 555                 560

Val Val Asn Ile Asn Thr Lys Leu Gly Tyr Asn Asn Ala Val Gly Ala
                565                 570                 575

Gly Thr Gly Ile Val Ile Asp Pro Asn Gly Val Val Leu Thr Asn Asn
            580                 585                 590

His Val Ile Ala Gly Ala Thr Asp Ile Asn Ala Phe Ser Val Gly Ser
        595                 600                 605

Gly Gln Thr Tyr Gly Val Asp Val Val Gly Tyr Asp Arg Thr Gln Asp
    610                 615                 620

Val Ala Val Leu Gln Leu Arg Gly Ala Gly Gly Leu Pro Ser Ala Ala
625                 630                 635                 640

Ile Gly Gly Gly Val Ala Val Gly Glu Pro Val Val Ala Met Gly Asn
                645                 650                 655

Ser Gly Gly Gln Gly Gly Thr Pro Arg Ala Val Pro Gly Arg Val Val
            660                 665                 670

Ala Leu Gly Gln Thr Val Gln Ala Ser Asp Ser Leu Thr Gly Ala Glu
        675                 680                 685

Glu Thr Leu Asn Gly Leu Ile Gln Phe Asp Ala Ala Ile Gln Pro Gly
    690                 695                 700

Asp Ala Gly Gly Pro Val Val Asn Gly Leu Gly Gln Val Val Gly Met
705                 710                 715                 720

Asn Thr Ala Ala Ser
                725

<210> SEQ ID NO 6
<211> LENGTH: 546
<212> TYPE: PRT
<213> ORGANISM: Varicella zoster

<400> SEQUENCE: 6

Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
                20                  25                  30

Leu Arg Tyr Asp Asp Phe His Ile Asp Glu Asp Lys Leu Asp Thr Asn
            35                  40                  45

Ser Val Tyr Glu Pro Tyr Tyr His Ser Asp His Ala Glu Ser Ser Trp
        50                  55                  60
```

-continued

```
Val Asn Arg Gly Glu Ser Ser Arg Lys Ala Tyr Asp His Asn Ser Pro
 65                  70                  75                  80

Tyr Ile Trp Pro Arg Asn Asp Tyr Asp Gly Phe Leu Glu Asn Ala His
                 85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
            115                 120                 125

Asp Thr Gly Ile His Val Ile Pro Thr Leu Asn Gly Asp Asp Arg His
            130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
            195                 200                 205

Thr Gly Asp Ala Ala Pro Ala Ile Gln His Ile Cys Leu Lys His Thr
210                 215                 220

Thr Cys Phe Gln Asp Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
            275                 280                 285

Leu Arg Thr Glu Lys Gln Tyr Leu Gly Val Tyr Ile Trp Asn Met Arg
290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
            355                 360                 365

Glu Ala Pro Phe Asp Leu Leu Leu Glu Trp Leu Tyr Val Pro Ile Asp
            370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
            435                 440                 445

Glu Pro Ser Phe Gly Leu Ile Leu His Asp Gly Gly Thr Thr Leu Lys
            450                 455                 460

Phe Val Asp Thr Pro Glu Ser Leu Ser Gly Leu Tyr Val Phe Val Val
465                 470                 475                 480
```

Tyr Phe Asn Gly His Val Glu Ala Val Ala Tyr Thr Val Val Ser Thr
            485                 490                 495

Val Asp His Phe Val Asn Ala Ile Glu Glu Arg Gly Phe Pro Pro Thr
        500                 505                 510

Ala Gly Gln Pro Pro Ala Thr Thr Lys Pro Lys Glu Ile Thr Pro Val
            515                 520                 525

Asn Pro Gly Thr Ser Pro Leu Ile Arg Tyr Ala Ala Trp Thr Gly Gly
        530                 535                 540

Leu Ala
545

<210> SEQ ID NO 7
<211> LENGTH: 514
<212> TYPE: PRT
<213> ORGANISM: respiratory syncytial virus

<400> SEQUENCE: 7

Met Glu Leu Leu Ile Leu Lys Thr Asn Ala Ile Thr Ala Ile Leu Ala
1               5                   10                  15

Ala Val Thr Leu Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Ser Ala Val Thr Glu Leu Gln Leu Leu
                85                  90                  95

Met Gln Ser Thr Pro Ala Thr Asn Asn Lys Phe Leu Gly Phe Leu Gln
            100                 105                 110

Gly Val Gly Ser Ala Ile Ala Ser Gly Ile Ala Val Ser Lys Val Leu
        115                 120                 125

His Leu Glu Gly Glu Val Asn Lys Ile Lys Ser Ala Leu Leu Ser Thr
    130                 135                 140

Asn Lys Ala Val Val Ser Leu Ser Asn Gly Val Ser Val Leu Thr Ser
145                 150                 155                 160

Lys Val Leu Asp Leu Lys Asn Tyr Ile Asp Lys Gln Leu Leu Pro Ile
                165                 170                 175

Val Asn Lys Gln Ser Cys Ser Ile Ser Asn Ile Glu Thr Val Ile Glu
            180                 185                 190

Phe Gln Gln Lys Asn Asn Arg Leu Leu Glu Ile Thr Arg Glu Phe Ser
        195                 200                 205

Val Asn Ala Gly Val Thr Thr Pro Val Ser Thr Tyr Met Leu Thr Asn
    210                 215                 220

Ser Glu Leu Leu Ser Leu Ile Asn Asp Met Pro Ile Thr Asn Asp Gln
225                 230                 235                 240

Lys Lys Leu Met Ser Asn Asn Val Gln Ile Val Arg Gln Gln Ser Tyr
                245                 250                 255

Ser Ile Met Ser Ile Ile Lys Glu Glu Val Leu Ala Tyr Val Val Gln
            260                 265                 270

Leu Pro Leu Tyr Gly Val Ile Asp Thr Pro Cys Trp Lys Leu His Thr
        275                 280                 285

Ser Pro Leu Cys Thr Thr Asn Thr Lys Glu Gly Ser Asn Ile Cys Leu
    290                 295                 300

Thr Arg Thr Asp Arg Gly Trp Tyr Cys Asp Asn Ala Gly Ser Val Ser
305                 310                 315                 320

Phe Phe Pro Leu Ala Glu Thr Cys Lys Val Gln Ser Asn Arg Val Phe
            325                 330                 335

Cys Asp Thr Met Asn Ser Leu Thr Leu Pro Ser Glu Val Asn Leu Cys
            340                 345                 350

Asn Ile Asp Ile Phe Asn Pro Lys Tyr Asp Cys Lys Ile Met Thr Ser
            355                 360                 365

Lys Thr Asp Val Ser Ser Val Ile Thr Ser Leu Gly Ala Ile Val
        370                 375                 380

Ser Cys Tyr Gly Lys Thr Lys Cys Thr Ala Ser Asn Lys Asn Arg Gly
385                 390                 395                 400

Ile Ile Lys Thr Phe Ser Asn Gly Cys Asp Tyr Val Ser Asn Lys Gly
            405                 410                 415

Val Asp Thr Val Ser Val Gly Asn Thr Leu Tyr Tyr Val Asn Lys Gln
            420                 425                 430

Glu Gly Lys Ser Leu Tyr Val Lys Gly Glu Pro Ile Ile Asn Phe Tyr
        435                 440                 445

Asp Pro Leu Val Phe Pro Ser Asp Glu Phe Asp Ala Ser Ile Ser Gln
450                 455                 460

Val Asn Glu Lys Ile Asn Gly Thr Leu Ala Phe Ile Arg Lys Ser Asp
465                 470                 475                 480

Glu Lys Leu His Asn Val Glu Asp Lys Ile Glu Ile Leu Ser Lys
            485                 490                 495

Ile Tyr His Ile Glu Asn Glu Ile Ala Arg Ile Lys Lys Leu Ile Gly
            500                 505                 510

Glu Ala

<210> SEQ ID NO 8
<211> LENGTH: 488
<212> TYPE: PRT
<213> ORGANISM: Human immunodeficiency virus

<400> SEQUENCE: 8

Asn Thr Glu Asp Leu Trp Val Thr Val Tyr Tyr Gly Val Pro Val Trp
1               5                   10                  15

Arg Asp Ala Lys Thr Thr Leu Phe Cys Ala Ser Asp Ala Lys Ala Tyr
            20                  25                  30

Glu Thr Glu Val His Asn Val Trp Ala Thr His Ala Cys Val Pro Thr
        35                  40                  45

Asp Pro Asn Pro Gln Glu Ile Val Leu Gly Asn Val Thr Glu Asn Phe
50                  55                  60

Asn Met Trp Lys Asn Asp Met Ala Asp Gln Met His Glu Asp Val Ile
65                  70                  75                  80

Ser Leu Trp Asp Gln Ser Leu Lys Pro Cys Val Lys Leu Thr Pro Leu
            85                  90                  95

Cys Val Thr Leu Asn Cys Thr Asp Thr Asn Val Thr Gly Asn Arg Thr
            100                 105                 110

Val Thr Gly Asn Ser Thr Asn Asn Thr Asn Gly Thr Gly Ile Tyr Asn
        115                 120                 125

Ile Glu Glu Met Lys Asn Cys Ser Phe Asn Ala Thr Thr Glu Leu Arg
130                 135                 140

Asp Lys Lys His Lys Glu Tyr Ala Leu Phe Tyr Arg Leu Asp Ile Val
145                 150                 155                 160

```
Pro Leu Asn Glu Asn Ser Asp Asn Phe Thr Tyr Arg Leu Ile Asn Cys
                165                 170                 175

Asn Thr Ser Thr Ile Thr Gln Ala Cys Pro Lys Val Ser Phe Asp Pro
            180                 185                 190

Ile Pro Ile His Tyr Cys Ala Pro Ala Gly Tyr Ala Ile Leu Lys Cys
            195                 200                 205

Asn Asn Lys Thr Phe Asn Gly Thr Gly Pro Cys Tyr Asn Val Ser Thr
        210                 215                 220

Val Gln Cys Thr His Gly Ile Lys Pro Val Val Ser Thr Gln Leu Leu
225                 230                 235                 240

Leu Asn Gly Ser Leu Ala Glu Glu Gly Ile Ile Ile Arg Ser Glu Asn
                245                 250                 255

Leu Thr Glu Asn Thr Lys Thr Ile Ile Val His Leu Asn Glu Ser Val
            260                 265                 270

Glu Ile Asn Cys Thr Arg Pro Asn Asn Asn Thr Arg Lys Ser Val Arg
        275                 280                 285

Ile Gly Pro Gly Gln Ala Phe Tyr Ala Thr Asn Asp Val Ile Gly Asn
        290                 295                 300

Ile Arg Gln Ala His Cys Asn Ile Ser Thr Asp Arg Trp Asn Lys Thr
305                 310                 315                 320

Leu Gln Gln Val Met Lys Lys Leu Gly Glu His Phe Pro Asn Lys Thr
                325                 330                 335

Ile Gln Phe Lys Pro His Ala Gly Gly Asp Leu Glu Ile Thr Met His
            340                 345                 350

Ser Phe Asn Cys Arg Gly Glu Phe Phe Tyr Cys Asn Thr Ser Asn Leu
        355                 360                 365

Phe Asn Ser Thr Tyr His Ser Asn Asn Gly Thr Tyr Lys Tyr Asn Gly
        370                 375                 380

Asn Ser Ser Ser Pro Ile Thr Leu Gln Cys Lys Ile Lys Gln Ile Val
385                 390                 395                 400

Arg Met Trp Gln Gly Val Gly Gln Ala Thr Tyr Ala Pro Pro Ile Ala
                405                 410                 415

Gly Asn Ile Thr Cys Arg Ser Asn Ile Thr Gly Ile Leu Leu Thr Arg
            420                 425                 430

Asp Gly Gly Phe Asn Thr Thr Asn Asn Thr Glu Thr Phe Arg Pro Gly
        435                 440                 445

Gly Gly Asp Met Arg Asp Asn Trp Arg Ser Glu Leu Tyr Lys Tyr Lys
        450                 455                 460

Val Val Glu Ile Lys Pro Leu Gly Ile Ala Pro Thr Lys Ala Lys Arg
465                 470                 475                 480

Arg Val Val Gln Arg Glu Lys Arg
                485

<210> SEQ ID NO 9
<211> LENGTH: 469
<212> TYPE: PRT
<213> ORGANISM: Human immunodeficiency virus

<400> SEQUENCE: 9

Ser Trp Val Thr Val Tyr Tyr Gly Val Pro Val Trp Lys Glu Ala Lys
1               5                   10                  15

Thr Thr Leu Phe Cys Ala Ser Asp Ala Lys Ala Tyr Glu Lys Glu Val
            20                  25                  30

His Asn Val Trp Ala Thr His Ala Cys Val Pro Thr Asp Pro Asn Pro
```

```
            35                  40                  45
Gln Glu Met Val Leu Ala Asn Val Thr Glu Asn Phe Asn Met Trp Lys
 50                  55                  60

Asn Asp Met Val Glu Gln Met His Glu Asp Ile Ile Ser Leu Trp Asp
 65                  70                  75                  80

Glu Ser Leu Lys Pro Cys Val Lys Leu Thr Pro Leu Cys Val Thr Leu
                 85                  90                  95

Asn Cys Thr Asn Val Lys Gly Asn Glu Ser Asp Thr Ser Glu Val Met
            100                 105                 110

Lys Asn Cys Ser Phe Lys Ala Thr Thr Glu Leu Lys Asp Lys Lys His
            115                 120                 125

Lys Val His Ala Leu Phe Tyr Lys Leu Asp Val Val Pro Leu Asn Gly
130                 135                 140

Asn Ser Ser Ser Gly Glu Tyr Arg Leu Ile Asn Cys Asn Thr Ser
145                 150                 155                 160

Ala Ile Thr Gln Ala Cys Pro Lys Val Ser Phe Asp Pro Ile Pro Leu
                165                 170                 175

His Tyr Cys Ala Pro Ala Gly Phe Ala Ile Leu Lys Cys Asn Asn Lys
            180                 185                 190

Thr Phe Asn Gly Thr Gly Pro Cys Arg Asn Val Ser Thr Val Gln Cys
            195                 200                 205

Thr His Gly Ile Lys Pro Val Val Ser Thr Gln Leu Leu Leu Asn Gly
            210                 215                 220

Ser Leu Ala Glu Glu Ile Ile Ile Arg Ser Glu Asn Leu Thr Asn
225                 230                 235                 240

Asn Ala Lys Thr Ile Ile Val His Leu Asn Glu Ser Val Asn Ile Val
                245                 250                 255

Cys Thr Arg Pro Asn Asn Asn Thr Arg Lys Ser Ile Arg Ile Gly Pro
            260                 265                 270

Gly Gln Thr Phe Tyr Ala Thr Gly Asp Ile Ile Gly Asn Ile Arg Gln
            275                 280                 285

Ala His Cys Asn Ile Asn Glu Ser Lys Trp Asn Asn Thr Leu Gln Lys
290                 295                 300

Val Gly Glu Glu Leu Ala Lys His Phe Pro Ser Lys Thr Ile Lys Phe
305                 310                 315                 320

Glu Pro Ser Ser Gly Gly Asp Leu Glu Ile Thr Thr His Ser Phe Asn
                325                 330                 335

Cys Arg Gly Glu Phe Phe Tyr Cys Asn Thr Ser Asp Leu Phe Asn Gly
            340                 345                 350

Thr Tyr Arg Asn Gly Thr Tyr Asn His Thr Gly Arg Ser Ser Asn Gly
            355                 360                 365

Thr Ile Thr Leu Gln Cys Lys Ile Lys Gln Ile Ile Asn Met Trp Gln
            370                 375                 380

Glu Val Gly Arg Ala Ile Tyr Ala Pro Pro Ile Glu Gly Glu Ile Thr
385                 390                 395                 400

Cys Asn Ser Asn Ile Thr Gly Leu Leu Leu Leu Arg Asp Gly Gly Gln
                405                 410                 415

Ser Asn Glu Thr Asn Asp Thr Glu Thr Phe Arg Pro Gly Gly Gly Asp
            420                 425                 430
```

```
Met Arg Asp Asn Trp Arg Ser Glu Leu Tyr Lys Tyr Lys Val Val Glu
        435                 440                 445

Ile Lys Pro Leu Gly Val Ala Pro Thr Glu Ala Lys Arg Arg Val Val
    450                 455                 460

Glu Arg Glu Lys Arg
465
```

METHODS FOR MANUFACTURING AN ADJUVANT

CROSS-REFERENCE TO RELATED APPLICATIONS

This application is filed pursuant to 35 U.S.C. § 371 as a United States National Phase Application of International Application No. PCT/EP2018/057488 filed Mar. 23, 2018 which claims priority from U.S. Provisional No. 62/512,352 filed May 30, 2017.

TECHNICAL FIELD

The present invention relates to methods for manufacturing an adjuvant comprising a saponin using a microfluidic device and to related aspects.

BACKGROUND OF THE INVENTION

Adjuvants are included in vaccines to improve humoral and cellular immune responses, particularly in the case of poorly immunogenic subunit vaccines. Similar to natural infections by pathogens, adjuvants rely on the activation of the innate immune system to promote long-lasting adaptive immunity. As simultaneous activation of multiple innate immune pathways is a feature of natural infections, adjuvants may combine multiple immunostimulants in order to promote adaptive immune responses to vaccination.

The Adjuvant System 01 (AS01) is a liposome-based adjuvant which contains two immunostimulants, 3-O-desacyl-4'-monophosphoryl lipid A (3D-MPL) and QS-21 (Garcon and Van Mechelen, 2011; Didierlaurent et al, 2017). The TLR4 agonist 3D-MPL is a non-toxic derivative of the lipopolysaccharide from *Salmonella minnesota*. QS-21 is a natural saponin molecule extracted from the bark of the South American tree *Quillaja saponaria* Molina (Kensil et al., 1991; Ragupathi et al., 2011). AS01 is included in the recently developed malaria vaccine RTS,S (Mosquirix™) and Herpes zoster HZ/su vaccine (Shingrix™) and in multiple candidate vaccines in development against pathogens such as human immunodeficiency virus and *Mycobacterium tuberculosis*. During preclinical and clinical evaluation of these candidate vaccines, both antigen-specific antibody and CD4$^+$ T cell immunity were consistently observed. The ability of AS01 to consistently generate cellular immune responses to vaccination sets it apart from other adjuvants that typically mainly promote humoral responses to vaccination (Black et al., 2015; Garcon and Van Mechelen, 2011). Concomitantly, AS01-adjuvanted vaccines have been efficient in promoting immunogenicity to vaccination in challenging populations, such as infants (with RTS,S) and older adults (with HZ/su).

AS01 injection results in rapid and transient activation of innate immunity in animal models. Neutrophils and monocytes are rapidly recruited to the draining lymph node (dLN) upon immunization. Moreover, AS01 induces recruitment and activation of MHCII$^{high}$ dendritic cells (DC), which are necessary for T cell activation (Didierlaurent A. M. et al., 2014). Some data are also available on the mechanism of action of the components of AS01. 3D-MPL signals via TLR4, stimulating NF-κB transcriptional activity and cytokine production and directly activates antigen-presenting cells (APCs) both in humans and in mice (De Becker et al., 2000; Ismaili et al., 2002; Martin et al., 2003; Mata-Haro et al., 2007). QS-21 promotes high antigen-specific antibody responses and CD8$^+$ T-cell responses in mice (Kensil and Kammer, 1998; Newman et al., 1992; Soltysik et al., 1995) and antigen-specific antibody responses in humans (Livingston et al., 1994). Because of its physical properties, it is thought that QS-21 might act as a danger signal in vivo (Lambrecht et al., 2009; Li et al., 2008). Although QS-21 has been shown to activate ASC-NLRP3 inflammasome and subsequent IL-1β/IL-18 release (Marty-Roix, R. et al., 2016), the exact molecular pathways involved in the adjuvant effect of saponins have yet to be clearly defined.

3D-MPL and QS-21 have been shown to act synergistically in the induction of immune responses. Furthermore, the manner in which both immunostimulants are provided has been shown to be an important factor which influences the quality of the induced responses, with the liposomal presentation in AS01 providing higher potency than the oil-in-water emulsion based AS02. (Dendouga et al. 2012)

US2010202928 and US2015115488 describe the preparation of liposomes using microfluidics.

WO2013/192310 discloses methods for the mass production of nanoparticles through controlled microvortices, The methods are stated to be of use in the preparation of polymeric or non-polymeric particles and hybrid particles.

Kim et al *Nano Letters* 2012 12(7):3587-3591 also discloses methods for the mass production of nanoparticles through controlled microvortices.

Hood et al *Small* 2015 11 43:5790-5799 describes methods for the production of liposomes using microfluidics.

There remains a need for new manufacturing approaches which enable the safe, convenient and cost effective production of liposomal adjuvants on a commercially viable scale while maintaining the immunological performance arising from conventional manufacturing approaches.

SUMMARY OF THE INVENTION

It has now surprisingly been found that a microfluidic device can be used to manufacture a liposomal adjuvant comprising a saponin while maintaining comparable immunological performance to conventional manufacturing approaches.

Accordingly, there is provided a method of manufacturing a liposomal adjuvant comprising a saponin using a microfluidic device, comprising the following steps:
  (a) mixing in the device a first solution comprising a solvent, phosphatidylcholine lipid and a sterol, and a second solution comprising water and the saponin; and
  (b) removing the solvent.

Also provided is a method of manufacturing a liposomal adjuvant comprising a saponin using a microfluidic device, comprising the following steps:
  (a) mixing in the device a first solution comprising a solvent, phosphatidylcholine lipid and a sterol, and a second solution comprising water;
  (b) adding the saponin; and
  (c) removing the solvent.

Further provided is a method of manufacturing a liposomal adjuvant comprising a saponin using a microfluidic device, comprising the following steps:
  (a) mixing in the device a first solution comprising a solvent, phosphatidylcholine lipid and a sterol, and a second solution comprising water;
  (b) removing the solvent; and
  (c) adding the saponin.

The present invention also provides a method of manufacturing a liposomal concentrate of use in preparing a liposomal adjuvant comprising a saponin using a microfluidic device, comprising the step of mixing in the device a first solution comprising a solvent, phosphatidylcholine lipid and a sterol, and a second solution comprising water and the saponin.

Also provided is a method of manufacturing a liposomal concentrate of use in preparing a liposomal adjuvant comprising a saponin using a microfluidic device, comprising the following steps:
(a) mixing in the device a first solution comprising a solvent, phosphatidylcholine lipid and a sterol, and a second solution comprising water; and
(b) adding the saponin.

Further provided is a liposomal concentrate of use in preparing a liposomal adjuvant, said liposomal concentrate comprising water, a solvent, phosphatidylcholine lipid, saponin and cholesterol. Accordingly, there is provided a method of manufacturing a liposomal adjuvant comprising a saponin using a microfluidic device, comprising the following steps:
(a) mixing in the device a first solution comprising a solvent, DOPC and a sterol, and a second solution comprising water and the saponin; and
(b) removing the solvent.

Also provided is a method of manufacturing a liposomal adjuvant comprising a saponin using a microfluidic device, comprising the following steps:
(a) mixing in the device a first solution comprising a solvent, DOPC and a sterol, and a second solution comprising water;
(b) adding the saponin; and
(c) removing the solvent.

Further provided is a method of manufacturing a liposomal adjuvant comprising a saponin using a microfluidic device, comprising the following steps:
(a) mixing in the device a first solution comprising a solvent, DOPC and a sterol, and a second solution comprising water;
(b) removing the solvent; and
(c) adding the saponin.

The present invention also provides a method of manufacturing a liposomal concentrate of use in preparing a liposomal adjuvant comprising a saponin using a microfluidic device, comprising the step of mixing in the device a first solution comprising a solvent, DOPC and a sterol, and a second solution comprising water and the saponin.

Also provided is a method of manufacturing a liposomal concentrate of use in preparing a liposomal adjuvant comprising a saponin using a microfluidic device, comprising the following steps:
(a) mixing in the device a first solution comprising a solvent, DOPC and a sterol, and a second solution comprising water; and
(b) adding the saponin.

Further provided is a liposomal concentrate of use in preparing a liposomal adjuvant, said liposomal concentrate comprising water, a solvent, DOPC, saponin and cholesterol.

The present invention additionally provides a solution comprising a solvent and 100-170 mg/ml lipid, wherein the solvent comprises 70-90% v/v ethanol and 10-30% v/v isopropyl alcohol. Such solutions may be used in the manufacture of liposomes, such as a liposomal adjuvant.

BRIEF DESCRIPTION OF THE DRAWINGS

FIG. 8: Detail of Example 4 operating conditions and organisational arrangements
FIG. 10: Results of Example 4

DESCRIPTION OF SEQUENCE IDENTIFIERS

Figure 1:
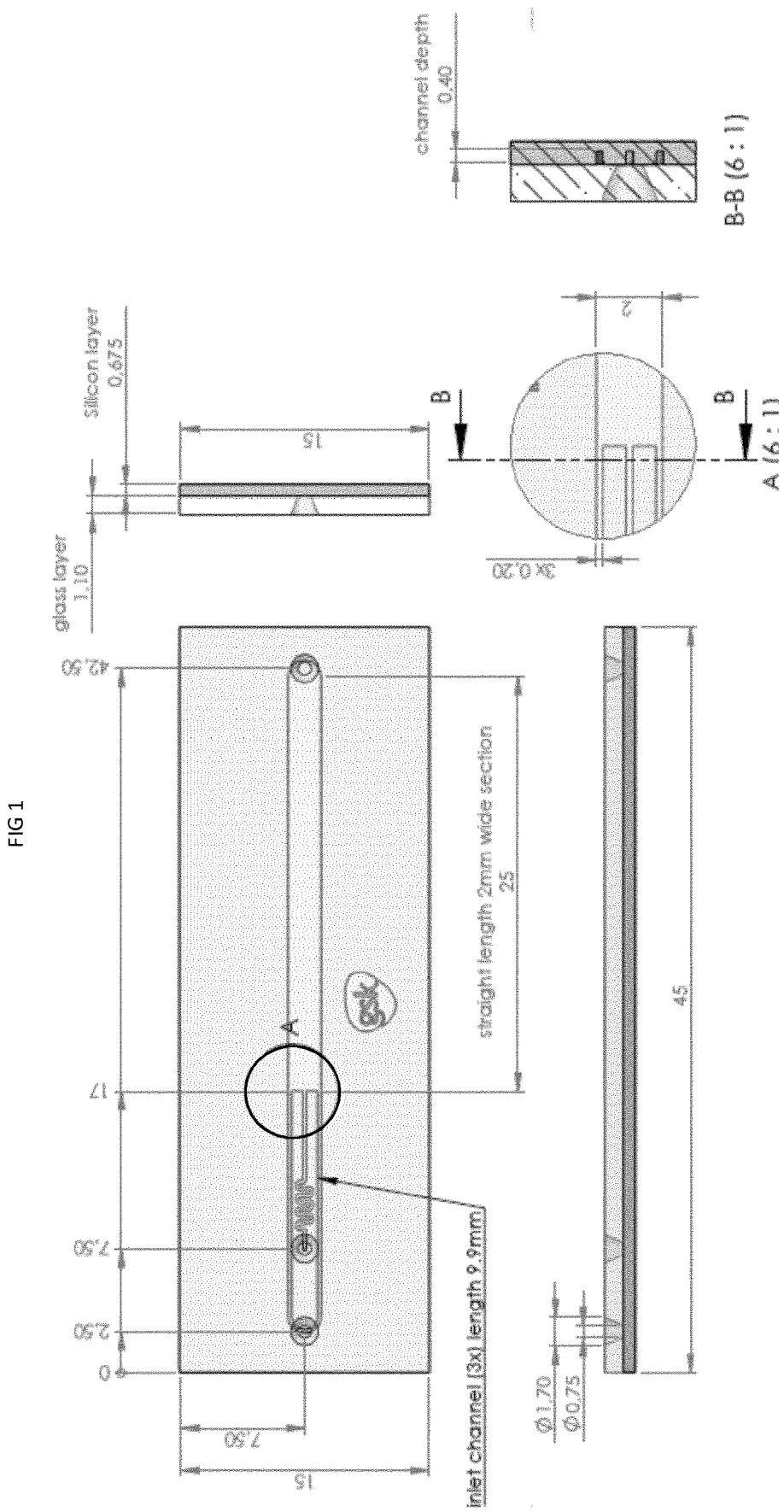
FIG. 1: Schematic of single mixing chamber microfluidic chip

SEQ ID No. 1: RTS polypeptide sequence
SEQ ID No. 2: *M. tuberculosis* H37Rv strain Rv1196 polypeptide sequence
SEQ ID No. 3: *M. tuberculosis* H37Rv strain Rv0125 polypeptide sequence
SEQ ID No. 4: M72 fusion polypeptide sequence
SEQ ID No. 5: M72-2his fusion polypeptide sequence
SEQ ID No. 6: Varicella zoster virus truncated gE polypeptide sequence
SEQ ID No. 7: Conformationally constrained RSV PreF antigen polypeptide sequence
SEQ ID No. 8: HIV TV1 gp120 polypeptide sequence
SEQ ID No. 9: HIV 1086.0 gp120 polypeptide sequence

DETAILED DESCRIPTION

The present invention provides a method of manufacturing a liposomal adjuvant comprising a saponin using a microfluidic device, comprising the following steps:
(a) mixing in the device a first solution comprising a solvent, phosphatidylcholine lipid and a sterol, and a second solution comprising water and the saponin; and
(b) removing the solvent.

Also provided is a method of manufacturing a liposomal adjuvant comprising a saponin using a microfluidic device, comprising the following steps:
(a) mixing in the device a first solution comprising a solvent, phosphatidylcholine lipid and a sterol, and a second solution comprising water;
(b) adding the saponin; and
(c) removing the solvent.

Further provided is a method of manufacturing a liposomal adjuvant comprising a saponin using a microfluidic device, comprising the following steps:
(a) mixing in the device a first solution comprising a solvent, phosphatidylcholine lipid and a sterol, and a second solution comprising water;
(b) removing the solvent; and
(c) adding the saponin.

The present invention also provides a method of manufacturing a liposomal concentrate of use in preparing a liposomal adjuvant comprising a saponin using a microfluidic device, comprising the step of mixing in the device a first solution comprising a solvent, phosphatidylcholine lipid and a sterol, and a second solution comprising water and the saponin.

Also provided is a method of manufacturing a liposomal concentrate of use in preparing a liposomal adjuvant comprising a saponin using a microfluidic device, comprising the following steps:
(a) mixing in the device a first solution comprising a solvent, phosphatidylcholine lipid and a sterol, and a second solution comprising water; and
(b) adding the saponin.

Further provided is a liposomal concentrate of use in preparing a liposomal adjuvant, said liposomal concentrate comprising water, a solvent, phosphatidylcholine lipid, saponin and cholesterol.

The present invention also provides a method of manufacturing a liposomal adjuvant comprising a saponin using a microfluidic device, comprising the following steps:
(a) mixing in the device a first solution comprising a solvent, DOPC and a sterol, and a second solution comprising water and the saponin; and
(b) removing the solvent.

Also provided is a method of manufacturing a liposomal adjuvant comprising a saponin using a microfluidic device, comprising the following steps:
(a) mixing in the device a first solution comprising a solvent, DOPC and a sterol, and a second solution comprising water;
(b) adding the saponin; and
(c) removing the solvent.

Further provided is a method of manufacturing a liposomal adjuvant comprising a saponin using a microfluidic device, comprising the following steps:
(a) mixing in the device a first solution comprising a solvent, DOPC and a sterol, and a second solution comprising water;
(b) removing the solvent; and
(c) adding the saponin.

The present invention also provides a method of manufacturing a liposomal concentrate of use in preparing a liposomal adjuvant comprising a saponin using a microfluidic device, comprising the step of mixing in the device a first solution comprising a solvent, DOPC and a sterol, and a second solution comprising water and the saponin.

Also provided is a method of manufacturing a liposomal concentrate of use in preparing a liposomal adjuvant comprising a saponin using a microfluidic device, comprising the following steps:
(a) mixing in the device a first solution comprising a solvent, DOPC and a sterol, and a second solution comprising water; and
(b) adding the saponin.

Further provided is a liposomal concentrate of use in preparing a liposomal adjuvant, said liposomal concentrate comprising water, a solvent, DOPC, saponin and cholesterol.

The present invention additionally provides a solution comprising a solvent and 100-170 mg/ml lipid, wherein the solvent comprises 70-90% v/v ethanol and 10-30% v/v isopropyl alcohol.

The present invention additionally provides a solution comprising a solvent and 100-170 mg/ml lipid, wherein the solvent comprises 70-90% v/v ethanol and 10-30% v/v isopropyl alcohol. Such solutions may be used in the manufacture of liposomes, such as a liposomal adjuvant.

Microfluidic Devices

A microfluidic device is a fluid handing apparatus wherein typically at least one aspect has a dimension on a sub-mm scale and typically mixing occurs through passive means (i.e. through contact of fluid streams and without moving parts within the mixing chamber). The microfluidic device will comprise a mixing chamber within which the first solution and second solution are mixed.

The mixing chamber will typically have a cross-sectional area which is 25.6 mm$^2$ or less, such as 12.8 mm$^2$ or less, suitably 6.4 mm$^2$ or less, especially 3.2 mm$^2$ or less and in particular 1.6 mm$^2$ or less. The mixing chamber will typically have a cross-sectional area which is 0.1 mm$^2$ or more, suitably 0.2 mm$^2$ or more, especially 0.3 mm$^2$ or more and in particular 0.4 mm$^2$ or more. In some embodiments the mixing chamber will have a cross-sectional area which is 0.2-3.2 mm$^2$, such as 0.4-1.6 mm$^2$, especially 0.6-1.2 mm$^2$ and in particular 0.7-1.0 mm$^2$ (e.g. 0.8 mm$^2$).

The cross-section of the mixing chamber may be of any shape, though is typically symmetrical. The cross-section may be substantially rectangular (such as square). The cross-section may be elongate in nature, with the larger dimension being at least twice that of the perpendicular dimension, such as at least three times or at least four times. The larger dimension may be no more than ten times that of the perpendicular dimension, such as no more than eight times or no more than six times. The larger dimension will usually be two to ten times that of the perpendicular dimension, such as three to eight times, especially four to six times, in particular five times.

A rectangular cross-section may have a long side of 1-8 mm, such as 1-4 mm, for example 1.4-3.2 mm, especially 1.6-2.4 mm, in particular 1.8-2.2 mm (e.g. 2 mm). A rectangular cross-section may have a short side of 0.1 to 4 mm, for example, 0.1 to 2 mm, optionally 0.1-1.2 mm, such as 0.1-0.8 mm, especially 0.2-0.6 mm, in particular 0.3-0.5 mm (e.g. 0.4 mm).

The microfluidic device will have at least one inlet (such as one inlet) to the mixing chamber for delivery of the first solution. The device may have a plurality of inlets to the mixing chamber for delivery of the first solution, such as two inlets. Suitably the microfluidic device will have five or fewer inlets to the mixing chamber for delivery of the first solution, such as four or fewer.

The microfluidic device will have at least one inlet to the mixing chamber for delivery of the second solution. The device may have a plurality of inlets to the mixing chamber for delivery of the second solution, such as two inlets. Suitably the microfluidic device will have five or fewer inlets to the mixing chamber for delivery of the second solution, such as four or fewer.

To facilitate adequate mixing, the number of inlets for the first solution and second solution may be increased for mixing chambers with larger cross-sectional areas.

The cross-section of the inlets may be of any shape, though is typically symmetrical. The cross-section may be rectangular (such as square).

Each inlet will typically have a cross-sectional area which is 1.28 $mm^2$ or less, suitably 0.64 $mm^2$ or less, especially 0.32 $mm^2$ or less and in particular 0.16 $mm^2$ or less. Each inlet will typically have a cross-sectional area which is 0.01 $mm^2$ or more, suitably 0.02 $mm^2$ or more, especially 0.03 $mm^2$ or more and in particular 0.04 $mm^2$ or more. In some embodiments each inlet will have a cross-sectional area which is 0.02-0.32 $mm^2$, such as 0.04-0.16 $mm^2$, especially 0.06-0.12 $mm^2$ and in particular 0.07-0.10 $mm^2$ (e.g. 0.8 $mm^2$).

The total cross-sectional area of all inlets will suitably be less than 70% of the cross-sectional area of the mixing chamber, such as less than 60% and especially less than 50%.

Conveniently, the inlets may span the full length of one side of the mixing chamber.

The shape and size of each inlet may be varied independently. However, typically inlets for the first solution will be identical in shape and size, and inlets for the second solution will be identical in shape and size. Conveniently, all inlets are identical in shape and size. Each inlet may be 2-20% of the width of the mixing chamber, e.g. 5-15% such as 8-12%, especially 10%. A particular inlet design is rectangular in shape, 0.2 mm wide and spanning the full length of the other side of the mixing chamber (e.g. 0.4 mm high)

The inlets will typically be located such that the direction of flow of the first solution and second solution into the mixing chamber is substantially parallel (e.g. within 15 degrees, such as within 10 degrees, in particular within 5 degrees), such as parallel, to the general direction of flow through the mixing chamber.

The microfluidic device will have at least one outlet from the mixing chamber for recovery of the mixed material. The device may have a plurality of outlets from the mixing chamber for recovery of the mixed material, such as two or three outlets, which are later combined. Suitably the device will have a single outlet from the mixing chamber for recovery of the mixed material.

The cross-section of the outlets may be of any shape, though is typically symmetrical. The cross-section may be rectangular (such as square), typically having an area of 0.2-1 $mm^2$, such as 0.3-0.6 $mm^2$, for example 0.4-0.5 $mm^2$. In other examples the outlet may be of circular cross-section (e.g. having a diameter of 0.5-1 mm, such as 0.6-0.8 mm, for example 0.75 mm).

The total cross-sectional area of all outlets will suitably be less than 70% of the cross-sectional area of the mixing chamber, such as less than 60% and especially less than 50%.

The mixing chamber should be of adequate length to allow for mixing to be substantially complete by the time liquid reaches the outlet(s). Typically, the chamber will be 1-10 cm in length, such as 1.5-5 cm, especially 1.8-4 cm, in particular 2-3 cm, for example 2.5 cm.

In one embodiment the device comprises a mixing chamber which is rectangular in cross-section, having a cross-sectional area of 0.2-3.2 $mm^2$ (e.g. 0.6-1.0 $mm^2$), a long side of 1.4-3.2 mm (e.g. 1.6-2.4 mm), a short side of 0.1-1.2 mm (e.g. 0.32-0.48 mm), one inlet for the first solution and two inlets for the second solution which are symmetrically disposed at the proximal end of the mixing chamber, a mixing chamber length of 1.5-5 cm (e.g. 2-3 cm) and an outlet located at the distal end of the mixing chamber. Suitably the inlets are 0.16-0.24 mm wide and span the full length of the other side of the mixing chamber.

The microfluidic device may be formed from any suitable material, namely one which is tolerant of the components used in the first solution and second solution and which is amenable to manufacture. Suitable materials include silicon and glass. Stainless steel is another suitable material. Devices may be prepared from such materials by etching, e.g. silicon devices may be prepared by Deep Reactive Ion Etching (DRIE or plasma etching) and glass devices may be prepared by wet etching (HF etching). Chosen materials may be subjected to surface treatment to improve the characteristics of the surface.

To achieve a batch run duration which is a manageable time period (e.g. 240 minutes or less, especially 120 minutes or less) it is necessary for the system to achieve a sufficient level of productivity. Additionally, to aid batch to batch consistency by reducing the impact of startup and shutdown effects it is necessary for the run time to be of adequate length (e.g. at least 30 minutes, especially at least 60 minutes).

Microfluidic Device Scale-Up

In order to facilitate production of liposomal adjuvant on an industrial scale (e.g. a scale of at least 0.5 g of phosphatidylcholine lipid per minute, such as at least 1 g per minute, in particular at least 2 g per minute and especially at least 4 g per minute, such as a scale of at least 0.5 g of DOPC per minute, such as at least 1 g per minute, in particular at least 2 g per minute and especially at least 4 g per minute), large mixing chambers may be used or plurality of mixing chambers may be operated in parallel. For example, 2 or more mixing chambers, in particular 4 or more, especially 8 or more, such as 16 or more (e.g. 16). The plurality of mixing chambers operated in parallel may be 128 or fewer, such as 64 or fewer, in particular 32 or fewer. Consequently, in some embodiments the plurality of mixing chambers is 2-128, such as 4-64, for example 8-32.

In some circumstances each mixing chamber from the plurality of mixing chambers may be operated independently, with provision of the first solution and second solution to the mixing chamber by independent pumps (i.e. each pump not concurrently providing solution to any other mixing chamber). The first solution and/or second solution may be stored in independent containers (i.e. containers not concurrently providing first solution and/or second solution to more than one mixing chamber), or first solution and/or second solution may be stored in a container for use in more than one mixing chamber (such as all mixing chambers). Mixed material from each mixing chamber may be recovered individually and stored/processed, optionally being combined at a later stage, or may be combined (e.g. from all mixing chambers) before further processing and/or storage.

Conveniently all mixing chambers in the plurality of mixing chambers are supplied by the same pumps and mixed material from all mixing chambers is collected before further processing and/or storage. Suitably the all mixing chambers and fluid flow within all mixing chambers are substantially the same, such that material obtained from each mixing chamber is substantially the same. Desirably the flow rates measured in each mixing chamber vary by less than 5% from the desired flow rate.

Optimally the mixing chambers, inlets and outlets, supply of first solution, second solution and collection of mixed material of multiple mixing chambers are configured such that in operation they perform substantially identically.

Each mixing chamber from the plurality of mixing chambers may be configured as an individual chip or for convenience a number of mixing chambers may be combined in a single chip (e.g. containing 8 mixing chambers). A number of such chips can be used in parallel to provide the plurality of chambers (e.g. two chips each of which contains 8 mixing chambers to provide a total of 16 mixing chambers to be operated in parallel).

Suitably the plurality of mixing chambers is capable of producing mixed material at a total rate of 50-2000 ml/min, such as 100-1000 ml/min, in particular 200-500 ml/min.

Microfluidic devices described herein are one aspect of the present invention.

First Solution

The first solution (the 'organic' phase) comprises solvent, phosphatidylcholine lipid and a sterol. Suitably the first solution comprises a solvent, DOPC and a sterol.

The solvent should solubilise the phosphatidylcholine lipid (such as DOPC), sterol and any other component present to provide the first solution as a single phase. Furthermore, the solvent should be miscible with the aqueous solution, such that mixing of the first solution and second solution results in a single liquid phase which comprises a suspension of liposomes.

The solvent will be an organic solvent or a single phase mixture comprising at least one organic solvent.

The solvent may comprise a short chain organic alcohol, such as ethanol and/or isopropanol.

Suitably, the solvent will comprise ethanol, such as at a concentration of between 70-90% v/v, more suitably between 75-85% v/v, or between 78-82% v/v.

Suitably, the solvent will comprise isopropanol, such as at a concentration of between 10-30% v/v, more suitably between 15-25% v/v, or between 18-22% v/v.

Suitably, the solvent will consist essentially of ethanol at a concentration of between 70-90% v/v and isopropanol at a concentration of between 10-30% v/v, such as ethanol at a concentration of between 75-85% v/v and isopropanol at a concentration of between 15-25% v/v, especially ethanol at a concentration of between 78-82% v/v and isopropanol at a concentration of between 18-22% v/v, in particular ethanol at a concentration of 80% v/v and isopropanol at a concentration of 20% v/v. At higher ethanol concentrations, such as above 90% v/v ethanol, the solubilising capacity of the solvent is limited (which ultimately constrains system capacity). At lower ethanol concentrations, such as below 70% v/v ethanol, the process may be more sensitive to operating parameters, such as temperature.

As mentioned, the first solution will comprise phosphatidylcholine lipid. The phosphatidylcholine lipid will contain unbranched acyl chains having 12-20 carbon atoms, optionally with one double bond, of particular interest are those with acyl chains having 14-18 carbon atoms, optionally with one double bond. Typically, each of the two acyl chains in a lipid molecule are identical. Particular phosphatidylcholine lipids of interest include: the saturated phosphatidylcholine lipids—dilauroyl phosphatidylcholine (DLPC), dimyristoyl phosphatidylcholine (DMPC), dipalmitoyl phosphatidylcholine (DPPC), distearoyl phosphatidylcholine (DSPC) and diarachidoyl phosphatidylcholine (DAPC); and unsaturated phosphatidylcholine lipids dipalmitoleoyl phosphatidylcholine and dioleoyl phosphatidylcholine (DOPC); and mixtures thereof. Suitably the phosphatidylcholine lipid is substantially purified from other lipids. Typically the phosphatidylcholine lipid is at least 80% pure, such as at least 90% pure, especially at least 95% pure, in particular 98% pure, for example at least 99% or even at least 99.8% pure.

The invention therefore provides a solution comprising a solvent and 100-170 mg/ml lipid, wherein the solvent comprises 70-90% v/v ethanol and 10-30% v/v isopropyl alcohol. Suitably the lipid is phosphatidylcholine lipid, therefore suitably the solution provided is the first solution.

As mentioned, the first solution suitably comprises DOPC (dioleoyl phosphatidylcholine). Suitably the DOPC is substantially purified from other lipids, both of other acyl chain types and other headgroup types. Typically the DOPC is at least 90% pure, such as at least 95% pure, especially at least 98% pure, in particular 99% pure, for example at least 99.8% pure.

Suitably the first solution comprises 100-170 mg/ml DOPC, such as 100-160 mg/ml DOPC, especially 120-160 mg/ml. The first solution may comprise 120-150 mg/ml DOPC, such as 120-140 mg/ml DOPC. In particular, the first solution may comprise around 130 mg/ml DOPC (e.g. 125-135 mg/ml DOPC, especially 130 mg/ml DOPC).

The sterol will typically be cholesterol. Cholesterol is disclosed in the Merck Index, 13th Edn., page 381, as a naturally occurring sterol found in animal fat. Cholesterol has the formula ($C_{27}H_{46}O$) and is also known as (3β)-cholest-5-en-3-ol.

Suitably the first solution comprises 20-50 mg/ml sterol (e.g. cholesterol), such as 25-40 mg/ml, especially around 32.5 mg/ml (e.g. 30-35 mg/ml, in particular 32.5 mg/ml).

Suitably the dry weight of the first solution is 100-250 mg/ml, such as 140-220 mg/ml, especially 150-220 mg/ml.

The invention therefore provides a solution comprising a solvent and 100-170 mg/ml lipid, wherein the solvent comprises 70-90% v/v ethanol and 10-30% v/v isopropyl alcohol. Suitably the lipid is DOPC, therefore suitably the solution provided is the first solution.

Lipids of use in the present invention will typically be membrane forming lipids. Membrane forming lipids comprise a diverse range of structures including phospholipids (for example phosphatidyl choline, phosphatidyl ethanolamine, phosphatidyl glycerol, phosphatidyl inositol and phosphatidyl serine), ceramides and sphingomyelins. Membrane forming lipids typically have a polar head group (which in a membrane aligns towards the aqueous phase) and one or more (e.g. two) hydrophobic tail groups (which in a membrane associate to form a hydrophobic core). The hydrophobic tail groups will typically be in the form of acyl esters, which may vary both in their length (for example from 8 to 26 carbon atoms) and their degree of unsaturation (for example one, two or three double bonds).

Lipids of use in the present invention may be of natural or synthetic origin, and may be a single pure component (e.g. 90% pure, especially 95% pure and suitably 99% pure on a weight basis), a single class of lipid components (for example a mixture of phosphatidyl cholines, or alternatively, a mixture of lipids with a conserved acyl chain type) or may be a mixture of many different lipid types.

In one embodiment of the invention the lipid is a single pure component.

Pure lipids are generally of synthetic or semi-synthetic origin. Examples of pure lipids of use in the present invention include phosphatidyl cholines (for example, DLPC, DMPC, DPPC, DSPC and DOPC; in particular DLPC, DMPC, DPPC and DOPC; especially DOPC) and phosphatidyl glycerols (for example DPPG), suitably phosphatidyl cholines. The use of pure lipids is desirable due to their defined composition, however, they are generally more expensive.

In one embodiment of the invention the lipid is a mixture of components.

Mixtures of lipids of use in the present invention may be of natural origin, obtained by extraction and purification by means known to those skilled in the art. Lipid mixtures of natural origin are generally significantly cheaper than pure synthetic lipids. Naturally derived lipids include lipid extracts from egg or soy, which extracts will generally contain lipids with a mixture of acyl chain lengths, degrees of unsaturation and headgroup types. Lipid extracts of plant origin may typically be expected to demonstrate higher levels of unsaturation than those of animal origin. It should be noted that, due to variation in the source, the composition of lipid extracts may vary from batch to batch.

In one embodiment of the invention the lipid is a lipid extract containing at least 50%, especially at least 75% and suitably at least 90% by weight of phospholipids of a single headgroup type (e.g. phosphatidyl cholines). In a second embodiment of the invention particular lipid extracts may be preferred due to their relatively cheap cost. In a third embodiment of the invention the lipid is a lipid mixture having a conserved acyl chain length (e.g. at least 50%, especially at least 75% and suitably at least 90% by weight), for example 12 (e.g. lauryl), 14 (e.g. myristyl), 16 (e.g. palmityl) or 18 (e.g. stearyl or oleoyl) carbons atoms in length.

Suitably, a lipid extract of use in the present invention will comprise at least 50% phospholipids by weight (for example, phosphatidyl cholines and phosphatidyl ethanolamines), especially at least 55% phospholipids by weight, in particular at least 60% phospholipids by weight (such as 75% or 90%).

Lipid mixtures may also be prepared by the combination of pure lipids, or by the combination of one lipid extract with either other lipid extracts or with pure lipids.

The ratio of lipid (e.g. DOPC) to sterol is usually 3:1 to 5:1 w/w, such as 3.5:1 to 4.5:1 w/w.

In some embodiments the first solution consists essentially of a solvent and 100-160 mg/ml lipid and 30-40 mg/ml cholesterol wherein the solvent comprises 70-90% v/v ethanol and 10-30% v/v isopropyl alcohol. Desirably the lipid is phosphatidylcholine. Suitably the lipid is DOPC.

In order to prepare liposomal adjuvants comprising a TLR4 agonist, the TLR4 agonist may optionally be included in the first solution. The first solution may contain 1-25 mg/ml of the TLR4 agonist, such as 2-16 mg/ml, especially 3-12 mg/ml and in particular 4-10 mg/ml (e.g. around 6.5, such as 5.5-7.5 mg/ml, especially 6.5 mg/ml).

The present invention also provides a method for the preparation of a solution comprising a solvent, lipid, cholesterol and TLR4 agonist, said method comprising the steps:
(i) preparing a suspension of the TLR4 agonist in at least a portion of the solvent;
(ii) combining the suspended TLR4 agonist with the phosphatidylcholine lipid and cholesterol;
(iii) adding further solvent;
(iv) mixing.

The present invention also provides a method for the preparation of a solution comprising a solvent, lipid, cholesterol and TLR4 agonist, said method comprising the steps:
(i) preparing a suspension of the TLR4 agonist in at least a portion of the solvent;
(ii) combining the suspended TLR4 agonist with the DOPC and cholesterol;
(iii) adding further solvent;
(iv) mixing.

Suitably the mixing is undertaken at a temperature of 30-50° C., especially 35-45, such as 40° C. Suitably the at least a portion of the solvent is at least 25% of the solvent, especially at least 35% and in particular at least 45%. Suitably the at least a portion is 90% of the solvent or less, such as 80% or less, especially 70% or less and in particular 60% or less. In some examples the at least a portion is 35-70% of the solvent, such as 45-60%.

Suitably the further solvent is any remaining solvent, although it may be a portion of the remaining solvent with additional solvent added later. Consequently, the present invention also provides a method for the preparation of a solution comprising a solvent, lipid, cholesterol and TLR4 agonist, said method comprising the steps:
(i) preparing a suspension of the TLR4 agonist in at least a portion of the solvent;
(ii) combining the suspended TLR4 agonist with the phosphatidylcholine lipid and cholesterol;
(iii) adding further solvent;
(iv) mixing;
(v) adding additional solvent.

Suitably the further solvent is any remaining solvent, although it may be a portion of the remaining solvent with additional solvent added later. Consequently, the present invention also provides a method for the preparation of a solution comprising a solvent, lipid, cholesterol and TLR4 agonist, said method comprising the steps:
(i) preparing a suspension of the TLR4 agonist in at least a portion of the solvent;
(ii) combining the suspended TLR4 agonist with the DOPC and cholesterol;
(iii) adding further solvent;
(iv) mixing;
(v) adding additional solvent.

The additional solvent may be 0-30% of the solvent, such as 0-20%.

The solution arising from any of the above mentioned methods may subsequently be filtered to remove any particulate material prior to use in the microfluidics apparatus.

Other features of the method may be as described for the first solution, e.g. the solution comprises 100-160 mg/ml lipid and 30-40 mg/ml cholesterol and wherein the solvent comprises 70-90% v/v ethanol and 10-30% v/v isopropyl alcohol. Desirably the lipid is phosphatidylcholine. Suitably the lipid is DOPC. Suitably the solution comprises 4-10 mg/ml TLR4 agonist, in particular 3D-MPL.

Suitably the invention provides a solution consisting essentially of 100-160 mg/ml lipid and 30-40 mg/ml cholesterol and wherein the solvent comprises 70-90% v/v ethanol and 10-30% v/v isopropyl alcohol. Desirably the lipid is phosphatidylcholine, more suitably the lipid is DOPC. Suitably the solution comprises 4-10 mg/ml TLR4 agonist, in particular 3D-MPL Second Solution The second solution (the 'aqueous' phase) comprises water and in some methods may comprise a saponin.

The second solution acts as a counter solvent, causing the formation of liposomes on mixing with the first solution. The faster the precipitation of components from the first solution, typically the smaller the liposomes obtained.

The second solution will be substantially aqueous and will comprise at least 90% water v/v, such as at least 95% water, especially at least 98% water and in particular 100% water.

When present in the second solution, suitably the saponin is present at a concentration of 0.05-25 mg/ml, such as 0.2-10 mg/ml, especially 0.5-5 mg/ml and in particular 0.8-3 mg/ml (e.g. about 1.625 mg/ml, such as 1.2-2 mg/ml, especially 1.625 mg/ml).

When the saponin is not present in the second solution, suitably the second solution consists essentially of (such as consists of) water.

When the saponin is present in the second solution, suitably the second solution consists essentially of (such as consists of) water and saponin, for example the second solution may by saponin (such as QS-21) in water for injection.

The ionic strength of the second solution will suitably be 150 nM or lower, such as 100 nM or lower, in particular 80 nM or lower, especially 60 nM or lower, for example 40 nM or lower.

Conductivity may be a convenient surrogate for the ionic strength of an aqueous solution. The conductivity of the second solution will suitably be 12 mS/cm or lower, for example 10 mS/cm or lower, 8 mS/cm or lower, 6 mS/cm or lower, or 4 mS/cm or lower.

Suitably, the second solution consists essentially of aqueous saponin.

Microfluidic Operation

Optimal operating conditions will depend on the precise configuration of the device and the desired characteristics of the product.

Suitably, the total flow rate into the mixing chamber is 15-30 ml/min/mm$^2$ of mixing chamber cross-section, such as 16-28 ml/min/mm$^2$, especially 17.5-25 ml/min/mm$^2$ and in particular 19-21 (e.g. 20 ml/min/mm$^2$.

Suitably the ratio of flow rates for the first and second solutions will be in the range of 1:2 to 1:6, such as 1:3 to 1:5, especially 1:3.5 to 1:4.5 and in particular 1:4. High levels of solvent in mixed material may impact the stability of liposomes so ratio of flow rates which result in high solvent concentrations are desirably avoided—solvent concentrations of 50% result from a ratio of 1:1, 33% for 1:2, 25% for ratio 1:3, 20% for ratio 1:4 and 16.6% for ratio 1:5. Low flow rate of the first solution reduces system productivity. Ratios of flow rates which result in relatively large volumes of mixed material are less desirable due to the safety protocols associated with the handling and use of solvent containing compositions which exceed certain thresholds (e.g. 50 L).

Suitably, the flow rate of the first solution into the mixing chamber is in the range of 2-7.5 ml/min/mm$^2$ of mixing chamber cross-section, such as 2.5-7 ml/min/mm$^2$, especially 3-6.5 ml/min/mm$^2$ and in particular 3.5-6 (e.g. 5) ml/min/mm$^2$.

Suitably, the flow rate of the second solution into the mixing chamber is in the range of 11-25 ml/min/mm$^2$ of mixing chamber cross-section, such as 12-20 ml/min/mm$^2$, especially 14-18 ml/min/mm$^2$ and in particular 15-17 (e.g. 16) ml/min/mm$^2$.

The first solution and second solution will typically be provided at a temperature in the region of 10-30° C., such as 15-25° C., in particular 18-22° C. especially 20° C.), and may be at the same or different temperatures, suitably at the same temperature and especially at 20° C.

The mixing chamber may be maintained at a temperature in the region of 10-30° C., such as 15-25° C., in particular 18-22° C., especially 20° C. Dependent on the design of the device and environmental conditions it may only be necessary to actively control the temperature of the first solution and second solution, and not to actively control the mixing chamber temperature. The mixing of the first solution and second solution may be mildly exothermic. Lower operating temperatures result in the formation of smaller liposomes.

The microfluidic device may be operated within a controlled temperature environment, e.g. where the temperature is maintained in the range of 10-30° C., such as 15-25° C., in particular about 20° C. (such as 18-22° C., in particular 20° C.).

The operating pressure of the system need not be controlled.

Suitably, the maximum Reynolds number within the mixing chamber is 2100, in particular 1800, such as 1500, especially 1000, for example 500. The maximum Reynolds number within the mixing chamber is suitably within the range of 25 to 1500, more suitably between 50 to 500, in particular 75 to 300 and especially 100 to 200. Methods for calculating the Reynolds number are known to those skilled in the art and are illustrated in the examples herein.

Liposomes

Upon mixing of the first solution and second solution, liposomes will form.

The term 'liposome' is well known in the art and defines a general category of vesicles which comprise one or more lipid bilayers surrounding an aqueous space. Liposomes thus consist of one or more lipid and/or phospholipid bilayers and can contain other molecules, such as proteins or carbohydrates, in their structure. Because both lipid and aqueous phases are present, liposomes can encapsulate or entrap water-soluble material, lipid-soluble material, and/or amphiphilic compounds.

Liposome size may vary from 30 nm to several um depending on the phospholipid composition and the method used for their preparation.

The liposomes of the present invention contain phosphatidylcholine lipid, or, consist essentially of phosphatidylcholine lipid and sterol (with saponin and TLR4 agonist as applicable).

Suitably the liposomes of the present invention contain DOPC, or, consist essentially of DOPC and sterol (with saponin and TLR4 agonist as applicable).

In the present invention, the liposome size will be in the range of 50 nm to 200 nm, especially 60 nm to 180 nm, such as 70-165 nm. Optimally, the liposomes should be stable and have a diameter of ~100 nm to allow convenient sterilization by filtration.

Structural integrity of the liposomes may be assessed by methods such as dynamic light scattering (DLS) measuring the size (Z-average diameter, Zav) and polydispersity of the liposomes, or, by electron microscopy for analysis of the structure of the liposomes. Suitably the average particle size is between 95 and 120 nm, and/or, the polydispersity (Pdl) index is not more than 0.35, in particular not more than 0.3, such as not more than 0.25. In one embodiment the average particle size is between 95 and 120 nm, and/or, the polydispersity (Pdl) index is not more than 0.2.

In some circumstances the presence of solvents and certain additional components can impact the liposome size. Consequently, the liposome size is suitably measured after solvent removal and the incorporation of any additional components.

Removing the Solvent

The recovered mixed material will comprise liposomes in water and solvent. Such material is a liposomal concentrate of use in preparing a liposomal adjuvant, said liposomal concentrate comprising water, a solvent, phosphatidylcholine lipid, saponin and cholesterol, such as comprising water, a solvent, DOPC, saponin and cholesterol. The recovered material may be stored for later use or may be further processed to remove some or all of the solvent.

To facilitate use of the liposomes in an adjuvant it is desirable to remove substantially all organic solvent (e.g. leaving at least 98% water w/w, such as at least 99% water, especially at least 99.5% water, in particular at least 99.9% water such as at least 99.99%).

Suitably the residual organic solvent is at a level which equates to less than 150 ug per human dose, such as less than 100 ug per human dose, such as less than 50 ug per human dose and especially less than 20 ug per human dose (e.g. 10 ug or less per human dose). Desirably the residual organic solvent is at a level which is compliant with International Council For Harmonisation Of Technical Requirements For Pharmaceuticals For Human Use Guideline For Residual Solvents Q3C(R6).

Solvent removal may be performed by a range of methods, which may be used individually or in combination. Suitable methods include ultrafiltration and dialysis, especially diafiltration.

The removal of at least a portion of the solvent, such as substantially all of the solvent, can be performed by dialysis. Dialysis is the use of semi-permeable containment vessel that is selectively permeable such that solvent will pass through the semi-permeable portion of the vessel and liposomes (also saponin and TLR4 agonist if present) will be retained when recovered material is introduced to the semi-permeable containment vessel. For example, the semi-permeable containment vessel used can include a single semi-permeable membrane and solvent removal can be achieved by immersing the semi-permeable containment vessel comprising the recovered material in an exchange medium and allowing the liquids separated by the membrane to reach equilibrium by diffusion. Dialysis may be undertaken in batch or continuous modes of operation. For example, dialysis can be repeated multiple times with batch replacement of the exchange medium to achieve a desired level of solvent removal. Dialysis can also be in a continuous process where the recovered material and/or exchange medium is continuously undergoing replacement. Exemplary dialysis membranes which may be of use in the present methods include 7 kDa membranes.

The removal of at least a portion of the solvent, such as substantially all of the solvent, can be performed by ultrafiltration. Ultrafiltration is the use of a containment vessel including a first compartment and a second compartment separated by a semi-permeable membrane. The recovered material can be placed into the first compartment of the containment vessel which can then be subjected to a positive pressure relative to the second compartment such that liquid is forced across the semi-permeable portion of the containment vessel. Diafiltration is a form of ultrafiltration wherein at least a portion of the remaining liquid can be replaced with an exchange medium by addition of the exchange medium to the first compartment of the vessel. Consequently, as the ultrafiltration progresses, the remaining liquid will tend towards the composition of the exchange medium. Diafiltration can be undertaken in a range of ways—continuous (also known as constant volume) wherein exchange medium is added at a comparable rate to liquid filtration over the membrane; discontinuous, wherein the volume of the remaining liquid varies and exchange medium is added in a discontinuous manner (e.g. by initial dilution and subsequent concentration to original volume or by initial concentration and subsequent dilution to original volume or the like). The optimal operating mode may depend on a number of factors including: 1) initial sample volume, concentration and viscosity 2) required final sample concentration 3) stability of sample at various concentrations 4) volume of buffer required for diafiltration 5) total processing time 6) reservoir size available 7) economics. Exemplary diafiltration membranes include Hydrosart 30 kD.

The exchange medium used during solvent removal need not correspond to the medium of the final liposomal adjuvant, for convenience the exchange medium is suitably the desired final liposomal adjuvant medium or a concentrate thereof e.g. phosphate buffered saline or another buffered composition as desired.

In certain methods, the saponin may be added to the recovered mixed material before removal of the solvent. In other methods the saponin may be added after removal of the solvent.

Saponins

A suitable saponin for use in the present invention is Quil A and its derivatives. Quil A is a saponin preparation isolated from the South American tree *Quillaja saponaria* Molina and was first described as having adjuvant activity by Dalsgaard et al. in 1974 ("Saponin adjuvants", Archiv. für die gesamte Virusforschung, Vol. 44, Springer Verlag, Berlin, p 243-254). Purified fractions of Quil A have been isolated by HPLC which retain adjuvant activity without the toxicity associated with Quil A (see, for example, EP0362278). Fractions of general interest include QS7, QS17, QS18 and QS-21, for example QS7 and QS-21 (also known as QA7 and QA21). QS-21 is a saponin of particular interest.

In certain embodiments of the present invention, the saponin is a derivative of *Quillaja saponaria* Molina quil A, suitably an immunologically active fraction of Quil A, such as QS7, QS17, QS18 or QS-21, in particular QS-21.

Typically the saponin, such as Quil A and in particular QS-21, is at least 90% pure, such as at least 95% pure, especially at least 98% pure, in particular 99% pure.

A beneficial feature of the present invention is that the saponin is presented in a less reactogenic composition where it is quenched with an exogenous sterol, such as cholesterol.

In methods where the saponin is added after mixing of the first and second solutions, the amount of saponin will typically be equivalent to the amounts which would be used if added earlier.

TLR4 Agonists

A suitable example of a TLR4 agonist is a lipopolysaccharide, suitably a non-toxic derivative of lipid A, particularly a monophosphoryl lipid A and more particularly 3-de-O-acylated monophosphoryl lipid A (3D-MPL).

3D-MPL is sold under the name 'MPL' by GlaxoSmithKline Biologicals N.A. and is referred throughout the document as 3D-MPL. See, for example, U.S. Pat. Nos. 4,436,727; 4,877,611; 4,866,034 and 4,912,094. 3D-MPL can be produced according to the methods described in GB 2 220 211 A. Chemically it is a mixture of 3-deacylated monophosphoryl lipid A with 4, 5 or 6 acylated chains. In the context of the present invention small particle 3D-MPL may be used to prepare the aqueous adjuvant composition. Small particle 3D-MPL has a particle size such that it may be sterile-filtered through a 0.22 um filter. Such preparations are described in WO94/21292. Suitably, powdered 3D-MPL is used to prepare aqueous adjuvant compositions of use in the present invention.

Other TLR4 agonists which can be used are alkyl glucosaminide phosphates (AGPs) such as those described in WO98/50399 or U.S. Pat. No. 6,303,347 (processes for preparation of AGPs are also described). Some AGPs are TLR4 agonists, and some are TLR4 antagonists.

Other TLR4 agonists which may be of use in the present invention include Glucopyranosyl Lipid Adjuvant (GLA) such as described in WO2008/153541 or WO2009/143457 or the literature articles Coler R N et al. (2011) Development and Characterization of Synthetic Glucopyranosyl Lipid Adjuvant System as a Vaccine Adjuvant. PLoS ONE 6(1): e16333. doi:10.1371/journal.pone.0016333 and Arias M A et al. (2012) Glucopyranosyl Lipid Adjuvant (GLA), a Synthetic TLR4 Agonist, Promotes Potent Systemic and Mucosal Responses to Intranasal Immunization with HIVgp140. PLoS ONE 7(7): e41144. doi:10.1371/journal.pone.0041144. WO2008/153541 or WO2009/143457 are incorporated herein by reference for the purpose of defining TLR4 agonists which may be of use in the present invention.

Typically the TLR4 agonist, such as the lipopolysaccharide and in particular 3D-MPL, is at least 90% pure, such as at least 95% pure, especially at least 98% pure, in particular 99% pure.

In certain methods, the TLR4 agonist may be added to the recovered mixed material before removal of the solvent. In other methods the TLR4 agonist may be added after removal of the solvent (in such circumstances the amount of TLR4 will typically be equivalent to the amounts which would be used if added earlier).

Consequently, there is provided a method of manufacturing a liposomal adjuvant comprising a saponin and a TLR4 agonist using a microfluidic device, comprising the following steps:
  (a) mixing in the device a first solution comprising a solvent, phosphatidylcholine lipid, sterol and the TLR4 agonist, and a second solution comprising water and the saponin; and
  (b) removing the solvent.

Also provided is a method of manufacturing a liposomal adjuvant comprising a saponin and a TLR4 agonist using a microfluidic device, comprising the following steps:
  (a) mixing in the device a first solution comprising a solvent, phosphatidylcholine lipid and a sterol, and a second solution comprising water;
  (b) adding the saponin;
  (c) adding the TLR 4 agonist; and
  (d) removing the solvent;
wherein steps (b) and (c) may be in either order, or may be performed in a single step.

Further provided is a method of manufacturing a liposomal adjuvant comprising a saponin and a TLR4 agonist using a microfluidic device, comprising the following steps:
  (a) mixing in the device a first solution comprising a solvent, phosphatidylcholine lipid and a sterol, and a second solution comprising water;
  (b) removing the solvent;
  (c) adding the saponin; and
  (d) adding the TLR 4 agonist;
wherein steps (c) and (d) may be in either order, or may be performed in a single step.

Additionally, provided is a method of manufacturing a liposomal adjuvant comprising a saponin and a TLR4 agonist using a microfluidic device, comprising the following steps:
  (a) mixing in the device a first solution comprising a solvent, phosphatidylcholine lipid and a sterol, and a second solution comprising water;
  (b) adding the saponin;
  (c) removing the solvent; and
  (d) adding the TLR 4 agonist.

Further provided is a method of manufacturing a liposomal adjuvant comprising a saponin and a TLR4 agonist using a microfluidic device, comprising the following steps:
  (a) mixing in the device a first solution comprising a solvent, phosphatidylcholine lipid and a sterol, and a second solution comprising water;
  (b) adding the TLR 4 agonist;
  (c) removing the solvent; and
  (d) adding the saponin.

There is also provided a method of manufacturing a liposomal concentrate of use in preparing a liposomal adjuvant comprising a saponin and a TLR4 agonist using a microfluidic device, comprising the step of mixing in the device a first solution comprising a solvent, phosphatidylcholine lipid, sterol and the TLR4 agonist, and a second solution comprising water and the saponin.

Also provided is a method of manufacturing a liposomal concentrate of use in preparing a liposomal adjuvant comprising a saponin and a TLR4 agonist using a microfluidic device, comprising the following steps:
  (a) mixing in the device a first solution comprising a solvent, phosphatidylcholine lipid and a sterol, and a second solution comprising water;
  (b) adding the saponin; and
  (c) adding the TLR 4 agonist;
wherein steps (b) and (c) may be in either order, or may be performed in a single step.

There is also provided a method of manufacturing a liposomal adjuvant comprising a saponin and a TLR4 agonist using a microfluidic device, comprising the following steps:
  (a) mixing in the device a first solution comprising a solvent, DOPC, sterol and the TLR4 agonist, and a second solution comprising water and the saponin; and
  (b) removing the solvent.

Also provided is a method of manufacturing a liposomal adjuvant comprising a saponin and a TLR4 agonist using a microfluidic device, comprising the following steps:
(a) mixing in the device a first solution comprising a solvent, DOPC and a sterol, and a second solution comprising water;
(b) adding the saponin;
(c) adding the TLR 4 agonist; and
(d) removing the solvent;
wherein steps (b) and (c) may be in either order, or may be performed in a single step.

Further provided is a method of manufacturing a liposomal adjuvant comprising a saponin and a TLR4 agonist using a microfluidic device, comprising the following steps:
(a) mixing in the device a first solution comprising a solvent, DOPC and a sterol, and a second solution comprising water;
(b) removing the solvent;
(c) adding the saponin; and
(d) adding the TLR 4 agonist;
wherein steps (c) and (d) may be in either order, or may be performed in a single step.

Additionally provided is a method of manufacturing a liposomal adjuvant comprising a saponin and a TLR4 agonist using a microfluidic device, comprising the following steps:
(a) mixing in the device a first solution comprising a solvent, DOPC and a sterol, and a second solution comprising water;
(b) adding the saponin;
(c) removing the solvent; and
(d) adding the TLR 4 agonist.

Further provided is a method of manufacturing a liposomal adjuvant comprising a saponin and a TLR4 agonist using a microfluidic device, comprising the following steps:
(a) mixing in the device a first solution comprising a solvent, DOPC and a sterol, and a second solution comprising water;
(b) adding the TLR4 agonist;
(c) removing the solvent; and
(d) adding the saponin.

There is also provided a method of manufacturing a liposomal concentrate of use in preparing a liposomal adjuvant comprising a saponin and a TLR4 agonist using a microfluidic device, comprising the step of mixing in the device a first solution comprising a solvent, DOPC, sterol and the TLR4 agonist, and a second solution comprising water and the saponin.

Also provided is a method of manufacturing a liposomal concentrate of use in preparing a liposomal adjuvant comprising a saponin and a TLR4 agonist using a microfluidic device, comprising the following steps:
(a) mixing in the device a first solution comprising a solvent, DOPC and a sterol, and a second solution comprising water;
(b) adding the saponin; and
(c) adding the TLR 4 agonist;
wherein steps (b) and (c) may be in either order, or may be performed in a single step.

By the term 'performed in a single step' as used herein is intended contemporaneously or simultaneously.

The liposome containing solution obtainable by (such as obtained by) mixing of the first solution and the second solution according to any of the methods described herein forms a further aspect of the invention.

Further Excipients

The liposomal adjuvant resulting from the claimed methods may be further modified. For example, it may be diluted to achieve a particular concentration of components as desired for later uses and/or additional components added. Such steps can be taken at a number of stages in the methods: prior to solvent removal, during solvent removal (e.g. by way of the exchange medium) or after solvent removal.

In a further embodiment, a buffer is added to the composition. The pH of a liquid preparation is adjusted in view of the components of the composition and necessary suitability for administration to the subject. Suitably, the pH of a liquid mixture is at least 4, at least 5, at least 5.5, at least 5.8, at least 6. The pH of the liquid mixture may be less than 9, less than 8, less than 7.5 or less than 7. In other embodiments, pH of the liquid mixture is between 4 and 9, between 5 and 8, such as between 5.5 and 8. Consequently, the pH will suitably be between 6-9, such as 6.5-8.5. In a particularly preferred embodiment the pH is between 5.8 and 6.4.

An appropriate buffer may be selected from acetate, citrate, histidine, maleate, phosphate, succinate, tartrate and TRIS. In one embodiment, the buffer is a phosphate buffer such as $Na/Na_2PO_4$, $Na/K_2PO_4$ or $K/K_2PO_4$.

The buffer can be present in the liquid mixture in an amount of at least 6 mM, at least 10 mM or at least 40 mM. The buffer can be present in the liquid mixture in an amount of less than 100 mM, less than 60 mM or less than 40 mM.

It is well known that for parenteral administration solutions should have a pharmaceutically acceptable osmolality to avoid cell distortion or lysis. A pharmaceutically acceptable osmolality will generally mean that solutions will have an osmolality which is approximately isotonic or mildly hypertonic. Suitably the compositions of the present invention when reconstituted will have an osmolality in the range of 250 to 750 mOsm/kg, for example, the osmolality may be in the range of 250 to 550 mOsm/kg, such as in the range of 280 to 500 mOsm/kg. In a particularly preferred embodiment the osmolality may be in the range of 280 to 310 mOsm/kg.

Osmolality may be measured according to techniques known in the art, such as by the use of a commercially available osmometer, for example the Advanced™ Model 2020 available from Advanced Instruments Inc. (USA).

An "isotonicity agent" is a compound that is physiologically tolerated and imparts a suitable tonicity to a formulation to prevent the net flow of water across cell membranes that are in contact with the formulation. In some embodiments, the isotonicity agent used for the composition is a salt (or mixtures of salts), conveniently the salt is sodium chloride, suitably at a concentration of approximately 150 nM. In other embodiments, however, the composition comprises a non-ionic isotonicity agent and the concentration of sodium chloride in the composition is less than 100 mM, such as less than 80 mM, e.g. less than 50 mM, such as less 40 mM, less than 30 mM and especially less than 20 mM. The ionic strength in the composition may be less than 100 mM, such as less than 80 mM, e.g. less than 50 mM, such as less 40 mM or less than 30 mM.

In a particular embodiment, the non-ionic isotonicity agent is a polyol, such as sucrose and/or sorbitol. The concentration of sorbitol may e.g. between about 3% and about 15% (w/v), such as between about 4% and about 10% (w/v). Adjuvants comprising an immunologically active saponin fraction and a TLR4 agonist wherein the isotonicity agent is salt or a polyol have been described in WO2012/080369.

Suitably, a human dose volume of between 0.05 ml and 1 ml, such as between 0.1 and 0.5 ml, in particular a dose volume of about 0.5 ml, or 0.7 ml. The volumes of the compositions used may depend on the delivery route and location, with smaller doses being given by the intradermal route. A unit dose container may contain an overage to allow for proper manipulation of materials during administration of the unit dose.

The saponin, such as QS-21, can be used at amounts between 1 and 100 ug per human dose. QS-21 may be used at a level of about 50 ug. Examples of suitable ranges are 40-60 ug, suitably 45-55 ug or 49-51 ug, such as 50 ug. In a further embodiment, the human dose comprises QS-21 at a level of about 25 ug. Examples of lower ranges include 20-30 ug, suitably 22-28 ug or 24-26 ug, such as 25 ug. Human doses intended for children may be reduced compared to those intended for an adult (e.g. reduction by 50%).

The TLR4 agonist such as a lipopolysaccharide, such as 3D-MPL, can be used at amounts between 1 and 100 ug per human dose. 3D-MPL may be used at a level of about 50 ug. Examples of suitable ranges are 40-60 ug, suitably 45-55 ug or 49-51 ug, such as 50 ug. In a further embodiment, the human dose comprises 3D-MPL at a level of about 25 ug. Examples of lower ranges include 20-30 ug, suitably 22-28 ug or 24-26 ug, such as 25 ug. Human doses intended for children may be reduced compared to those intended for an adult (e.g. reduction by 50%).

When both a TLR4 agonist and a saponin are present in the adjuvant, then the weight ratio of TLR4 agonist to saponin is suitably between 1:5 to 5:1, suitably 1:1. For example, where 3D-MPL is present at an amount of 50 ug or 25 ug, then suitably QS-21 may also be present at an amount of 50 ug or 25 ug per human dose.

The ratio of saponin:DOPC will typically be in the order of 1:50 to 1:10 (w/w), suitably between 1:25 to 1:15 (w/w), and preferably 1:22 to 1:18 (w/w), such as 1:20 (w/w).

Antigens

The liposomal adjuvants prepared according to the methods of the present invention may be utilised in conjunction with an immunogen or antigen. In some embodiments a polynucleotide encoding the immunogen or antigen is provided.

The liposomal adjuvant may be administered separately from an immunogen or antigen may be combined, either during manufacturing or extemporaneously, with an immunogen or antigen as an immunogenic composition for combined administration.

Consequently, there is provided a method for the preparation of an immunogenic composition comprising an immunogen or antigen, or a polynucleotide encoding the immunogen or antigen, said method comprising the steps of:
 (i) preparing a liposomal adjuvant according to the methods described herein;
 (ii) mixing the liposomal adjuvant with an immunogen or antigen, or a polynucleotide encoding the immunogen or antigen.

There is also provided the use of a liposomal adjuvant prepared according to the methods described herein in the manufacture of a medicament. Suitably the medicament comprises an immunogen or antigen, or a polynucleotide encoding the immunogen or antigen.

Further provided is a liposomal adjuvant prepared according to the methods described herein for use as a medicament. Suitably the medicament comprises an immunogen or antigen, or a polynucleotide encoding the immunogen or antigen.

By the term immunogen is meant a polypeptide which is capable of eliciting an immune response. Suitably the immunogen is an antigen which comprises at least one B or T cell epitope. The elicited immune response may be an antigen specific B cell response, which produces neutralizing antibodies. The elicited immune response may be an antigen specific T cell response, which may be a systemic and/or local response. The antigen specific T cell response may comprise a CD4+ T cell response, such as a response involving CD4+ T cells expressing a plurality of cytokines, e.g. IFNgamma, TNFalpha and/or IL2. Alternatively, or additionally, the antigen specific T cell response comprises a CD8+ T cell response, such as a response involving CD8+ T cells expressing a plurality of cytokines, e.g., IFNgamma, TNFalpha and/or IL2.

The antigen may be derived (such as obtained from) from a human or non-human pathogen including, e.g., bacteria, fungi, parasitic microorganisms or multicellular parasites which infect human and non-human vertebrates, or from a cancer cell or tumor cell.

In one embodiment the antigen is a recombinant protein, such as a recombinant prokaryotic protein.

In one embodiment, the antigen is derived from *Plasmodium* spp. (such as *Plasmodium falciparum*), *Mycobacterium* spp. (such as *Mycobacterium tuberculosis* (TB)), Varicella Zoster Virus (VZV), human respiratory syncytial virus, Human Immunodeficiency Virus (HIV), *Moraxella* spp. (such as *Moraxella catarrhalis*) or nontypable *Haemophilus influenzae* (ntHi).

The antigen may comprise or consist of preparations derived from parasites that cause malaria such as *Plasmodium falciparum* or *Plasmodium vivax*.

In one embodiment, the antigen may be the *Plasmodium falciparum* circumsporozoite (CS) protein or a variant thereof. A suitable variant of the CS protein may be a variant wherein parts of the CS protein are in the form of a hybrid protein with the surface antigen S from hepatitis B (HBsAg). The CS variant antigen may e.g. be in the form of a hybrid protein comprising substantially all the C-terminal portion of the CS protein, four or more tandem repeats of the CS protein immunodominant region, and HBsAg. The hybrid protein may comprise a sequence which contains at least 160 amino acids and which is substantially homologous to the C-terminal portion of the CS protein, but devoid of the hydrophobic anchor sequence. The CS protein may be devoid of the last 12 amino-acids from the C terminal. Further, it may contain 4 or more e.g. 10 or more Asn-Ala-Asn-Pro tetrapeptide (NANP) repeat motifs.

The hybrid protein for use in the invention may be a protein which comprises a portion of the CS protein of *P. falciparum* substantially as corresponding to amino acids 207-395 of *P. falciparum* clone 3D7, derived from the strain NF54 fused in frame via a linear linker to the N-terminus of HBsAg. The linker may comprise a portion of preS2 from HBsAg. CS constructs suitable for use in the present invention are outlined in WO93/10152, which granted in the US as U.S. Pat. Nos. 5,928,902 and 6,169,171, both of which are incorporated by reference for the purpose of describing suitable proteins for use in the present invention.

A particular hybrid protein for use in the invention is the hybrid protein known as RTS (SEQ ID No. 1, also described in WO2015/150568, WO93/10152 (wherein it is denoted RTS*) and in WO98/05355, which consists of:
- a methionine residue
- three amino acid residues, Met Ala Pro
- a stretch of 189 amino acids representing amino acids 207 to 395 of the CS protein of *P. falciparum* strain 3D7
- an glycine residue
- four amino acid residues, Pro Val Thr Asn, representing the four carboxy terminal residues of the hepatitis B virus (adw serotype) preS2 protein, and
- a stretch of 226 amino acids, encoded by nucleotides 1653 to 2330, and specifying the S protein of hepatitis B virus (adw serotype).

RTS may be in the form of RTS,S mixed particles. RTS,S particles comprise two polypeptides, RTS and S, that may be synthesized simultaneously and spontaneously form composite particulate structures (RTS,S).

The antigen may comprise or consist of preparations derived from *Mycobacterium* spp., such as *Mycobacterium bovis* or *Mycobacterium tuberculosis*, in particular *Mycobacterium tuberculosis*.

Antigens of interest in the field of tuberculosis include Rv1196 and Rv0125. Rv1196 (described, for example, by the name Mtb39a in Dillon et al Infection and Immunity 1999 67(6): 2941-2950) is highly conserved, with 100% sequence identity across H37Rv, C, Haarlem, CDC1551, 94-M4241A, 98-R604INH-RIF-EM, KZN605, KZN1435, KZN4207, KZNR506 strains, the F11 strain having a single point mutation 030K (most other clinical isolates have in excess of 90% identity to H37Rv). Rv0125 (described, for example, by the name Mtb32a in Skeiky et al Infection and Immunity 1999 67(8): 3998-4007) is also highly conserved, with 100% sequence identity across many strains. Full length Rv0125 includes an N-terminal signal sequence which is cleaved to provide the mature protein.

In one embodiment the antigen is derived from Rv1196, such as comprise, such as consist of, a sequence having at least 70% identity to SEQ ID No: 2, such as at least 80%, in particular at least 90%, especially at least 95%, for example at least 98%, such as at least 99%. Typical Rv1196 related antigens will comprise (such as consist of) a derivative of SEQ ID No: 2 having a small number of deletions, insertions and/or substitutions. Examples are those having deletions of up to 5 residues at 0-5 locations, insertions of up to 5 residues at 0-5 five locations and substitution of up to 20 residues. Other derivatives of Rv1196 are those comprising (such as consisting of) a fragment of SEQ ID No: 2 which is at least 200 amino acids in length, such as at least 250 amino acids in length, in particular at least 300 amino acids in length, especially at least 350 amino acids in length.

In one embodiment the antigen is derived from Rv0125, such as comprise, such as consist of, a sequence having at least 70% identity to SEQ ID No: 3, such as at least 80%, in particular at least 90%, especially at least 95%, for example at least 98%, such as at least 99%. Typical Rv0125 related antigens will comprise (such as consist of) a derivative of SEQ ID No: 3 having a small number of deletions, insertions and/or substitutions. Examples are those having deletions of up to 5 residues at 0-5 locations, insertions of up to 5 residues at 0-5 five locations and substitution of up to 20 residues. Other derivatives of Rv0125 are those comprising (such as consisting of) a fragment of SEQ ID No: 3 which is at least 150 amino acids in length, such as at least 200 amino acids in length, in particular at least 250 amino acids in length, especially at least 300 amino acids in length.

Particular derivatives of Rv0125 are those comprising (such as consisting of) the fragment of SEQ ID No: 3 corresponding to residues 1-195 of SEQ ID No: 3. Further immunogenic derivatives of Rv0125 are those comprising (such as consisting of) the fragment of SEQ ID No: 3 corresponding to residues 192-323 of SEQ ID No: 3. Particularly preferred Rv0125 related antigens are derivatives of SEQ ID No: 3 wherein at least one (for example one, two or even all three) of the catalytic triad have been substituted or deleted, such that the protease activity has been reduced and the protein more easily produced—the catalytic serine residue may be deleted or substituted (e.g. substituted with alanine) and/or the catalytic histidine residue may be deleted or substituted and/or substituted the catalytic aspartic acid residue may be deleted or substituted. Especially of interest are derivatives of SEQ ID No: 3 wherein the catalytic serine residue has been substituted (e.g. substituted with alanine). Also of interest are Rv0125 related antigens which comprise, such as consist of, a sequence having at least 70% identity to SEQ ID No: 3, such as at least 80%, in particular at least 90%, especially at least 95%, for example at least 98%, such as at least 99% and wherein at least one of the catalytic triad have been substituted or deleted or those comprising, such as consisting of, a fragment of SEQ ID No: 3 which is at least 150 amino acids in length, such as at least 200 amino acids in length, in particular at least 250 amino acids in length, especially at least 300 amino acids in length and wherein at least one of the catalytic triad have been substituted or deleted. Further immunogenic derivatives of Rv0125 are those comprising (such as consisting of) the fragment of SEQ ID No: 3 corresponding to residues 192-323 of SEQ ID No: 3 wherein at least one (for example one, two or even all three) of the catalytic triad have been substituted or deleted. Particular immunogenic derivatives of Rv0125 are those comprising (such as consisting of) the fragment of SEQ ID No: 3 corresponding to residues 1-195 of SEQ ID No: 3 wherein the catalytic serine residue (position 176 of SEQ ID No: 3) has been substituted (e.g. substituted with alanine).

Suitably the antigen will comprise, such as consist of, a sequence having at least 70% identity to SEQ ID No. 4, such as at least 80%, in particular at least 90%, especially at least 95%, such as at least 98%, for example at least 99%. Typical M72 related antigens will comprise, such as consist of, a derivative of SEQ ID No: 4 having a small number of deletions, insertions and/or substitutions. Examples are those having deletions of up to 5 residues at 0-5 locations, insertions of up to 5 residues at 0-5 five locations and substitution of up to 20 residues. Other derivatives of M72 are those comprising, such as consisting of, a fragment of SEQ ID No: 4 which is at least 450 amino acids in length, such as at least 500 amino acids in length, such as at least 550 amino acids in length, such as at least 600 amino acids in length, such as at least 650 amino acids in length or at least 700 amino acids in length. As M72 is a fusion protein derived from the two individual antigens Rv0125 and Rv1196, any fragment of at least 450 residues will comprise a plurality of epitopes from the full length sequence (Skeiky et al J. Immunol. 2004 172:7618-7628; Skeiky Infect. Immun. 1999 67(8):3998-4007; Dillon Infect. Immun. 1999 67(6):2941-2950).

M72 related antigen will comprise, such as consist of, a sequence having at least 70% identity to SEQ ID No. 4, such as at least 80%, in particular at least 90%, especially at least 95%, such as at least 98%, for example at least 99%.

Typical M72 related antigens will comprise, such as consist of, a derivative of SEQ ID No: 4 having a small number of deletions, insertions and/or substitutions.

Examples are those having deletions of up to 5 residues at 0-5 locations, insertions of up to 5 residues at 0-5 five locations and substitution of up to 20 residues.

In particular embodiments the M72 related antigen will comprise residues 2-723 of SEQ ID No. 4, for example comprise (or consist of) SEQ ID No. 4 or comprise (or consist) of SEQ ID No. 5.

A further antigen that may be employed in accordance with the present invention is the tuberculosis antigen Rv1753 and variants thereof, such as described in WO2010010180, for example a Rv1753 sequence selected from Seq ID Nos: 1 and 2-7 of WO2010010180, in particular Seq ID No: 1. Another antigen of interest in the field of tuberculosis is Rv2386 and variants thereof, such as described in WO2010010179, for example a Rv2386 sequence selected from Seq ID Nos: 1 and 2-7 of WO2010010179, in particular Seq ID No: 1. Other antigens of interest in the field of tuberculosis include Rv3616 and variants thereof, such as described in WO2011092253, for example a natural Rv3616 sequence selected from Seq ID Nos: 1 and 2-7 of WO2011092253 or a modified Rv3616 sequence such as those selected from Seq ID Nos: 161 to 169, 179 and 180 of WO2011092253, in particular Seq ID No: 167. An additional antigen of interest is HBHA, such as described in WO97044463, WO03044048 and WO2010149657. The aforementioned patent applications WO2010010180, WO2010010179, WO2011092253, WO97044463, WO03044048 and WO2010149657 are incorporated herein by reference in their entirety for the purpose of defining antigens which may be of use in the present invention.

Other antigens of interest are those comprising (or consisting of): Rv1174, also known as DPV, such as described in SEQ ID No 8 of WO2010010177; Rv1793, also known as MTI or Mtb9.9, such as described in SEQ ID No 10 of WO2010010177; Rv2087, also known as MSL or Mtb9.8, such as described in SEQ ID No 9 of WO2010010177; Rv3616, also known as HTCC1 or Mtb40, such as described in SEQ ID Nos 1 and 2-7 WO2010010177 or SEQ ID Nos 161-169, 179 or 180 of WO2011092253; and/or Rv3874, also known as CFP10 or Tb38.1, such as described in SEQ ID No 9 of WO2010010177; or an immunogenic portion (such as at least 20, 50, 75 or 100 residues therefrom) or variant thereof (such as having at least 70%, 80%, 90% or 95% identity thereto). (WO2010010177 and WO2011092253 are incorporated herein by reference in their entirety for the purpose of defining antigens which may be of use in the present invention).

Tuberculosis antigens are most suitably utilised in the form of a polypeptide, but may alternatively be provided in the form of a polynucleotide encoding said polypeptide.

A further antigen that may be employed in accordance with the present invention is derived from Varicella zoster virus (VZV). The VZV antigen for use in the invention may be any suitable VZV antigen or immunogenic derivative thereof, suitably being a purified VZV antigen.

In one embodiment, the VZV antigen is the VZV glycoprotein gE (also known as gp1) or immunogenic derivative hereof. The wild type or full length gE protein consists of 623 amino acids comprising a signal peptide, the main part of the protein, a hydrophobic anchor region (residues 546-558) and a C-terminal tail. In one aspect, a gE C-terminal truncate (also referred to truncated gE or gE truncate) is used whereby the truncation removes 4 to 20 percent of the total amino acid residues at the carboxy terminal end. In a further aspect, the truncated gE lacks the carboxy terminal anchor region (suitably approximately amino acids 547-623 of the wild type sequence). In a further aspect gE is a truncated gE having the sequence of SEQ ID NO. 6.

The gE antigen, anchorless derivatives thereof (which are also immunogenic derivatives) and production thereof is described in EP0405867 and references therein [see also Vafai A., Antibody binding sites on truncated forms of varicalla-zoster virus gpl(gE)glycoprotein, Vaccine 1994 12:1265-9). EP192902 also describes gE and production thereof. Truncated gE is also described by Haumont et al. Virus Research (1996) vol 40, p 199-204, herein incorporated fully by reference. An adjuvanted VZV gE composition suitable for use in accordance of the present invention is described in WO2006/094756, i.e. a carboxyterminal truncated VZV gE in combination with adjuvant comprising QS-21, 3D-MPL and liposomes further containing cholesterol. Leroux-Roels I. et al. (J. Infect. Dis. 2012, 206: 1280-1290) reported on a phase I/II clinical trial evaluating the adjuvanted VZV truncated gE subunit vaccine.

The antigen may comprise or consist of preparations derived from human respiratory syncytial virus (RSV). In certain favorable embodiments, a polypeptide antigen is an F protein polypeptide antigen from RSV. Particularly suitable as a polypeptide antigen component in the context of the are conformationally constrained F polypeptide antigens. Conformationally constrained F proteins have previously been described in both the prefusion (PreF) and postfusion (PostF) conformations. Such conformationally constrained F proteins typically comprise an engineered RSV F protein ectodomain. An F protein ectodomain polypeptide is a portion of the RSV F protein that includes all or a portion of the extracellular domain of the RSV F protein and lacks a functional (e.g., by deletion or substitution) transmembrane domain, which can be expressed, e.g., in soluble (not attached to a membrane) form in cell culture.

Exemplary F protein antigens conformationally constrained in the prefusion conformation have been described in the art and are disclosed in detail in e.g., U.S. Pat. No. 8,563,002 (WO2009079796); US Published patent application No. US2012/0093847 (WO2010/149745); US2011/0305727 (WO2011/008974); US2014/0141037, WO2012/158613 and WO2014/160463 each of which is incorporated herein by reference for the purpose of illustrating prefusion F polypeptides (and nucleic acids), and methods of their production. Typically, the antigen is in the form of a trimer of polypeptides. Additional publications providing examples of F proteins in the prefusion conformation include: McLellan et al., Science, Vol. 340: 1113-1117; McLellan et al., Science, Vol 342: 592-598, and Rigter et al., PLOS One, Vol. 8: e71072, each of which can also be used in the context of the immunogenic combinations disclosed herein.

For example, an F protein polypeptide stabilized in the prefusion conformation typically includes an ectodomain of an F protein (e.g., a soluble F protein polypeptide) comprising at least one modification that stabilized the prefusion conformation of the F protein. For example, the modification can be selected from an addition of a trimerization domain (typically to the C terminal end), deletion of one or more of the furin cleavage sites (at amino acids ~105-109 and ~133-136), a deletion of the pep27 domain, substitution or addition of a hydrophilic amino acid in a hydrophobic domain (e.g., HRA and/or HRB). In an embodiment, the conformationally constrained PreF antigen comprises an F2 domain (e.g., amino acids 1-105) and an F1 domain (e.g., amino acids 137-516) of an RSV F protein polypeptide with no intervening furin cleavage site wherein the polypeptide further comprises a heterologous trimerization domain positioned C-terminal to the F1 domain. Optionally, the PreF antigen also comprises a modification that alters glycosylation (e.g., increases glycosylation), such as a substitution of one or more amino acids at positions corresponding to amino acids ~500-502 of an RSV F protein. When an oligomerization sequence is present, it is preferably a trimerization sequence. Suitable oligomerization sequences are well known in the art and include, for example, the coiled coil of the yeast GCN4 leucine zipper protein, trimerizing sequence from bacteriophage T4 fibritin ("foldon"), and the trimer domain of influenza HA. Additionally or alternatively, the F polypeptide conformationally constrained in the prefusion conformation can include at least two introduced cysteine residues, which are in close proximity to one another and form a disulfide bond that stabilizes the prefusion RSV F polypeptide. For example, the two cysteines can be within about 10 A of each other. For example, cysteines can be introduced at positions 165 and 296 or at positions 155 and 290. An exemplary PreF antigen is represented by SEQ ID NO:7.

The antigen may comprise or consist of preparations derived from HIV. The antigen may be a HIV protein such as a HIV envelope protein. For example, the antigen may be a HIV envelope gp120 polypeptide or an immunogenic fragment thereof.

One suitable antigen is the HIV clade B gp120 polypeptide of SEQ ID NO: 8 of the published application WO 2008/107370 (or an immunogenic fragment of this polypeptide). SEQ ID NO: 8 of WO 2008/107370 is incorporated by reference into this application.

Suitable antigens also include a polypeptide comprising the VIV2 region of SEQ ID NO: 1 of the published application WO 2015/036061, or an immunogenic derivative or fragment of the V1V2 region of SEQ ID NO: 1. In addition, a polypeptide comprising the VIV2 region of SEQ ID NO: 5 of WO 2015/036061 or an immunogenic derivative or fragment of the V1V2 region of SEQ ID NO: 5 may be used as a suitable antigen. SEQ ID NO: 1 and SEQ ID NO: 5 of WO2015/036061 are incorporated by reference.

In another embodiment, the antigen may comprise two or more different HIV envelope gp120 polypeptide antigens (or immunogenic fragments of these polypeptides). Suitable antigens include the and HIV clade C gp120 polypeptide antigens including TV1 gp120 (SEQ ID No: 8) and 1086.0 gp120 (SEQ ID No: 9).

Other suitable HIV antigens include Nef, Gag and Pol HIV proteins and immunogenic fragments thereof.

The composition may comprise non-typeable *Haemophilus influenzae* antigen(s) for example selected from: Fimbrin protein [(U.S. Pat. No. 5,766,608—Ohio State Research Foundation)] and fusions comprising peptides therefrom [e.g. LB1(f) peptide fusions; U.S. Pat. No. 5,843,464 (OSU) or WO 99/64067]; OMP26 [WO 97/01638 (Cortecs)]; P6 [EP 281673 (State University of New York)]; TbpA and/or TbpB; Hia; Hsf; Hin47; Hif; Hmw1; Hmw2; Hmw3; Hmw4; Hap; D15 (WO 94/12641); protein D (EP 594610); P2; and P5 (WO 94/26304); protein E (WO07/084053) and/or PilA (WO05/063802). The composition may comprise *Moraxella catarrhalis* protein antigen(s), for example selected from: OMP106 [WO 97/41731 (Antex) & WO 96/34960 (PMC)]; OMP21; LbpA &/or LbpB [WO 98/55606 (PMC)]; TbpA &/or TbpB [WO 97/13785 & WO 97/32980 (PMC)]; CopB [Helminen M E, et al. (1993) Infect. Immun. 61:2003-2010]; UspA1 and/or UspA2 [WO 93/03761 (University of Texas)]; OmpCD; HasR (PCT/EP99/03824); PilQ (PCT/EP99/03823); OMP85 (PCT/EP00/01468); lipo06 (GB 9917977.2); lipo10 (GB 9918208.1); lipo11 (GB 9918302.2); lipo18 (GB 9918038.2); P6 (PCT/EP99/03038); D15 (PCT/EP99/03822); OmplA1 (PCT/EP99/06781); Hly3 (PCT/EP99/03257); and OmpE.

In an embodiment, the composition may comprise non-typeable *H. influenzae* (NTHi) protein antigen(s) and/or *M. catarrhalis* protein antigen(s). The composition may comprise Protein D (PD) from *H. influenzae*. Protein D may be as described in WO91/18926. The composition may further comprise Protein E (PE) and/or Pilin A (PilA) from H. *Influenzae*. Protein E and Pilin A may be as described in WO2012/139225. Protein E and Pilin A may be presented as a fusion protein; for example LVL735 as described in WO2012/139225. For example, the composition may comprise three NTHi antigens (PD, PE and PilA, with the two last ones combined as a PEPiIA fusion protein). The composition may further comprise UspA2 from *M. catarrhalis*. UspA2 may be as described in WO2015125118, for example MC-009 ((M)(UspA2 31-564)(HH)) described in WO2015125118. For example, the composition may comprise three NTHi antigens (PD, PE and PilA, with the two last ones combined as a PEPiIA fusion protein) and one *M. catarrhalis* antigen (UspA2).

A plurality of antigens may be provided. For example, a plurality of antigens may be provided to strengthen the elicited immune response (e.g. to ensure strong protection), a plurality of antigens may be provided to broaden the immune response (e.g. to ensure protection against a range of pathogen strains or in a large proportion of a subject population) or a plurality of antigens may be provided to currently elicit immune responses in respect of a number of disorders (thereby simplifying administration protocols). Where a plurality of antigens are provided, these may be as distinct proteins or may be in the form of one or more fusion proteins.

Antigen may be provided in an amount of 0.1 to 100 ug per human dose.

The present invention may be applied for use in the treatment or prophylaxis of a disease or disorder associated with one or more antigens described above. In one embodiment the disease or disorder is selected from malaria, tuberculosis, COPD, HIV and herpes.

The liposomal adjuvant may be administered separately from an immunogen or antigen, or may be combined, either during manufacturing or extemporaneously), with an immunogen or antigen as an immunogenic composition for combined administration.

Sterilisation

For parenteral administration in particular, compositions should be sterile. Sterilisation can be performed by various methods although is conveniently undertaken by filtration through a sterile grade filter. Sterilisation may be performed a number of times during preparation of an adjuvant or immunogenic composition, but is typically performed at least at the end of manufacture.

By "sterile grade filter" it is meant a filter that produces a sterile effluent after being challenged by microorganisms at a challenge level of greater than or equal to $1 \times 10^7/cm^2$ of effective filtration area. Sterile grade filters are well known to the person skilled in the art of the invention for the purpose of the present invention, sterile grade filters have a pore size between 0.15 and 0.25 um, suitably 0.18-0.22 um, such as 0.2 or 0.22 um.

The membranes of the sterile grade filter can be made from any suitable material known to the skilled person, for example, but not limited to cellulose acetate, polyethersulfone (PES), polyvinylidene fluoride (PVDF), polytetrafluoroethylene (PTFE). In a particular embodiment of the invention one or more or all of the filter membranes of the present invention comprise polyethersulfone (PES), in particular hydrophilic polyethersulfone. In a particular embodiment of the invention, the filters used in the processes described herein are a double layer filter, in particular a sterile filter with build-in prefilter having larger pore size than the pore size of the end filter. In one embodiment the sterilizing filter is a double layer filter wherein the pre-filter membrane layer has a pore size between 0.3 and 0.5 nm, such as 0.35 or 0.45 nm. According to further embodiments, filters comprise asymmetric filter membrane(s), such as asymmetric hydrophilic PES filter membrane(s). Alternatively, the sterilizing filter layer may be made of PVDF, e.g. in combination with an asymmetric hydrophilic PES pre-filter membrane layer.

In light of the intended medical uses, materials should be of pharmaceutical grade (such as parenteral grade).

By the term 'substantially' in respect of an integer is meant functionally comparable, such that deviation may be tolerated if the essential nature of the integer is not changed. For example, in respect of specific values, the term 'substantially' will typically mean a value within plus or minus 10 percent of the stated value.

The teaching of all references in the present application, including patent applications and granted patents, are herein fully incorporated by reference. A composition or method or process defined as "comprising" certain elements is understood to encompass a composition, method or process (respectively) consisting of those elements. As used herein, 'consisting essentially of' means additional components may be present provided they do not alter the overall properties or function.

The invention will be further described by reference to the following, non-limiting, examples:

EXAMPLES

General Experimental Details
Single Mixing Chamber Microfluidic Device and General Operation
Device FIG. 1 illustrates the design of an exemplary microfluidic device having one mixing chamber on a single chip. The device comprises a mixing chamber of 2.5 cm in length and having an elongate cross-section of 2 mm by 0.4 mm. The mixing chamber has one centrally located inlet for the provision of the first solution and two inlets for the provision of the second solution. Each of the inlets is 0.2 mm wide and spans the full length of the other side of the mixing chamber. A single outlet is located at the distal end of the mixing chamber.

Operation

To perform microfluidic experiments, Cetoni neMesys Mi-pressure syringe pumps, Cetoni glass syringes and a Micronit chip-holder containing the device were placed in a temperature controlled area (Sartorius Certomat). Before any experimental runs, the system is cleaned and allowed to stabilize at the set temperature.

Product Collection and Solvent Removal

The concentrated liposomes collected were divided into 2 parts:

The first part was diluted with phosphate buffered saline (PBS) pH6.1 to reach a final concentration of 2 mg/ml DOPC and filtered on 0.22 urn polyethersulfone (PES) membrane. Composition testing (DOPC, Cholesterol, 3D-MPL, QS-21) were performed on this sample.

The second part was dialysed (Device 7000MWCO Thermo Slide-A-Lyser) with phosphate buffered saline pH6.1 to remove the organic solvent. The protocol used was: 2×15 min, 2×30 min and overnight (1 L of PBS pH6.1 buffer at each time point). The retentate was then diluted to reach 2 mg/ml DOPC and filtered on 0.22 urn PES membrane. Size measurements were undertaken on this sample. Residual alcohol was tested on this sample by gas chromatography.

Multi Mixing Chamber Microfluidic Device and General Operation
Device

Figure 2:
FIG. 2: Eight mixing chamber microfluidic chip

FIG. 2 illustrates the design of an exemplary multi mixing chamber microfluidic device having eight mixing chambers on a single chip. The device comprises eight mixing chambers of 2.5 cm in length and having an elongate cross-section of 2 mm by 0.4 mm. Each mixing chamber has one centrally located inlet for the provision of the first solution and two inlets for the provision of the second solution. Each of the inlets is 0.2 mm wide and spans the full length of the other side of the mixing chambers. A single outlet is located at the distal end of each of the mixing chambers.

Figure 3:
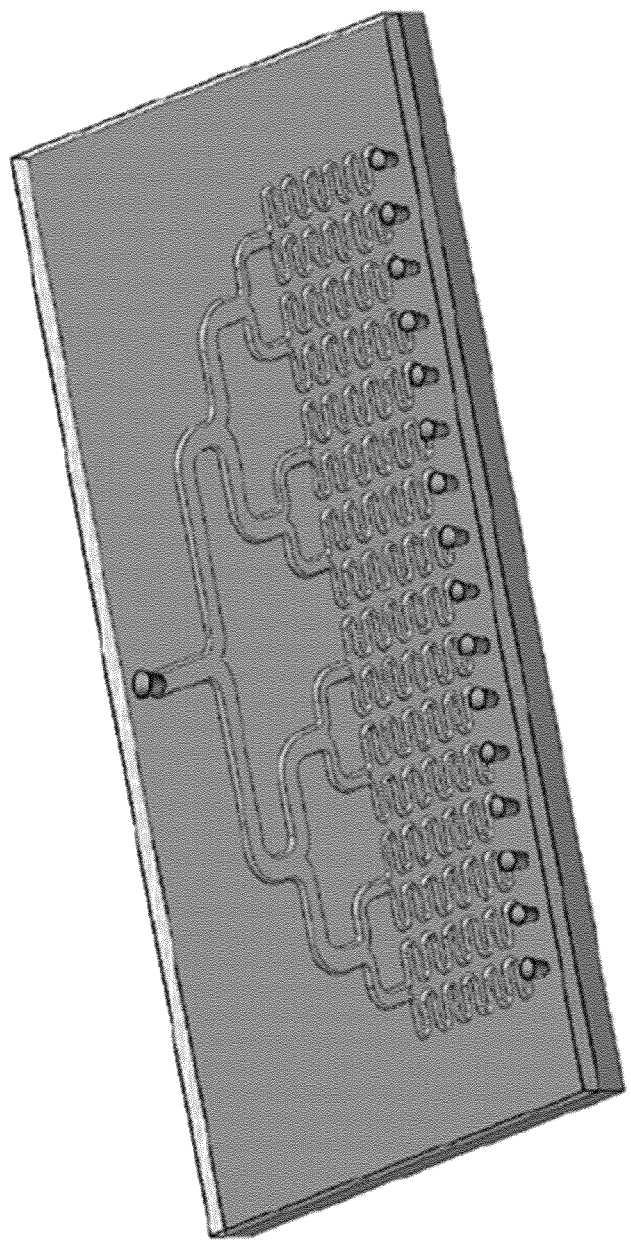
FIG. 3: Liquid distribution manifold (one to sixteen)

FIG. 3 illustrates a manifold design which can be used in conjunction with a multi mixing chamber microfluidic chip, to supply first solution or second solution to the inlets of sixteen mixing chambers, or to collect mixed material from the outlets of sixteen mixing chambers.

Figure 4:
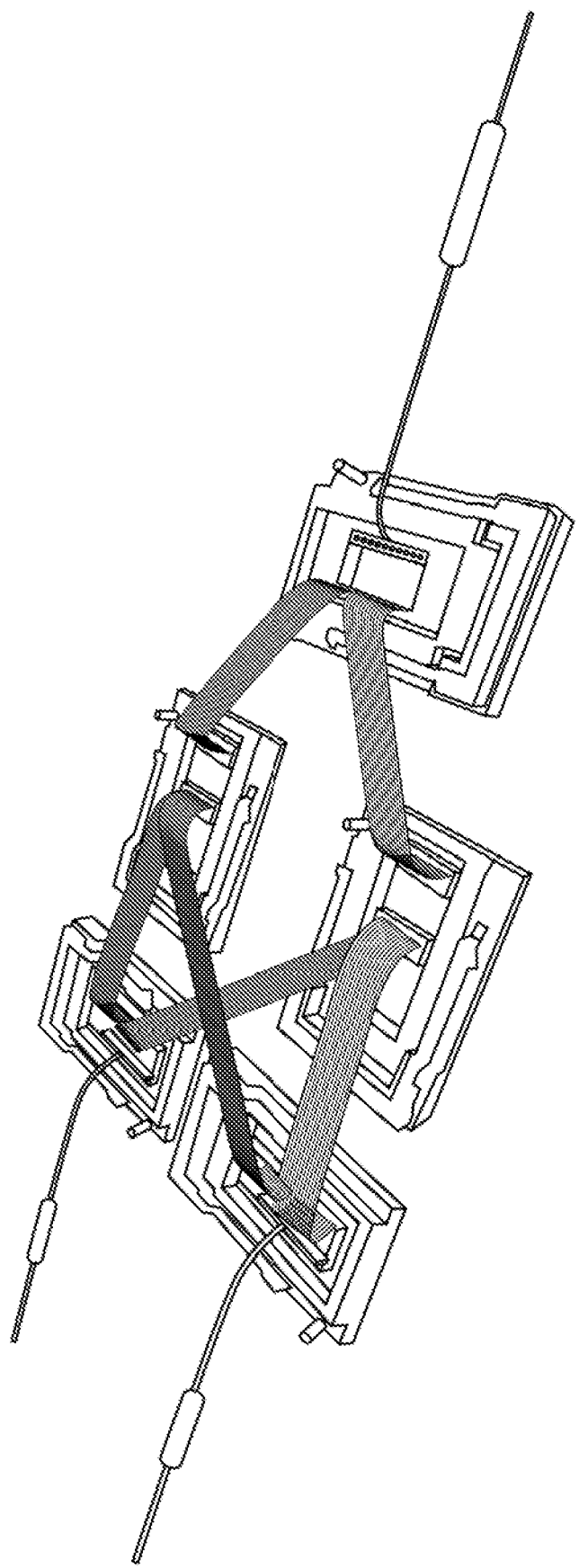
FIG. 4: Operational arrangement of two eight mixing chamber microfluidic chips with distribution and collection manifolds

FIG. 4 is a representation of an exemplary multi mixing chamber microfluidic device having a total of sixteen mixing chambers based on two chips of the style shown in FIG. 2 (occupying the two central holders), in conjunction with a distribution manifold supplying the first solution inlets of the sixteen chambers (lower left holder), a distribution manifold supplying the second solution inlets of the sixteen chambers (upper left holder) and a collection manifold which pools the outlets from the sixteen chambers (right holder).

Operation

The multi mixing chamber device may be operated in a manner similar to the single device. For example, organic stock (e.g. 4.9 L) may be prepared containing DOPC 130 mg/ml, Cholesterol 32.5 mg/ml and 3D-MPL 6.5 mg/ml in 80:20 ethanol/IPA. The aqueous phase (e.g. 19.7 L) may be composed of QS-21 at 1.625 mg/ml diluted in water for injection.

Suitable pumps, such as Isco 500D in tandem for organic phase and 1000D in tandem for aqueous phase, may be used in continuous flow to supply the liquid phases through manifolds dividing the flows into 16 streams which enter the 16 mixing chambers arranged in parallel. At the end of the mixing chambers, another manifold may be used to collect the mixed material containing concentrated liposomes into one vessel.

Diafiltration may be used to remove the organic solvent from the mixed material and replace the water for injection with a suitable buffer (such as PBS pH6.1 buffer).

Further dilution with suitable buffer (e.g. PBS pH6.1) allows the final composition to be achieved depending on the desired concentration of components. Sterile filtration may then be undertaken.

Analytical Methods
Size Measurements

Size measurements made use of the DLS principle with a Malvern Zetasizer instrument. Samples were diluted in the corresponding buffer (typically PBS pH6.1) for the measurements.

3D-MPL Content

HPLC coupled with fluorescence detection was used to quantify the 3D-MPL component. Separation was realized on C18 column.

Standards were prepared from equimolar mix of glucosamine HCl and glucosamine 6 phosphate reconstituted in the liposomal matrix (DOPC, Cholesterol).

Samples and standards are derivatized with acid in strong reducing conditions.

QS-21 Content

HPLC coupled with UV detection was used to quantify the QS-21 component. Separation is realized on C18 column.

Standards are prepared with a QS-21 reference diluted in DMSO from 25 to 75 ug/ml Samples are diluted in DSMO for analysis.

DOPC-Chol Content 2 methods were used:

First method (individual standards) used U-HPLC coupled with UV detector. Separation was realized on C18 column.

Standards were prepared with DOPC/Choi diluted in IPA/CHCl$_3$ for stock and diluted in same buffer from 0 to 700 ug/ml for DOPC and 0 to 175 ug/ml for Cholesterol.

Samples are diluted in IPA/CHCl$_3$.

Second method (relative to previously characterised adjuvant composition) used HPLC coupled with UV detector. Separation is realized on C18 column Standards are prepared using previously characterised adjuvant composition, prepared by classical means, diluted in methanol from 0 to 500 ug/ml for DOPC and 0 to 125 ug/ml for Cholesterol Samples are diluted in methanol Solvent Residuals Method using Gas-Chromatography coupled with Head-Space injector and FID (Flam Ionization detector). Separation is realized on CP WAX52-CB Agilent column.

Standards are prepared for each specific organic solvent (in this case, IPA and Ethanol) from 2 to 160 ug/ml. The LOQ is at 2 ug/ml Samples are diluted in order to be in the range of the standards.

Example 1: Investigation of First Solution Preparation Methods and Composition

Example 1A—Solvent Composition

Method

To investigate the impact of solvent composition on liposome production, solutions of DOPC, cholesterol and 3D-MPL were prepared in various ethanol/isopropyl alcohol ratios.

DOPC, cholesterol and 3D-MPL were each individually solubilised (60% volume for DOPC, 20% for cholesterol and 20% for 3D-MPL) for 15 minutes at 55° C. 3D-MPL solution was then added to DOPC solution and this mixture added to the cholesterol solution and further mixed for 15 additional minutes to provide final compositions with 150 mg/ml DOPC (20:5:1 weight ratio DOPC:cholesterol:3D-MPL).

The single chamber microfluidics device was operated with a total flow rate of 14 ml/min, flow rate ratio of 20 (19:1) (1:19 organic:aqueous), using water for injection as the aqueous phase, with stock solutions and environment at room temperature.

Results

TABLE 1

| Impact of solvent composition on liposome size | |
|---|---|
| Ethanol:IPA ratio | Liposome size (nm) |
| 100:0 | — |
| 80:20 | 124 |
| 70:30 | 139 |
| 60:40 | 154 |
| 50:50 | 174 |

Conclusions

Pure ethanol was unable to solubilise the components at the target concentration. Although pure isopropanol was able to solubilise the components at the target concentration, the liposomes produced in a similar experiment (160 mg/ml) were very large with a diameter of 203 nm.

Mixtures of ethanol and IPA, particularly in the range of 90:10 to 70:30 provide good solubilisation capacity with low viscosity.

Example 1B—Solution Preparation

Method

The order of component addition was evaluated comparing the two following methods:

1. DOPC, cholesterol and 3D-MPL were each individually solubilised (60%, 20%, 20% volumes respectively) in 80:20 ethanol:IPA for 15 minutes at 55° C. 3D-MPL solution was then added to DOPC solution and further mixed for 15 additional minutes. The 3D-MPL/DOPC mixture was then added to the cholesterol solution and further mixed for 1 additional hr to provide a final composition with 120 mg/ml DOPC (20:5:1 weight ratio DOPC:cholesterol:3D-MPL).

2. 3D-MPL was suspended with 50% of the solvent (80:20 ethanol:IPA) and then added to DOPC and cholesterol powders. The volume was then adjusted with the rest of the solvent and the mixture heated to 40° C. for 15 minutes to provide a final composition with 120 mg/ml DOPC (20:5:1 weight ratio DOPC:cholesterol:3D-MPL).

Method 1 required the mixture to be kept at 55° C. for 1 h for complete solubilisation of the components. However, if not kept under mild agitation for a few minutes, a phase separation can be observed. In order to avoid this, continuous agitation is required until solubilisation is complete.

Method 2 allows complete solubilisation after less time (15 min) and no phase separation can be observed if not agitated.

The single mixing chamber microfluidics device was operated with a total flow rate of 18 ml/min, flow rate ratio of 20 (1:19 organic:aqueous) and at temperatures of 15-25° C. using stock first solution prepared by both methods. The second solution (aqueous) was QS-21 in water for injection.

Results

Figure 5:
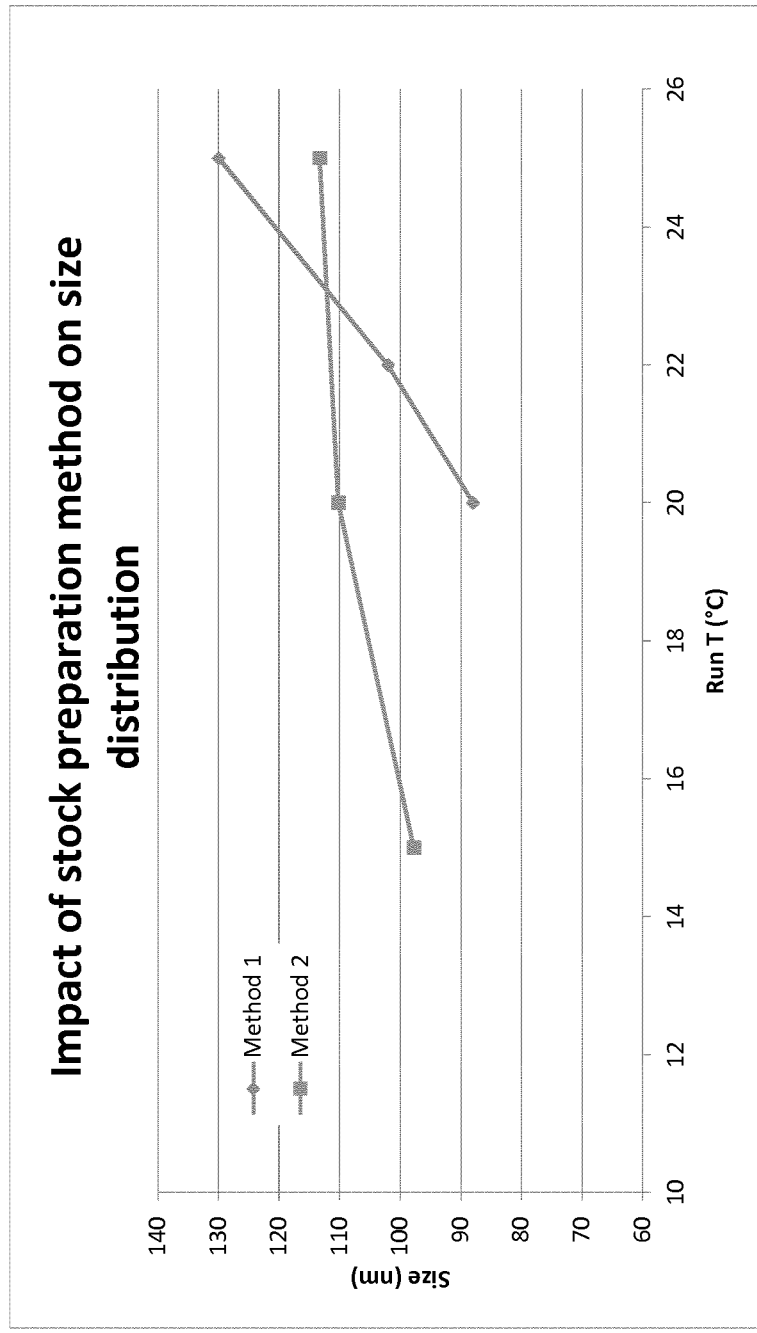
FIG. 5: Impact of stock preparation method on lipsome size distribution

The results are shown in FIG. 5.

Conclusions

Method 1 is more sensitive to temperature while Method 2 allows for a less temperature sensitive microfluidic operation with liposome samples within size specification of 95-120 nm on the 15-25° C. range.

Example 1C—Solution Concentration Limits

The impact of the concentration of the DOPC, cholesterol and 3D-MPL on the stock stability and solubility was evaluated.

Stock solutions of DOPC, cholesterol and 3D-MPL in ethanol/IPA 80:20 were prepared at DOPC concentrations of 40, 60, 80, 100, 120, 140, 160 and 200 mg/ml (20:5:1 weight ratio DOPC:cholesterol:3D-MPL) following Method 2. Measurement was first made at To (30° C.), samples were then stored at 25° C. for one hour, analysed and then stored at 20° C. for one hour, analysed and then stored at 15° C. for one hour and analysed.

Results

Figure 6:
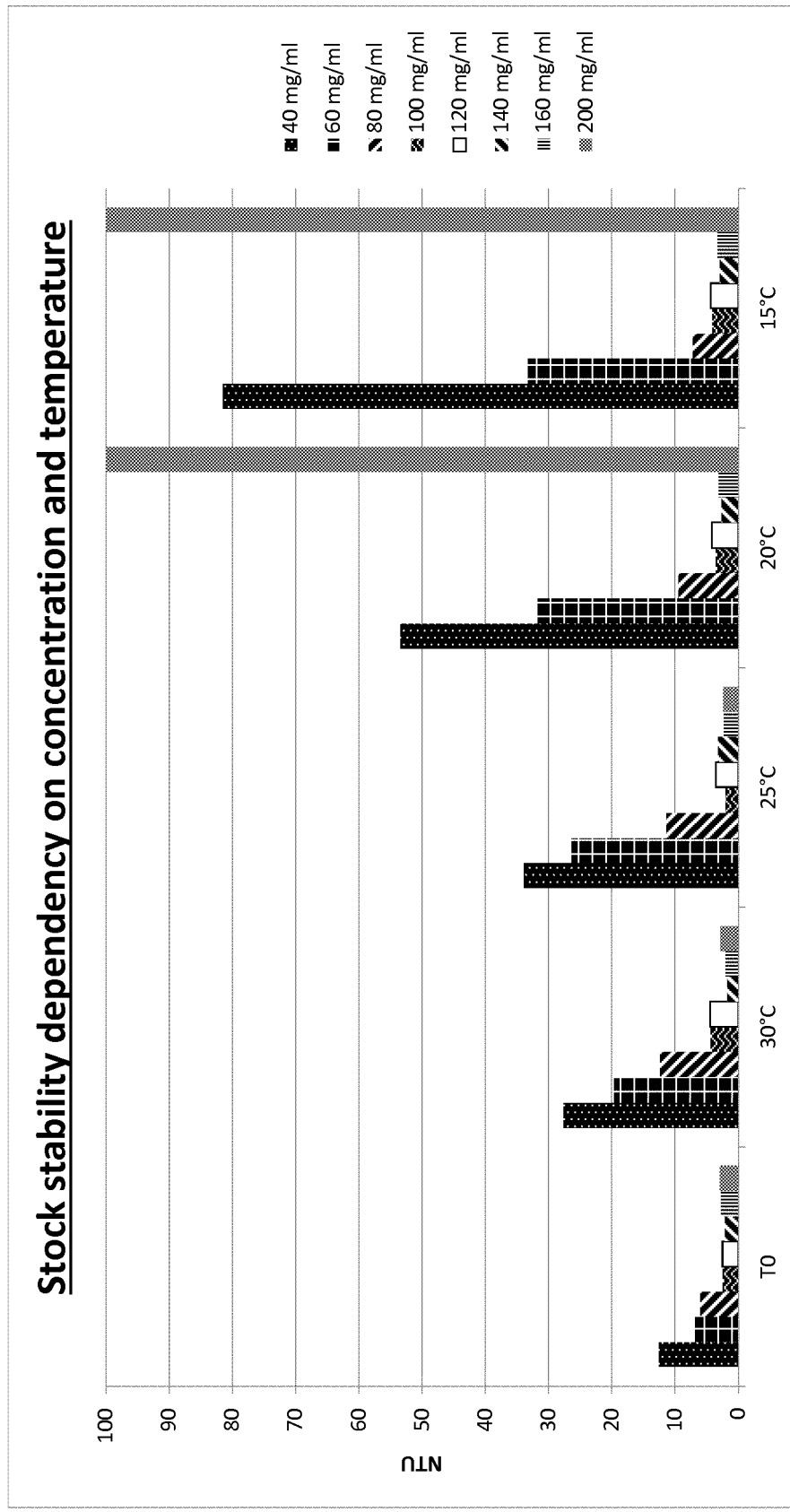
FIG. 6: Stock stability dependency on concentration and temperature

The results are shown in FIG. 6.

Nephelometric measurement by Nephelostar revealed that concentrations below 100 mg/ml evolve and have higher turbidity. Similarly, 200 mg/ml evolves and has higher turbidity.

Conclusions

Concentrations between 100 and 160 mg/ml are stable at temperatures between 15° C. and 30° C. These surprising results could be explained by specific interactions between the lipid (DOPC), sterol (cholesterol) and TLR4 agonist (3D-MPL) when mixed in ethanol/IPA within this concentration range.

Example 2: Investigation of the Impact of Solvent Composition and Temperature on Liposome Size Method Stock solutions of DOPC, cholesterol and 3D-MPL were prepared at a DOPC concentration of 120 mg/ml (20:5:1 weight ratio DOPC:cholesterol:3D-MPL) following Method 2 in ethanol:IPA at ratios of 80:20; 70:30 and 60:40 and used along with aqueous QS-21 stock at 1.5 mg/ml.

The microfluidics process was run at temperatures of 15° C., 20° C. and 25° C. at a total flowrate of 18 ml/min and a flowrate ratio of 5 (1:4 organic:aqueous).

In this experiment liposome sizes were measured before dialysis.

Results

Figure 7:
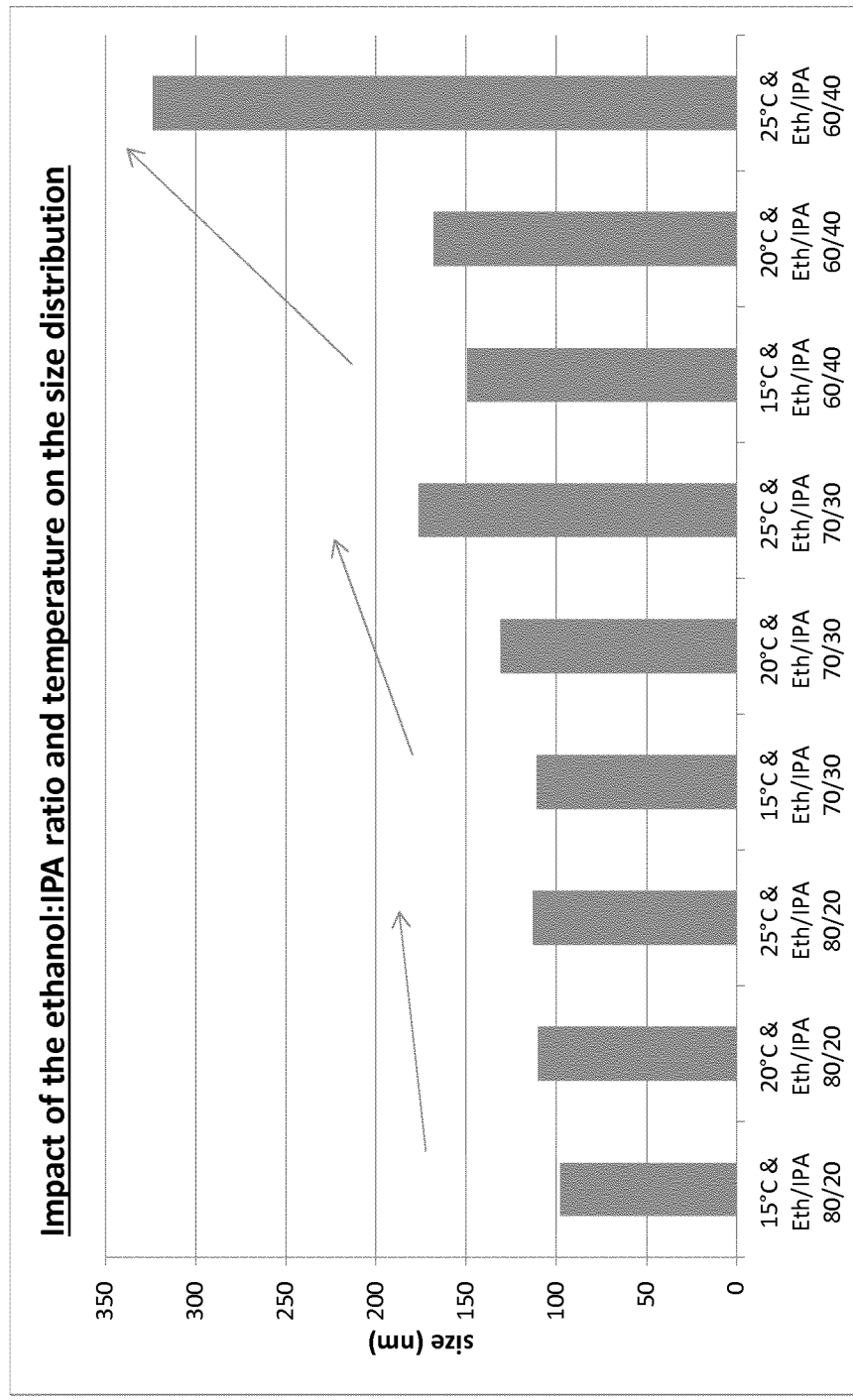
FIG. 7: Impact of solvent composition and temperature on liposome size

The results are shown in FIG. 7.

Conclusions

The temperature partially drives the solubility of the components (DOPC, cholesterol and 3D-MPL). Stock prepared at 40° C. can be cooled down to 15° C. without precipitation. However, operation at lower temperatures induces faster precipitation and thereby results in smaller liposomes.

The liposome size is impacted by the composition of the first solution different temperatures with greatest variation with ratio of 60:40>70:30>80:20. This experiment also confirms the choice of an 80:20 ratio as having the lowest sensitivity to temperature.

Example 4: Detailed Analysis of Microfluidic Run Conditions and their Impact on Liposome Size Based on the general limits determined previously, a DOE (Design of Experiment) central composite was built to determine the process response in terms of size (Zav) and detect any cross interactions between temperature, total flow rate, flow rate ratio and stock concentration.

Method

TABLE 2

Summary of conditions investigated

| Parameter | Evaluation range (upper & lower limits) |
|---|---|
| First solution | 100 ug/ml |
| DOPC concentration | 160 ug/ml |
| Total flow rate | 14 ml/min |
|  | 20 ml/min |
| Flow rate ratio | 4 (1:3 organic:aqueous) |
|  | 6 (1:5 organic:aqueous) |
| Temperature | 15° C. |
|  | 25° C. |

Figure 9:
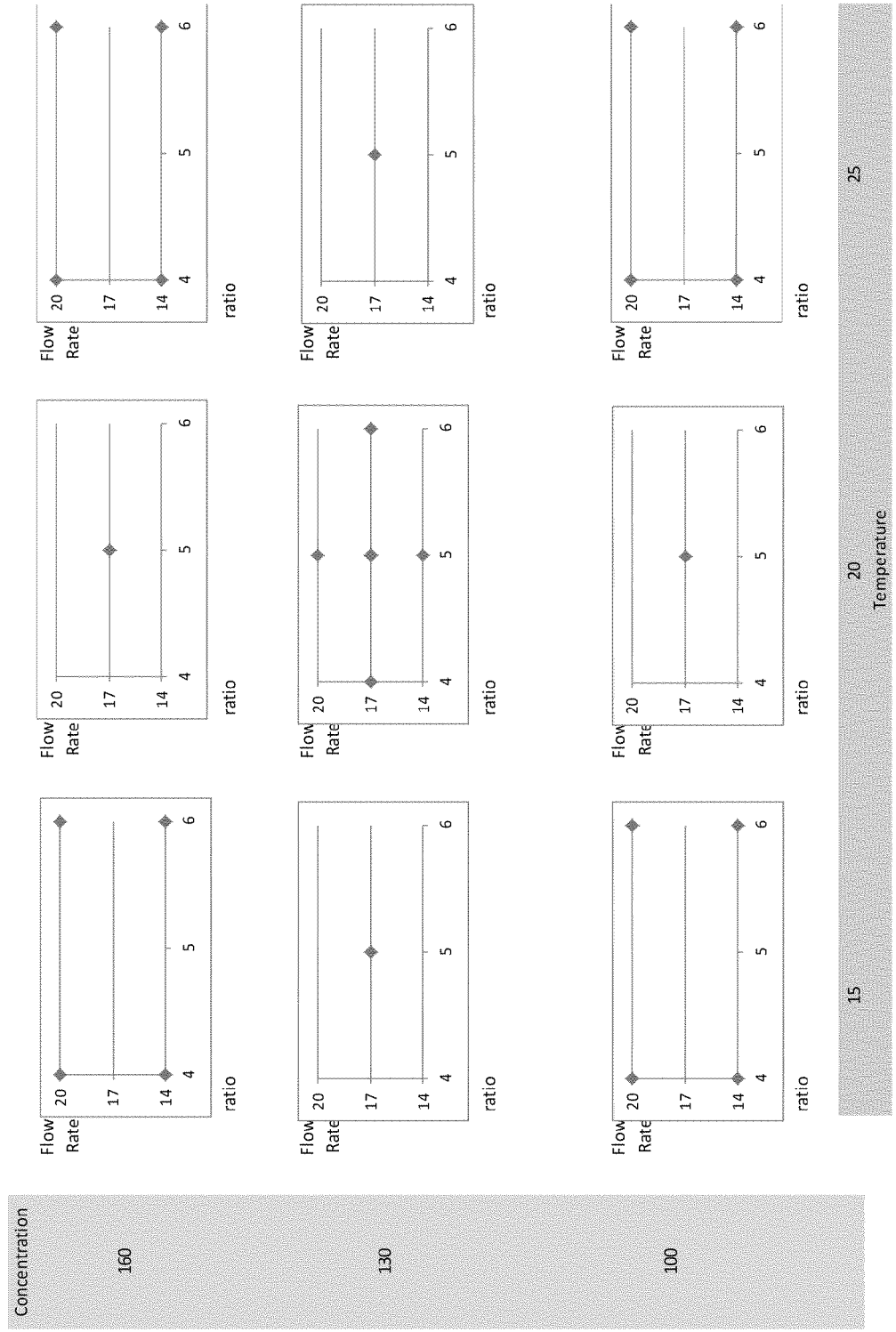
FIG. 9: Visual summary of Example 4 test conditions

A table of test conditions is provided in FIG. 8 with a visual summary of the test conditions in FIG. 9. Experiments were undertaken over four days.

First solutions were prepared according to Method 2 as described previously. Briefly DOPC (Lipoid) was weighed, followed with Cholesterol (Sigma). In a separate vial, 3D-MPL (GSK Hamilton) was weighed. 50% of the organic phase (80% Ethanol (Merck) and 20% Isopropanol was added to the 3D MPL. The suspended MPL was then added to the DOPC/cholesterol powder and placed at 40° C. under mixing. After solubilisation of the three components (clear solution), the organic stock is left for a further 15 minutes at 40° C. The volume is then adjusted to provide the target concentration (20:5:1 weight ratio DOPC:cholesterol:3D-MPL).

For the second solution, QS-21 concentrated liquid bulk was diluted in water for injection to reach the final concentration required.

Statistical analysis was performed using SAS 9.2 and Design Expert 9 based on a face-cantered central composite design for response surface estimation, with 6 cente points and 24 model points.

Reynolds numbers were calculated per the equation:

$$Re = \frac{\rho U D_h}{\mu} = \frac{\rho U}{\mu} \frac{2wh}{w+h} = \frac{\rho}{\mu} \frac{2Q}{w+h}$$

For example under the conditions:

|  | Organic phase | Aqueous phase |
|---|---|---|
| Density | 0.829 g/cm$^3$ at 22.4° C. | 1.002 g/cm$^3$ at 21.7° C. |
| Viscosity | 3.345 Cp at 19.8° C. | 1.09 Cp at 20° C. |
| Flow-rate | 3.2 ml/min | 12.8 ml/min |
| Working T° | 20° C. | 20° C. |

Based on the mean densities and viscosities of the fluids as per their proportions:

Density: $(12.8 \times 1.002 + 3.2 \times 0.829)/16 = 0.9674$ g/cm$^3$

Viscosity: $(12.8 \times 1.09 + 3.2 \times 3.345)/16 = 1.541$ Cp, if 1 Pa=1 kg·m$^{-1}$·s$^{-2}$ and 1 Cp=1 mPa·s then viscosity=1.541 g·m$^{-1}$·s$^{-1}$=0.01541 g·cm$^{-1}$·s$^{-1}$ The mixing chamber dimensions are: 2000 um (w)×400 um (h).

$$2Q = 2 \times 16 = 32 \text{ ml/min} = 0.53 \text{ cm}^3/\text{s}$$

$$W + h = 400 \text{ um (height)} + 2000 \text{ um (wide)} = 2400 \text{ um} = 0.24 \text{ cm}$$

Everything inside the equation: $(0.9674 \times 0.53)/(0.01541 \times 0.24) = 138.6$ An equivalent approach can be taken for all flow-rates and flow-rate ratios.

Results

FIG. 10 provides the results of the experiment.

Modelling of Pdl

Table 3 presents the standard deviation (SD) and coefficient of variance (CV) for Zav and Pdl.

TABLE 3

Analysis of repeatability on centre point of the DOE

|  | Zav | Pdl |
|---|---|---|
| SD repeatability | 1.17 | 0.01 |
| SD intermediate precision | 5.53 | 0.03 |
| CV repeatability | 1.05% | 4.24% |
| CV intermediate precision | 4.97% | 16.89% |

Figure 11:
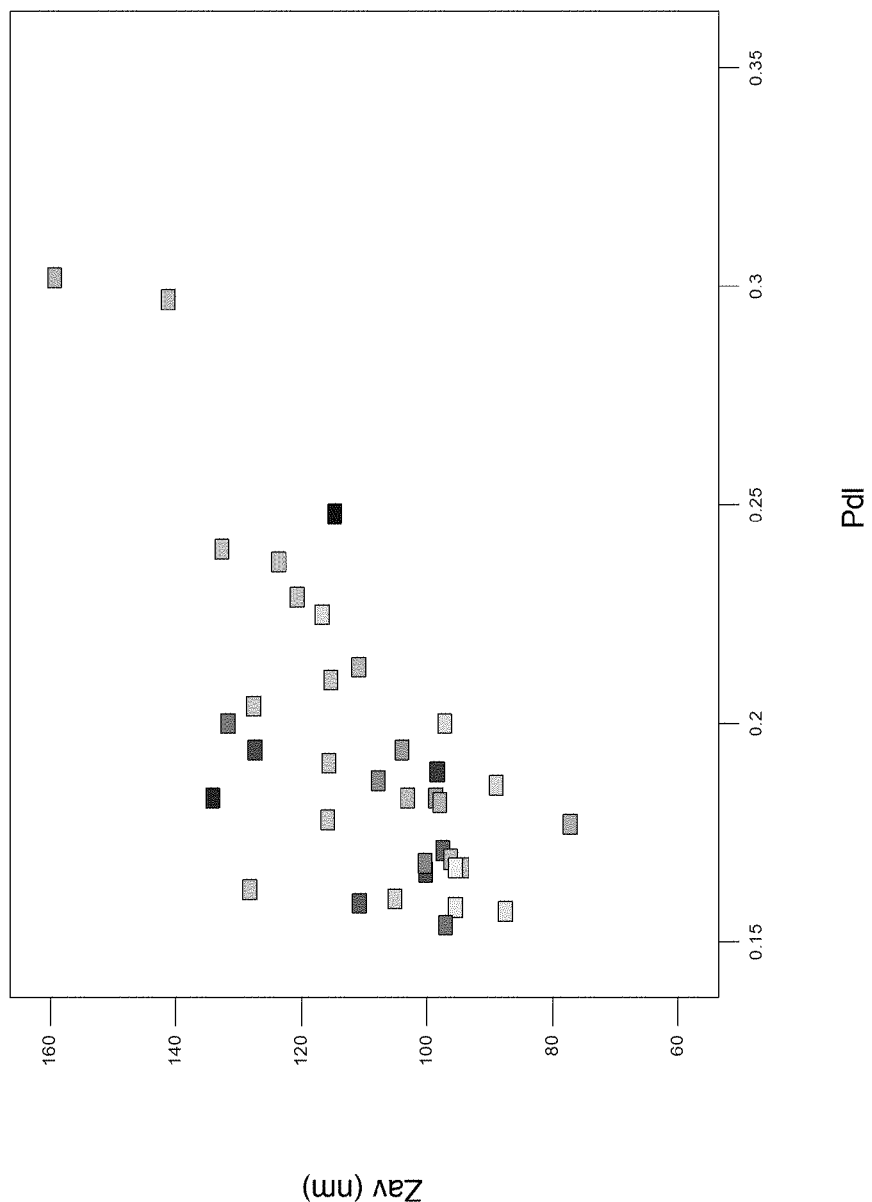
FIG. 11: Relationship between Zav and Pdl
Figure 12:
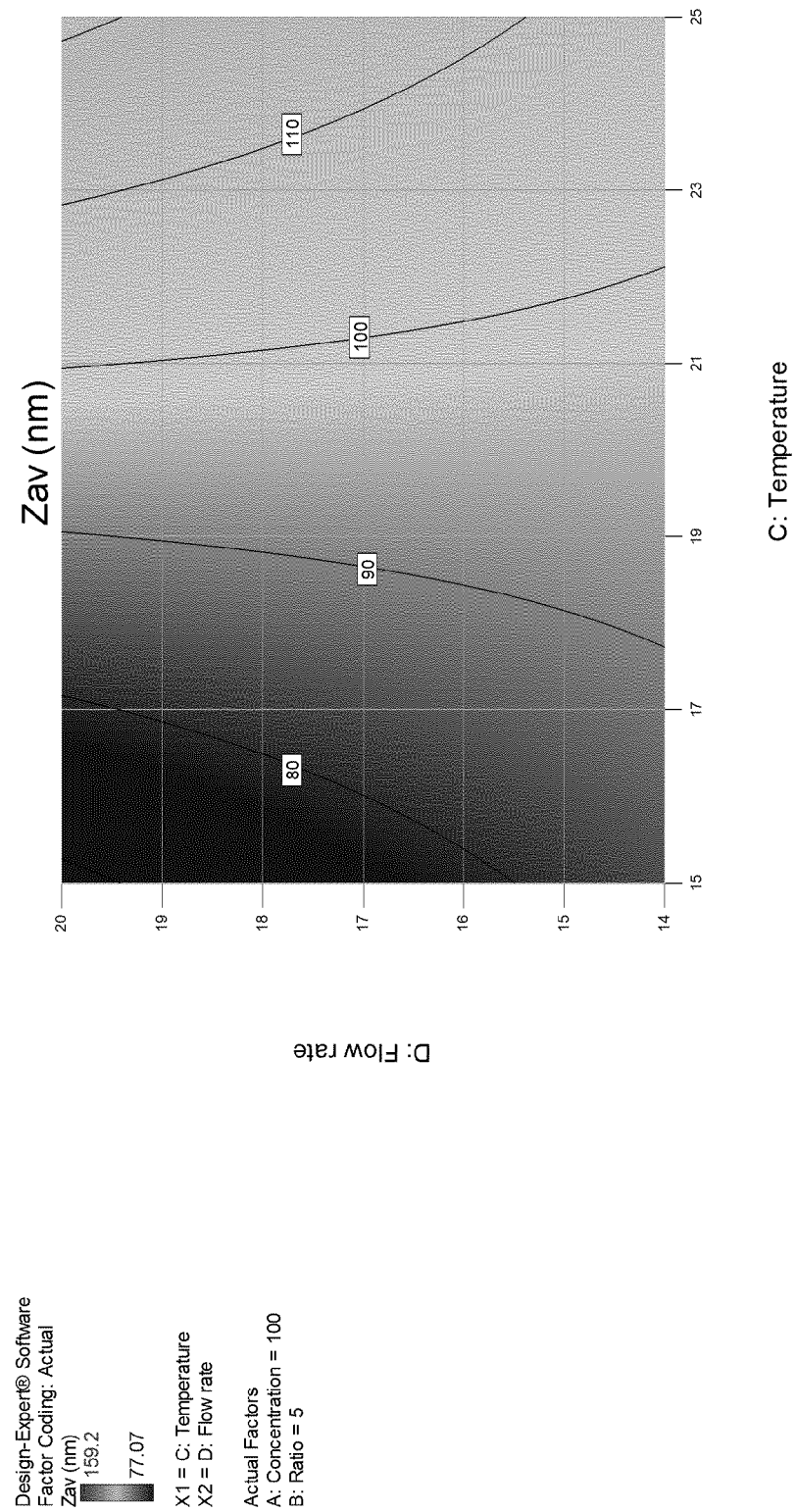
FIG. 12: Prediction of size at 100 mg/ml DOPC and ratio 5 (1:4 organic:aqueous phases)
Figure 13:
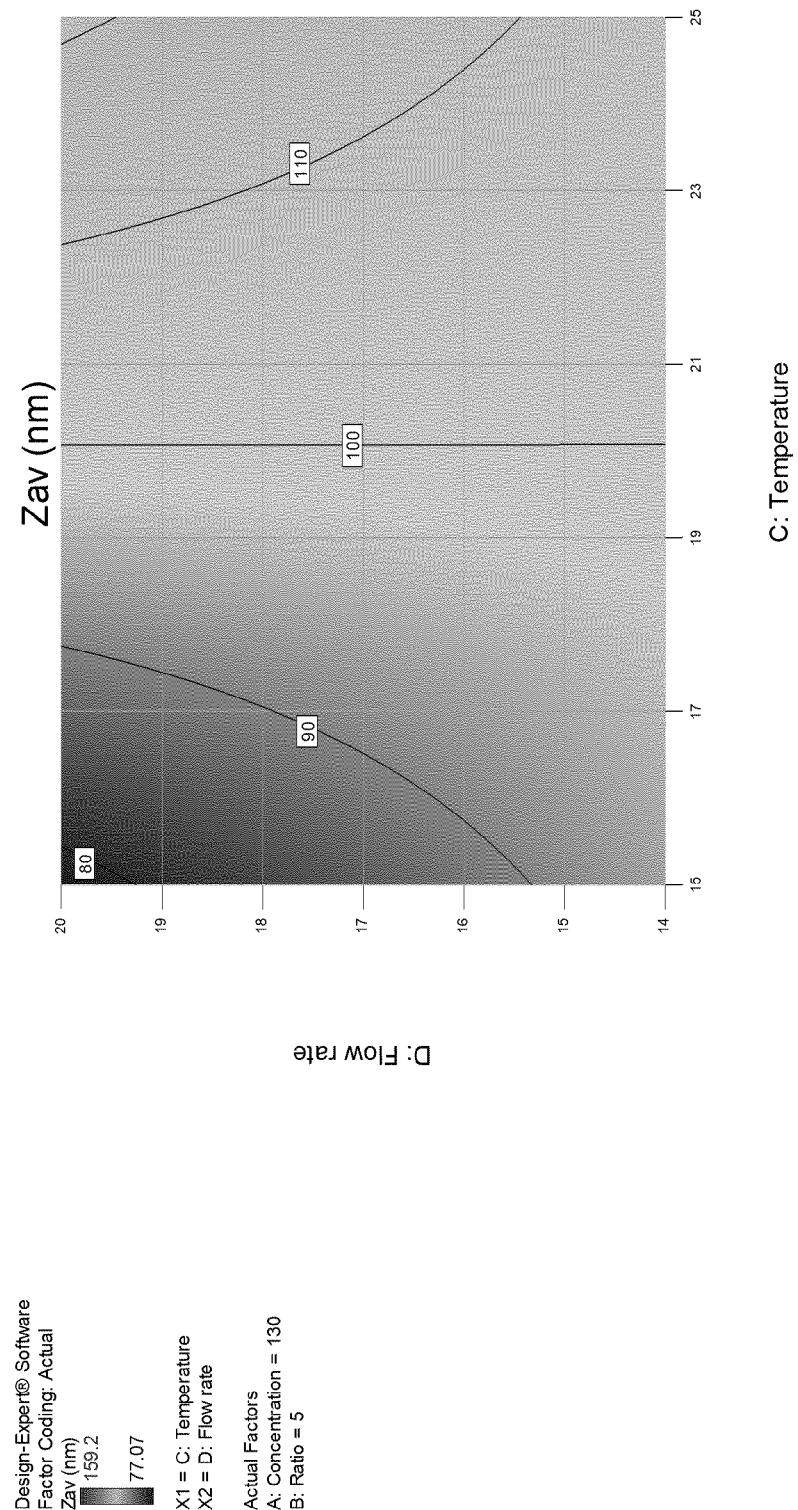
FIG. 13: Prediction of size at 130 mg/ml DOPC and ratio 5 (1:4 organic:aqueous phases)
Figure 14:
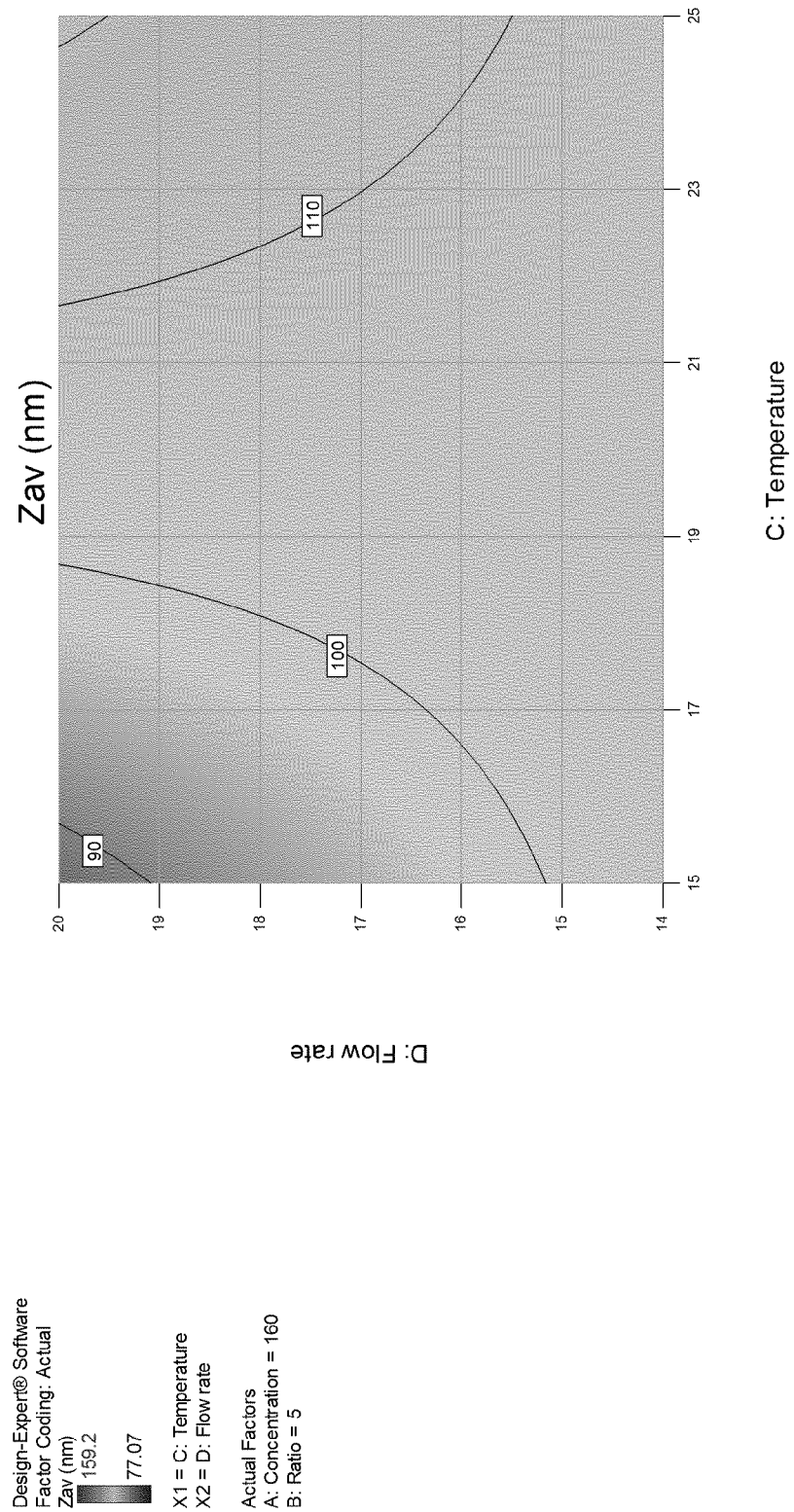
FIG. 14: Prediction of size at 160 mg/ml DOPC and ratio 5 (1:4 organic:aqueous phases)
Figure 15:
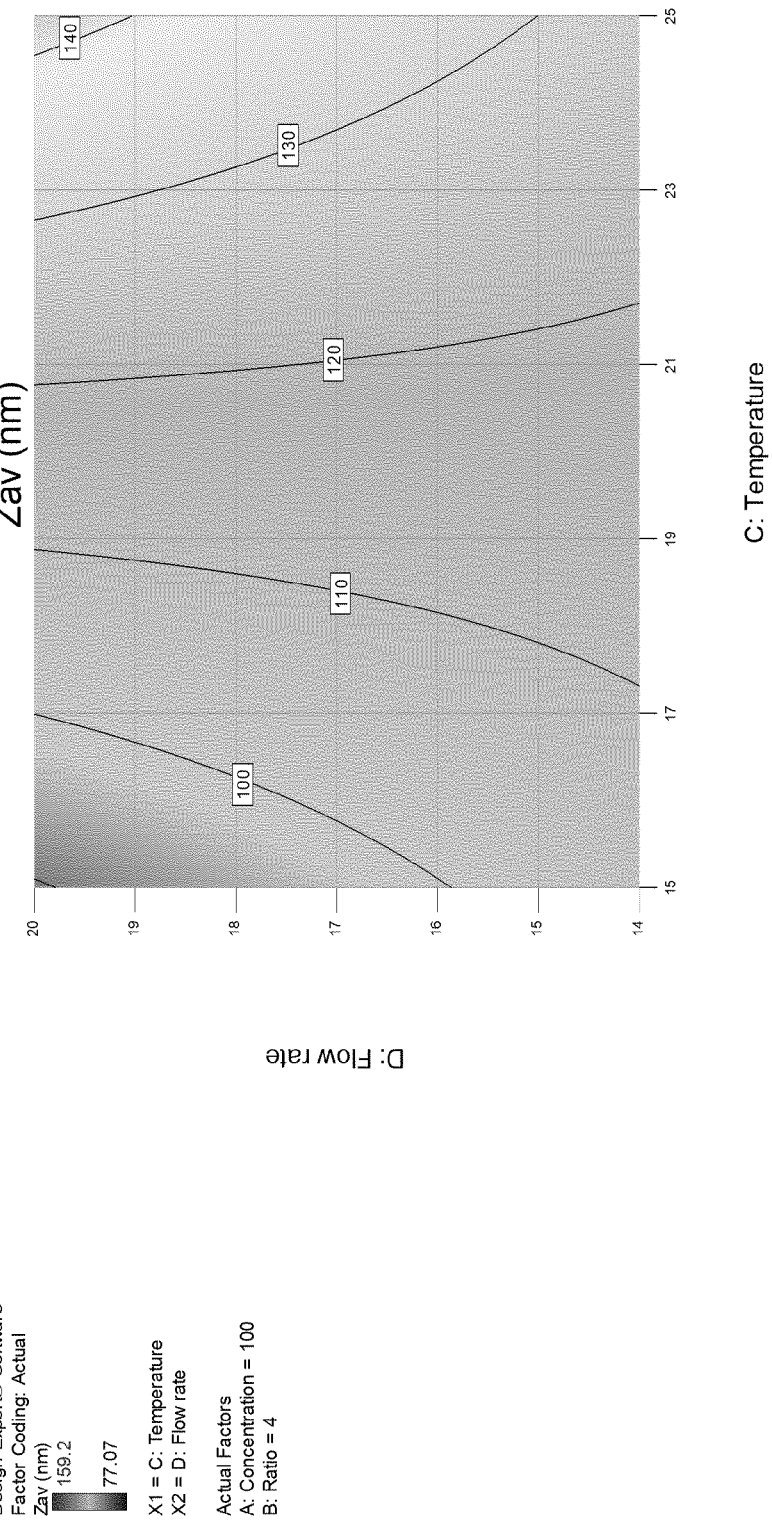
FIG. 15: Prediction of size at 100 mg/ml DOPC and ratio 4 (1:3 organic:aqueous phases)
Figure 16:
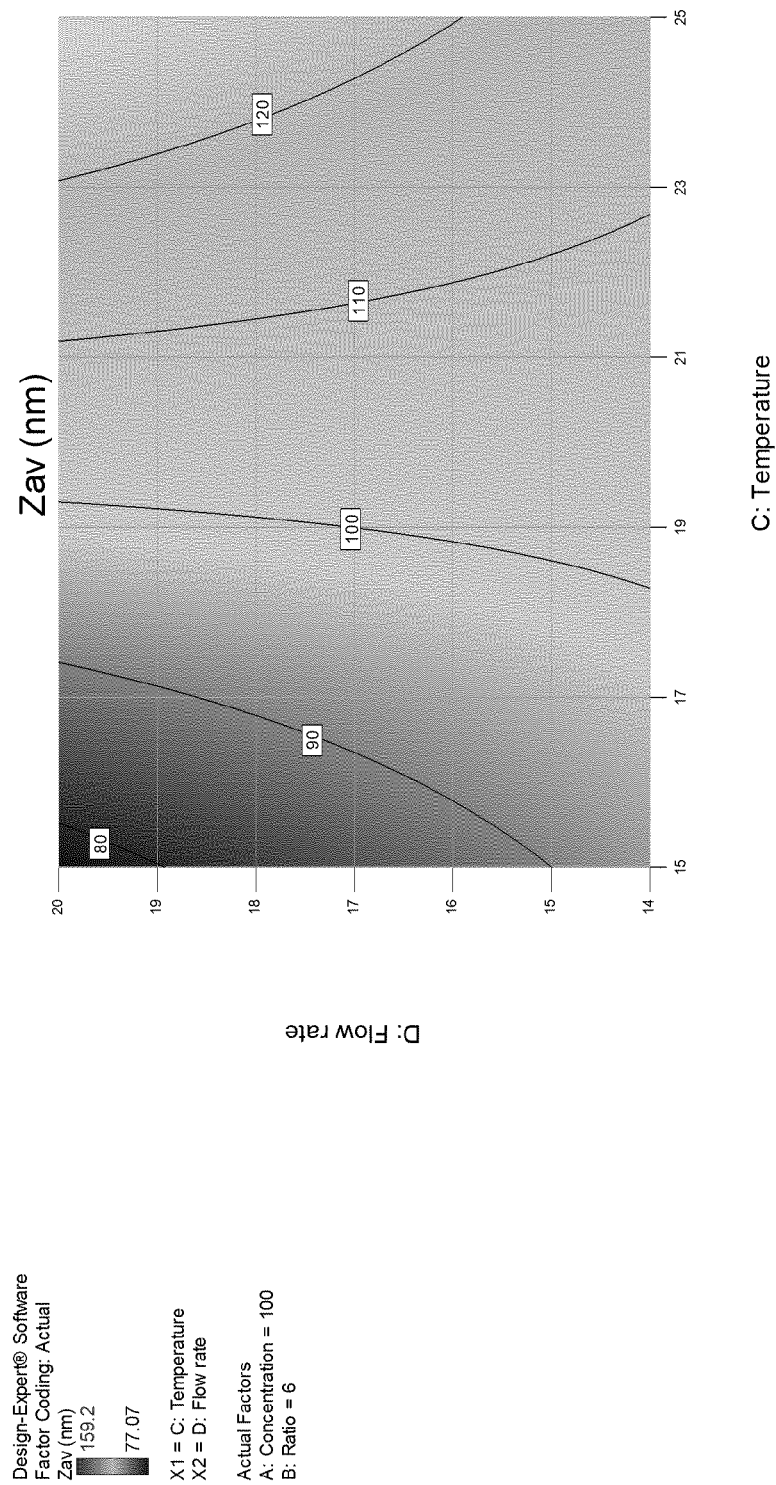
FIG. 16: Prediction of size at 100 mg/ml DOPC and ratio 6 (1:5 organic:aqueous phases)
Figure 17:
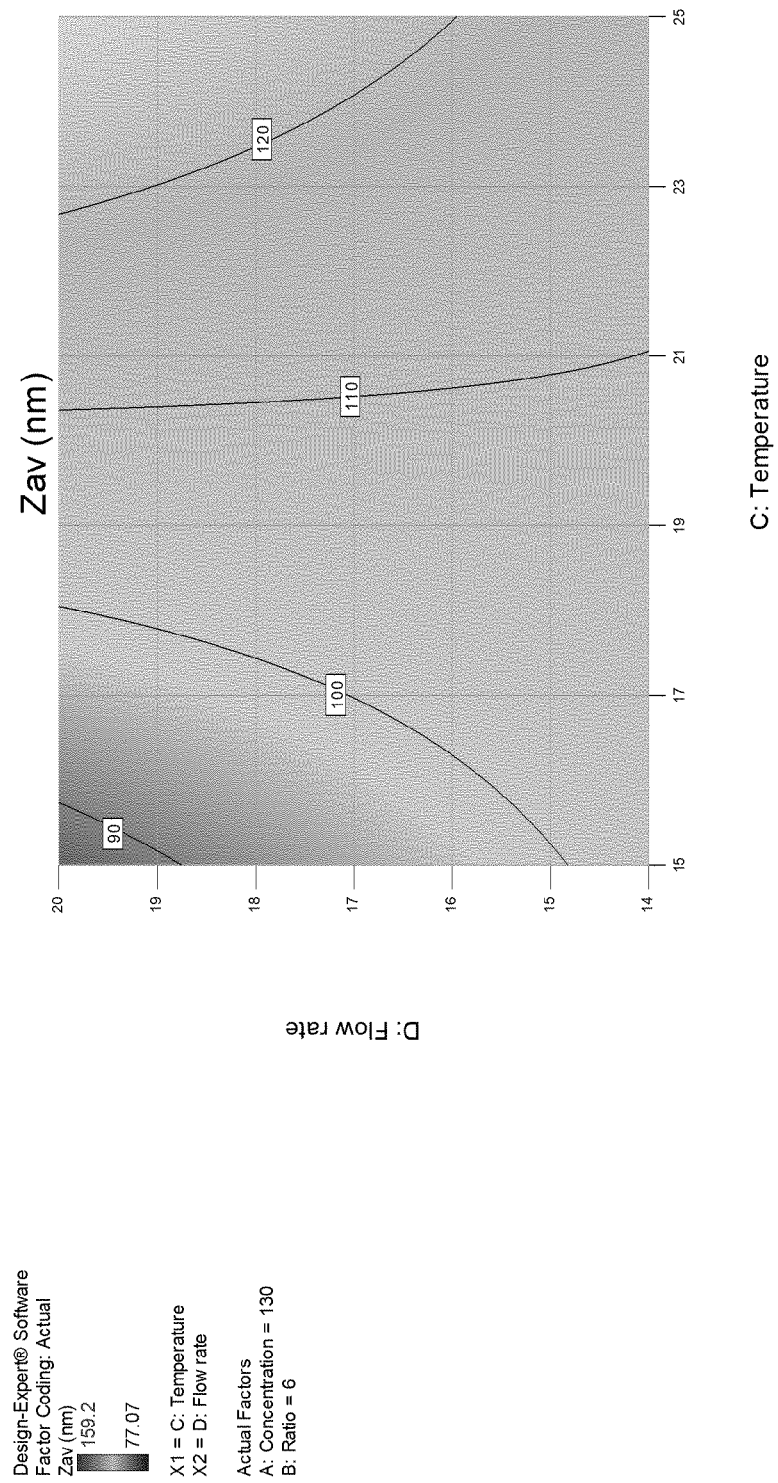
FIG. 17: Prediction of size at 130 mg/ml DOPC and ratio 6 (1:5 organic:aqueous phases)
Figure 18:
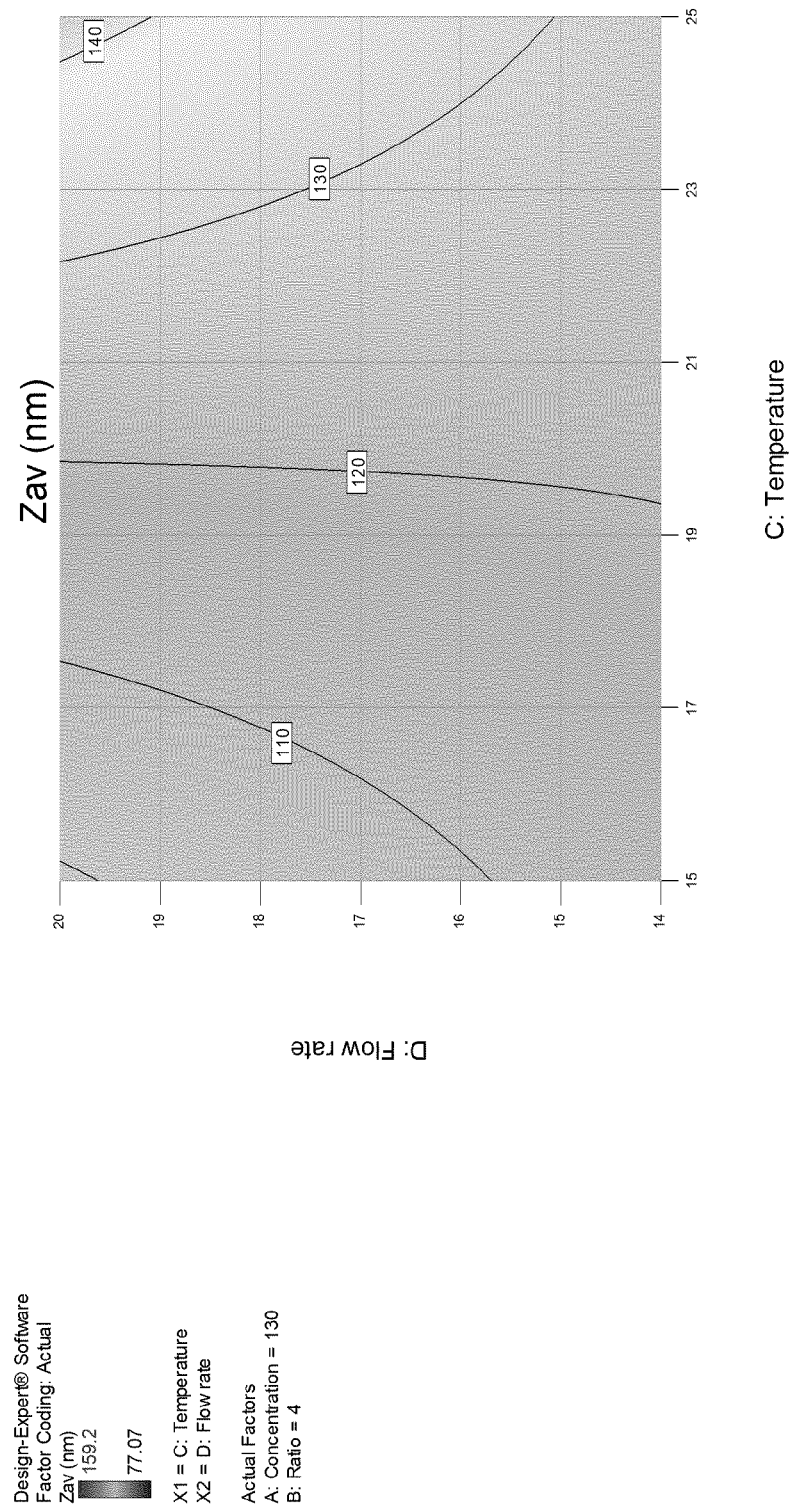
FIG. 18: Prediction of size at 130 mg/ml DOPC and ratio 4 (1:3 organic:aqueous phases)
Figure 19:
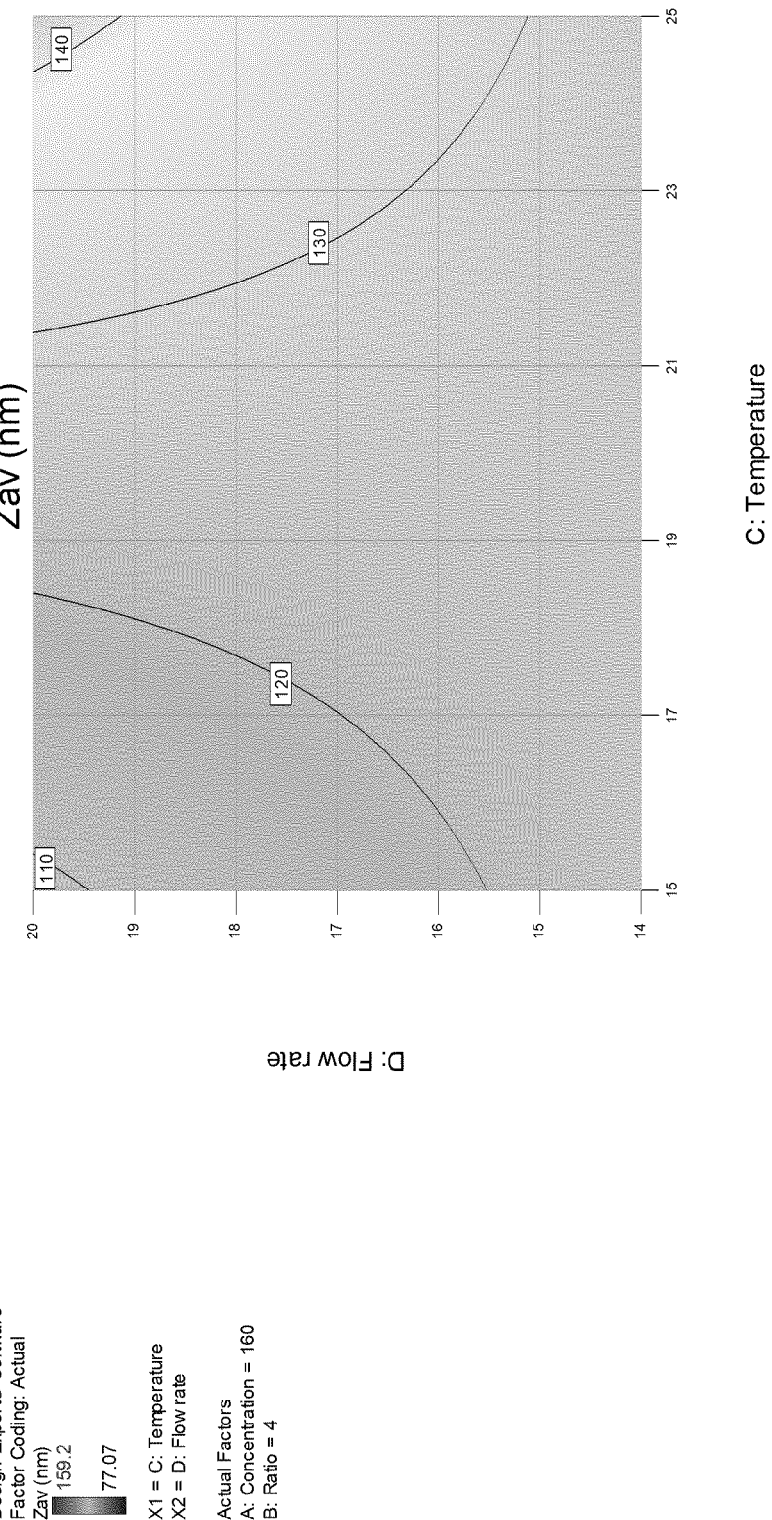
FIG. 19: Prediction of size at 160 mg/ml DOPC and ratio 4 (1:3 organic:aqueous phases)
Figure 20:
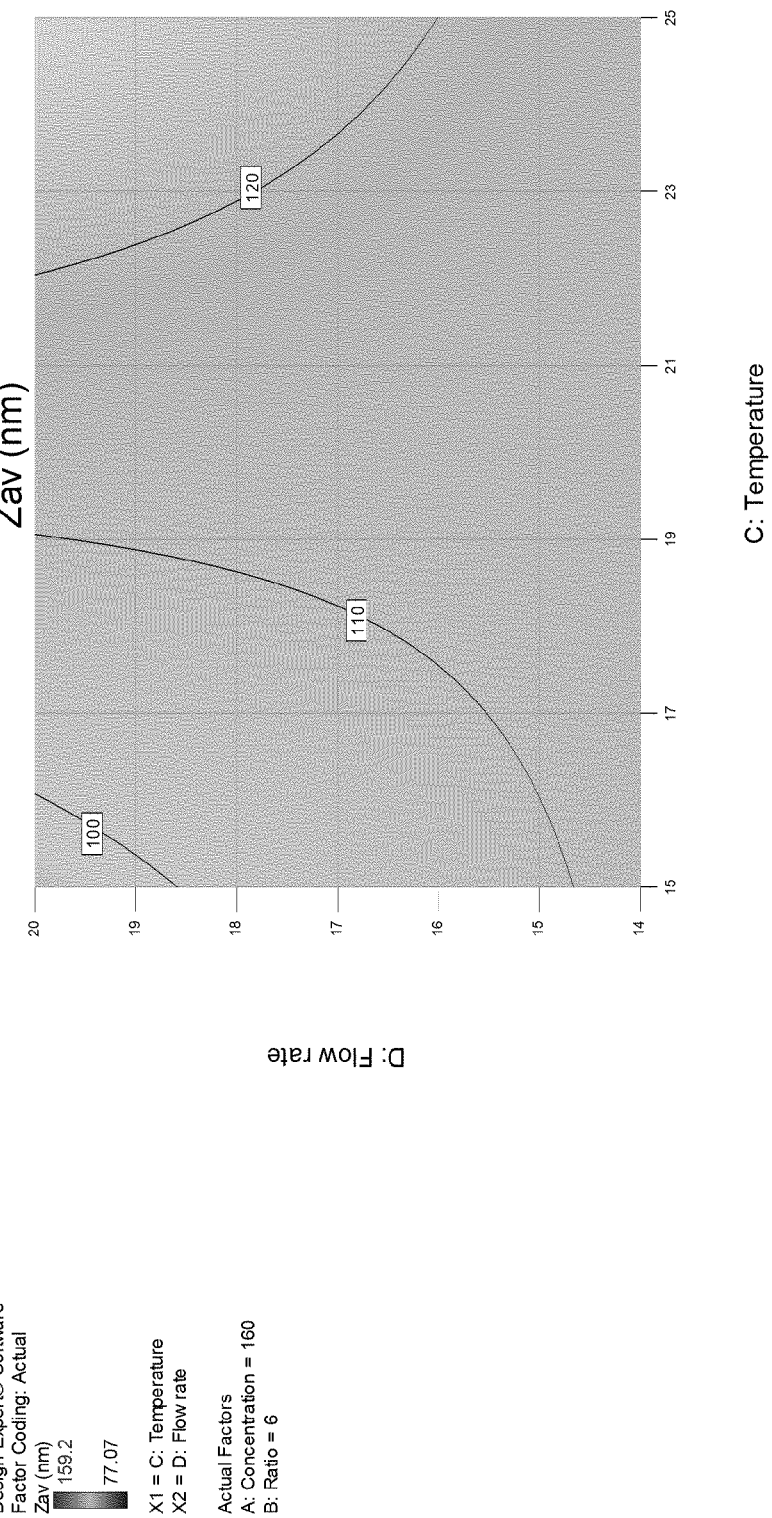
FIG. 20: Prediction of size at 160 mg/ml DOPC and ratio 6 (1:5 organic:aqueous phases)

No reliable prediction model for Pdl could be fit on the data, but significant correlation with Zav (correlation coefficient of 0.75). Zav<110 nM, yields Pdl<0.2 in 0.95 of the cases. The relationship between Zav and Pdl is illustrated in FIG. 11.

Modelling of Zav

Some significant effects of the different factors studied were observed, and a clear co-effect of concentration and temperature as well as temperature and flow rate.

Adj $R^2 = 0.80$

Pred $R^2$ 0.73

Other effects are considered as non-significant (p-value>5%)

TABLE 4 p-value for the parameters studied and cross-effect

| Factor | P-value |
|---|---|
| Concentration (A) | 0.008308 |
| Flow rate ratio (B) | 0.000998 |
| Temperature (C) | <0.0001 |
| Flow rate (D) | 0.957301 |
| Concentration and Temperature (AC) | 0.008791 |
| Temperature and flow rate (CD) | 0.000151 |
| Ratio squared (B^2) | <0.0001 |

FIGS. 12 to 20 represent the prediction of the Zav response at different fixed factors using the created model.

Confirmation of Model

Figure 21:
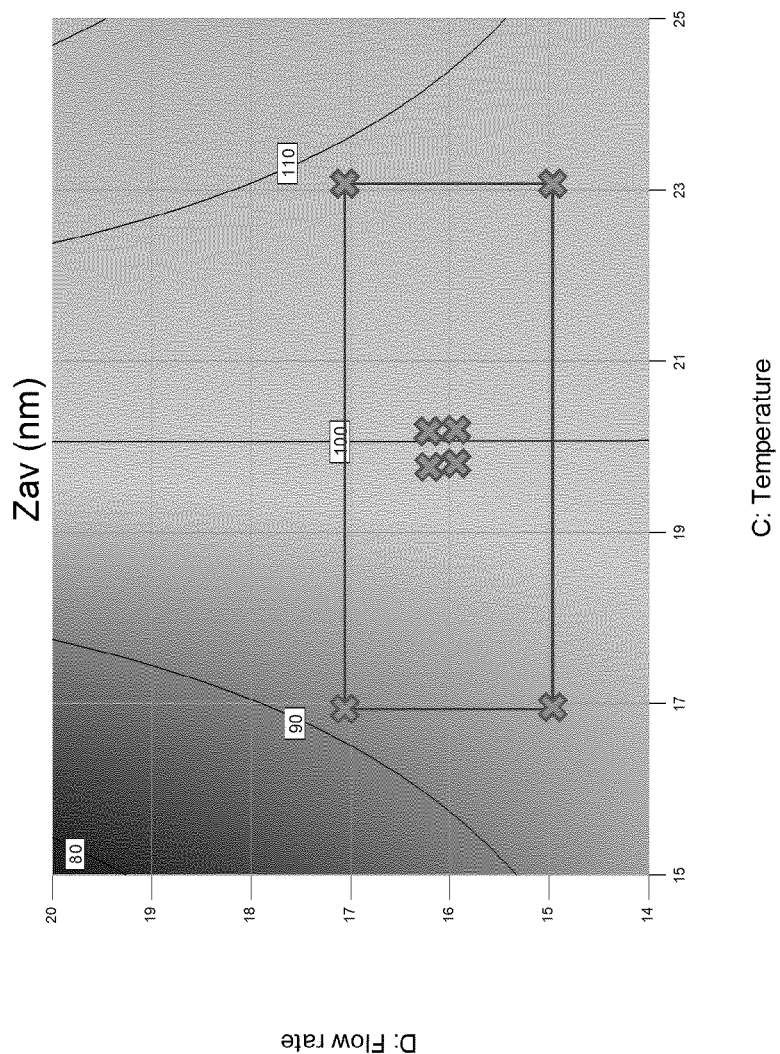
FIG. 21: Confirmation conditions tested at 130 mg/ml DOPC and ratio 5 (1:4 organic:aqueous phases)

As shown in FIG. 21, eight confirmatory runs were undertaken to test the capability of the model (all runs at 130 mg/ml DOPC and flow rate ratio of 5 (1:4 organic:aqueous). The obtained results are in good agreement with the model, with all results falling in the expected range of 90-110 nm.

TABLE 5

Confirmation results

| Run | Temperature (° C.) | Total flow rate (ml/min) | Zav (nm) Predicted | Zav (nm) Measured | Pdl |
|---|---|---|---|---|---|
| 1 | 23 | 15 | 105 | 101 | 0.188 |
| 2 | 23 | 17 | 108 | 104 | 0.187 |
| 3 | 20 | 16 | 100 | 98 | 0.185 |
| 4 | 20 | 16 | 100 | 99 | 0.196 |
| 5 | 17 | 15 | 94 | 97 | 0.168 |
| 6 | 17 | 17 | 91 | 89 | 0.160 |
| 7 | 20 | 16 | 100 | 96 | 0.173 |
| 8 | 20 | 16 | 100 | 95 | 0.176 |

Conclusion

To optimise the process in terms of temperature, run time and harvest volume, a ratio of 1:4 (organic:aqueous) with a DOPC concentration of around 130 mg/ml, flow rate between 14 and 17 ml/min and temperature between 16 and 25° C. appears best for obtaining liposomes in the region of 95-120 nm (i.e. around 100 nm).

Specific parameters are 130 mg/ml DOPC in 80:20 ethanol:IPA, flow rate ratio 1:4 (organic:aqueous), total flow rate 16 ml/min and temperature 20° C.

Table 3 presents the standard deviation (SD) and CV for Zav and Pdl. It shows very low CV representing a good repeatability.

Example 5: Adaptive Immune Responses

Method

Adjuvant Preparation

Liposomes were prepared using the single mixing chamber apparatus described previously. Organic phase comprising DOPC (120 mg/ml), cholesterol (30 mg/ml) and 3D-MPL (6 mg/ml) in 80/20 ethanol/IPA was mixed with aqueous phase containing QS-21 (1.5 mg/ml) in water for injection under conditions of a total flow rate of 18 ml/min and a flow rate ratio of 5 (1:4 organic:aqueous). The organic phase was maintained at 20° C. The aqueous phase was maintained at 15° C.

Solvent was removed by dialysis and the resulting concentrate diluted to provide the final adjuvant preparation.

Vaccination 6-8 week old-female C57Bl6 mice (22/group) were injected twice with a 14-day interval with gE antigen formulated with microfluidic produced liposomes with 3D-MPL and QS-21. A control group of 5 mice received gE with buffer alone.

The final adjuvant preparation was diluted and mixed with gE as necessary to provide the vaccination mixture. Two doses of adjuvant were evaluated (0.4 and 0.1 ug of both 3D-MPL and QS-21 per animal, corresponding to 1/125 and 1/500 of a typical 50 ug human dose (HD), respectively). Each animal received 5 ug of gE. The injection volume was 20 ul.

Spleen and sera were collected and analysed for T and B cell responses, respectively, 7 days post the second immunisation (day 21).

ICS (Intracellular Cytokine Staining)

Spleens were collected in RPMI medium and dissociated using a potter tissue grinder (homogenizer) using two up and down strokes. Homogenized samples were transferred to 50 ml polypropylene tubes. Fibrous material was removed by filtration through a 100 uM nylon cell strainer. Cells were then washed, counted and re-suspended at $10^7$ cells per ml.

ICS is the technology which allows the quantification of antigen specific T lymphocytes on the basis of cytokine production.

Lymphoid cells are re-stimulated overnight (O.N) with in vitro with peptides gE or medium in the presence of a protein transport inhibitor (brefeldin A). These cells are then processed by conventional immunofluorescent procedure using fluorescent antibodies (extracellular staining: CD4, CD8; intracellular staining: TNF-alpha, IFN-gamma and IL2).

Results are expressed as a frequency of cytokine positive cells within CD4 cell populations after subtraction of the medium condition for each mouse. The statistical analysis was done on the population that showed expression of at least two cytokines (IL2, IFN-alpha or TNF-alpha).

ELISA

Anti-gE total IgG were measured by ELISA. 96 well-plates were coated with antigen overnight at 4° C. The plates were then washed and saturated with saturation buffer for 1 hour at 37° C. After, 100 ul of diluted mouse serum or standard or control was added and incubated for 1h30 at 37° C. After wash, the plates were incubated for 1 hour at 37° C. with 100 μl anti mouse IgG-Biotinylated. After wash, the plates were incubated for 30 min at 37° C. with 100 ul Streptavidin-POD conjugate. After wash, 100 ul of TMB per well was added and the plates were kept in the dark at room temperature for 15 minutes. To stop the reaction, 100 ul of $H_2SO_4$ 0.4N was added per well. The absorbance was read at a wavelength of 450/630 nm by an Elisa plate reader. Results were calculated using the softmax-pro software.

Results

Liposomes had a diameter of 95.5 nm, PdI of 0.184. The final adjuvant preparation had a DOPC content of 2.2 mg/ml, cholesterol content of 0.58 mg/ml, QS-21 content of 119 ug/ml and 3D-MPL content of 90 ug/ml.

3D-MPL (6.5 mg/ml) in 80/20 ethanol/IPA was mixed with aqueous phase containing QS-21 (1.625 mg/ml) in water for injection under conditions of a total flow rate of 16 ml/min and a flow rate ratio of 5 (1:4 organic:aqueous). The organic phase was maintained at 20° C. The aqueous phase was maintained at 20° C.

Solvent was removed by dialysis and material was sterile filtered.

Figure 24:
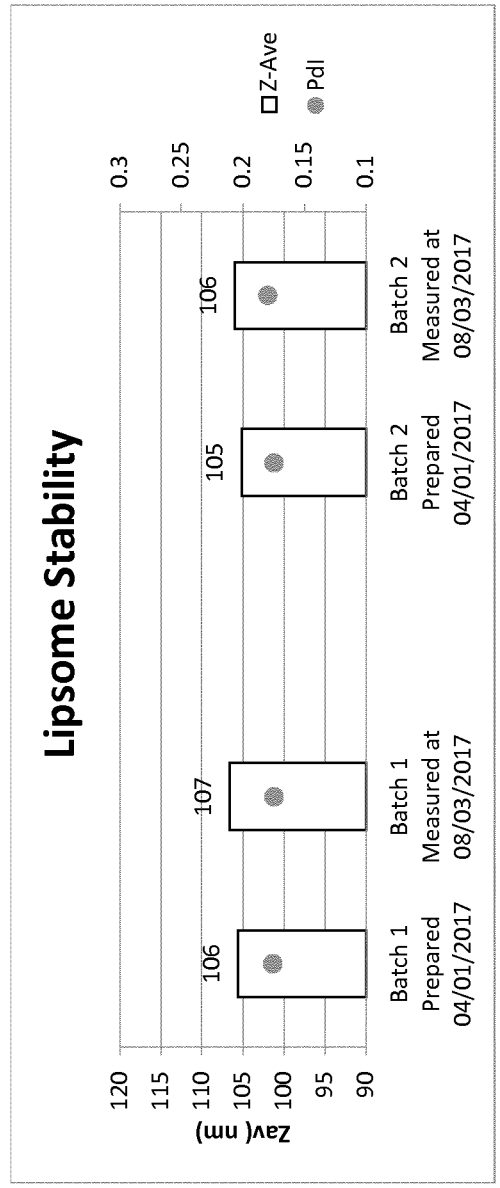
FIG. 24: Microfluidic produced-liposome size and Pdl stability after storage

The results are shown in FIG. 24, indicating that liposomes produced using microfluidics are substantially unchanged after storage for 2 months at 4° C.

Example 7: Upscaling of the Process

Figure 25:
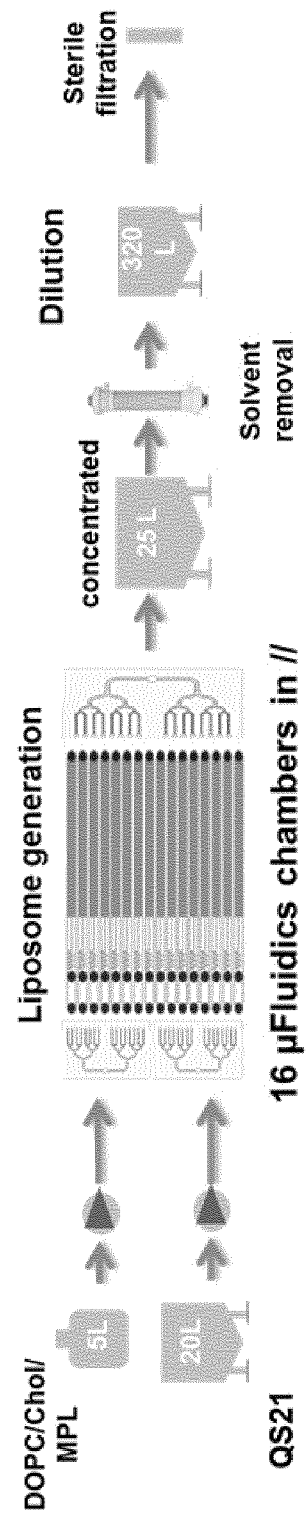
FIG. 25: Schematic of a commercial scale multichamber process

The aim of this example was to test the scaling up of the process in order to produce commercial scale batches of adjuvant using a microfluidic process. A single batch of 320 L of adjuvant was prepared in a production cycle suitable for one working day (FIG. 25). The number of mixing chambers used was 16.

Manifold Evaluation

In order to distribute the organic and aqueous phases into the 16 mixing chambers, the distribution manifold should ideally provide a homogenous flow distribution. Practical limitations mean that perfect distribution is not possible, but excessive variation must be avoided. Excessive variation in flow can lead to lead to inhomogeneity in final product and potentially a product which falls outside target specification.

A theoretical estimation of the component content in the final product was calculated depending on variations in the flow distribution. Table 6 shows that variations below 5% do not substantially affect the component content in the final product which stay in the target specification range.

Above 6% variation, the content of 3D-MPL is close to the upper acceptable boundary and exceeds this boundary with further increases in the percentage of variation.

TABLE 6

Expected component content in the final product with variation of flow rate

| % Var | % (Aq-Org) | ml/min Aq | ml/min Org | Ratio | ml/min Total Flow | Final Quantity (mg/ml) | | | |
|---|---|---|---|---|---|---|---|---|---|
| | | | | | | DOPC | Chol | 3D-MPL | QS21 |
| 0 | 100-100 | 12.8 | 3.2 | 5.00 | 16 | 2.0 | 0.50 | 0.100 | 0.100 |
| 2 | 102-98 | 13.06 | 3.14 | 5.16 | 16.2 | 1.9 | 0.48 | 0.097 | 0.101 |
| 2 | 98-102 | 12.54 | 3.26 | 4.84 | 15.8 | 2.1 | 0.52 | 0.103 | 0.099 |
| 5 | 105-95 | 13.44 | 3.04 | 5.42 | 16.5 | 1.8 | 0.46 | 0.092 | 0.102 |
| 5 | 95-105 | 12.16 | 3.36 | 4.62 | 15.5 | 2.2 | 0.54 | 0.108 | 0.098 |
| 6 | 106-94 | 13.57 | 3.01 | 5.51 | 16.6 | 1.8 | 0.45 | 0.091 | 0.102 |
| 6 | 94-106 | 12.03 | 3.39 | 4.55 | 15.4 | 2.2 | 0.55 | 0.110 | 0.098 |
| 8 | 108-92 | 13.82 | 2.94 | 5.70 | 16.8 | 1.8 | 0.44 | 0.088 | 0.103 |
| 8 | 92-108 | 11.78 | 3.46 | 4.41 | 15.2 | 2.3 | 0.57 | 0.113 | 0.097 |
| 10 | 110-90 | 14.08 | 2.88 | 5.89 | 17.0 | 1.7 | 0.42 | 0.085 | 0.104 |
| 10 | 90-110 | 11.52 | 3.52 | 4.27 | 15.0 | 2.3 | 0.59 | 0.117 | 0.096 |

Figure 23:
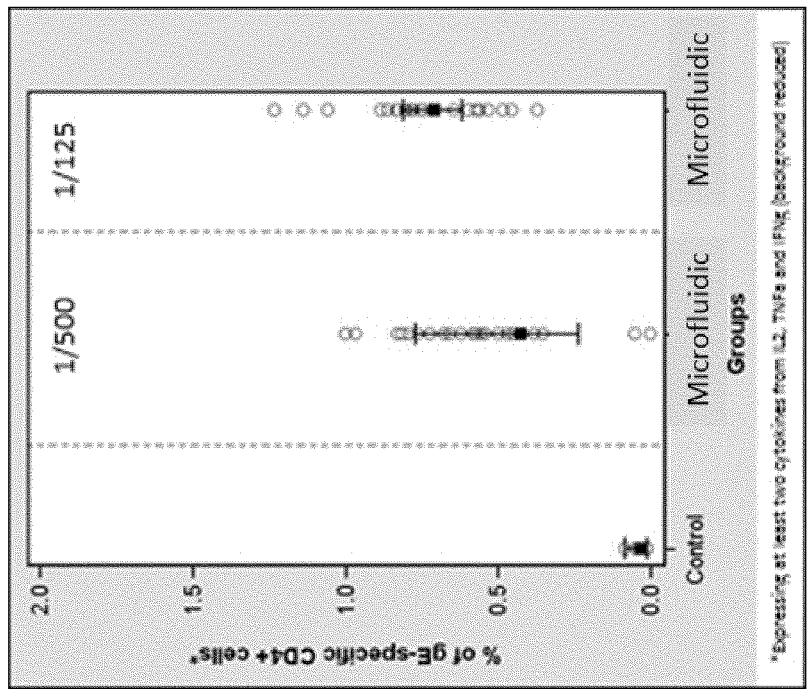
FIG. 23: Percentage of gE-specific CD4+ T cells
Figure 22:
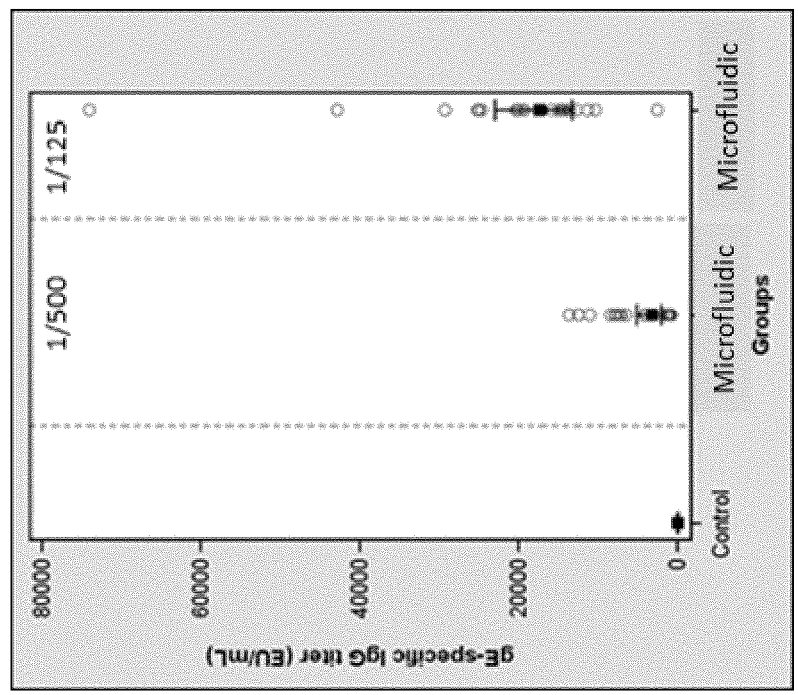
FIG. 22: gE-specific IgG titer

ELISA results are shown in FIG. 22 and ICS results in FIG. 23.

Conclusions

Microfluidics-produced liposomes in conjunction with TLR4 agonist and saponin were capable of adjuvanting the cellular and antibody responses to an exemplary antigen.

Example 6: Stability of Microfluidic Liposomes

Figure 26:
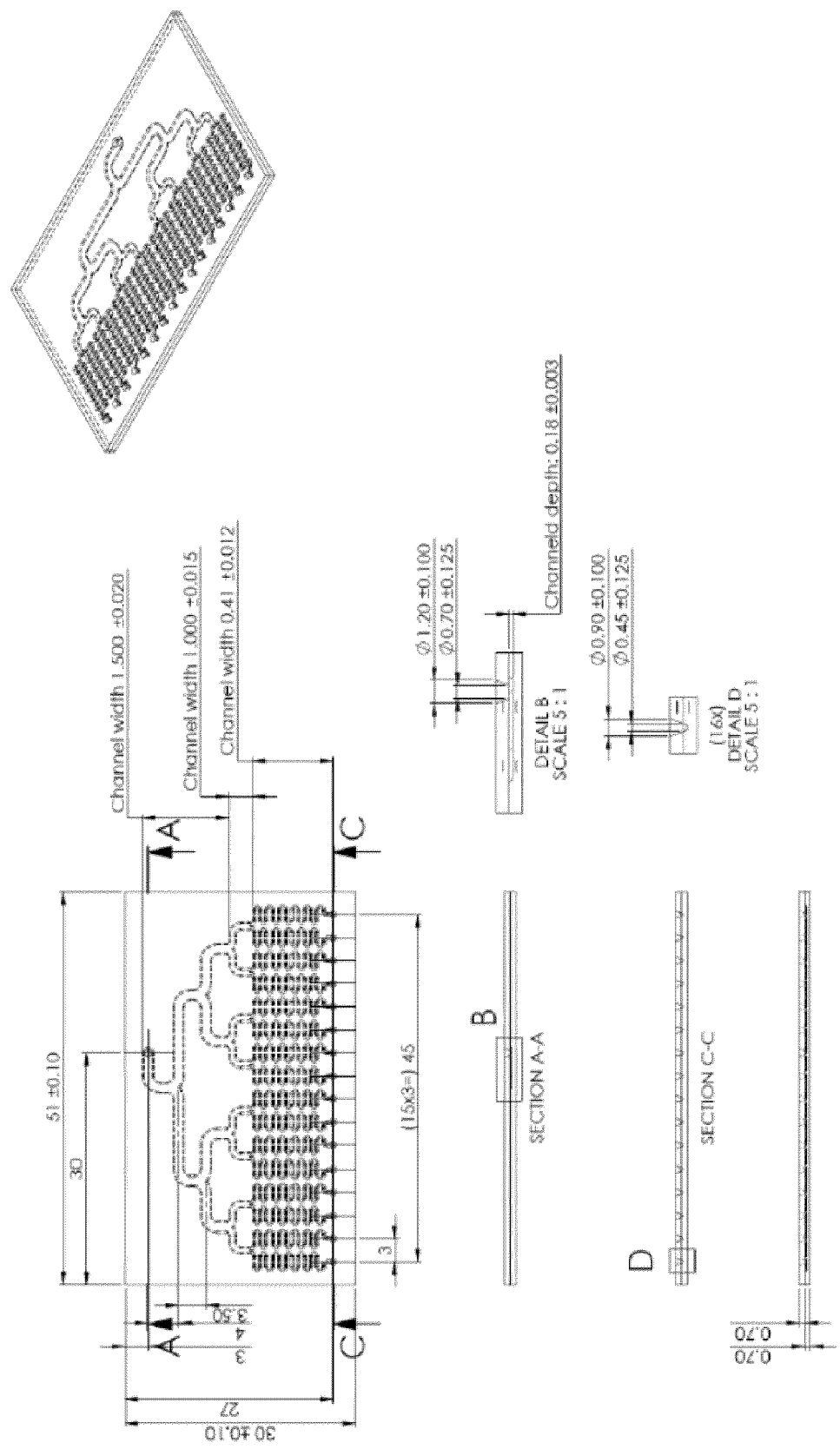
FIG. 26: Schematic of initial manifold design
Figure 27:
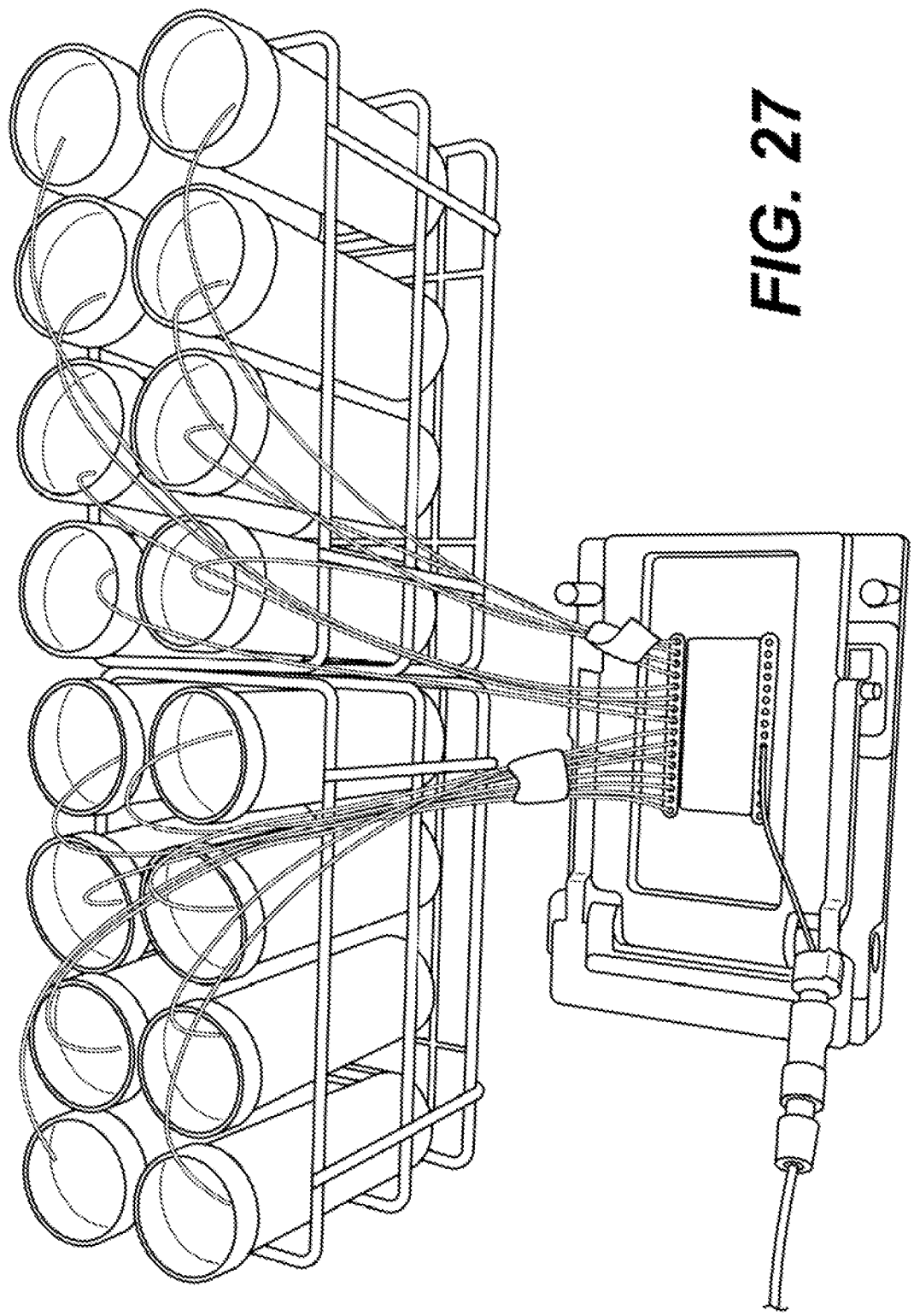
FIG. 27: Photograph of setup for testing of the initial manifold

Liposomes were prepared using the single mixing chamber apparatus described previously. Organic phase comprising DOPC (130 mg/ml), cholesterol (32.5 mg/ml) and Procedure Applied for Manifold Testing The inlet of an initial manifold design (FIG. 26) was connected to ISCO pumps filled with water. At each of the 16 exits of the manifold 20 cm of ETFE (Ethylene tetrafluoroethylene) tubing (1/16", 0.04" ID) was connected and placed into a 50 ml Falcon™ tube (FIG. 27). Each Falcon™ tube was weighed before the experiment. Tubing (inlet & exit) and the manifold were then filled with water to eliminate air bubbles.

The system was run for 2 min at ~200 ml/min total flow rate. After the 2 min period, each Falcon™ tube was weighed to calculate the exact mass of water delivered. The % of flow variation was calculated: weight of channel X (1 to 16) divided by the measured average weight.

Figure 28:
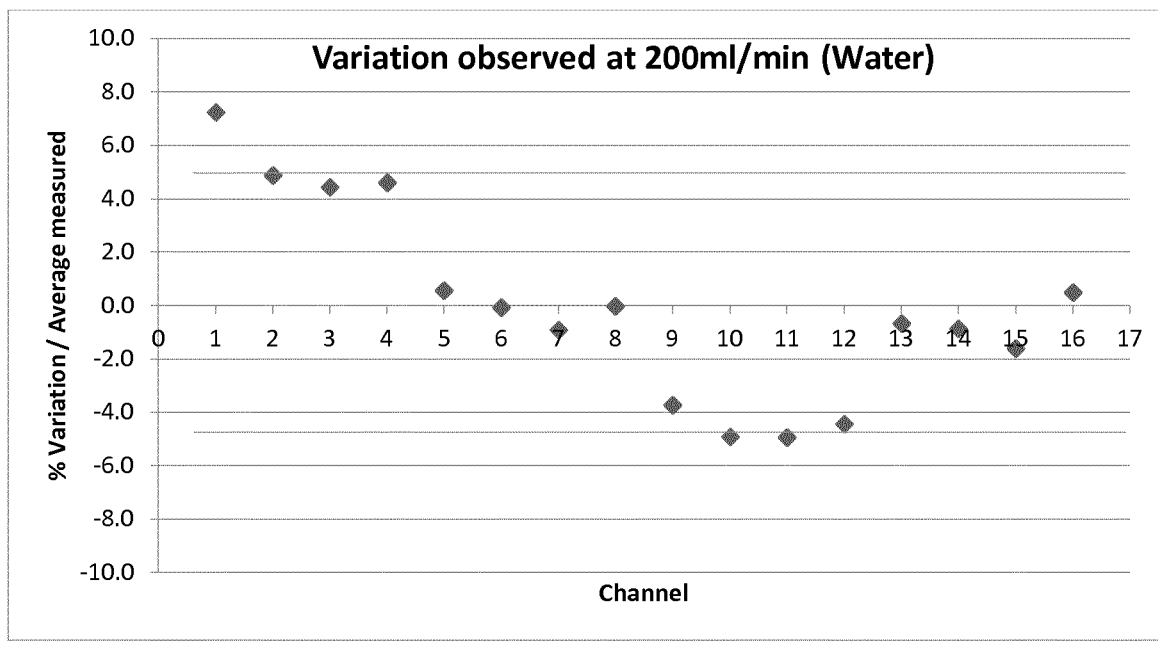
FIG. 28: Observed flow rate variation for initial manifold at 200 ml/min
Figure 29:
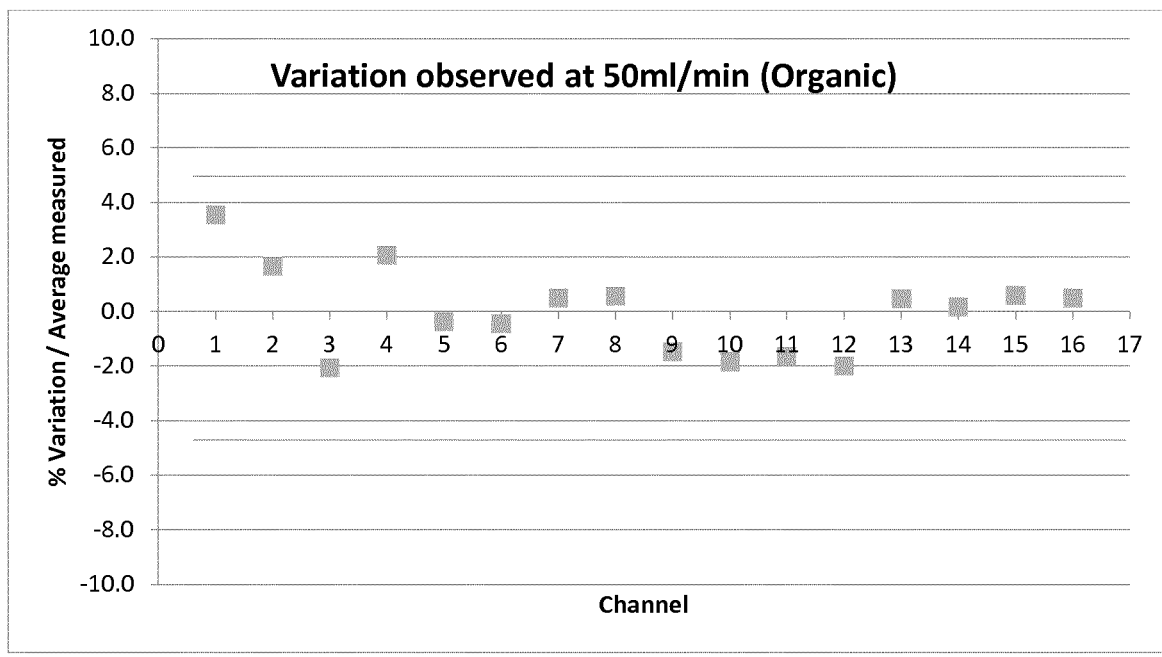
FIG. 29: Observed flow rate variation for initial manifold at 50 ml/min

The initial manifold was tested at 200 ml/min with water and also at 50 ml/min with a mix of ethanol and isopropanol. Results (FIG. 28 & FIG. 29) show the variation across the channels: at a high total flow rate (~200 ml/min), one was above the acceptable variation limit of 5% (Channel 1) but others were close to this limit (Channels 2, 3, 4, 9, 10, 11 and 12). For the lowest flow rate (~50 ml/min) the variation is below 5% but shows the same general trend.

Figure 30:
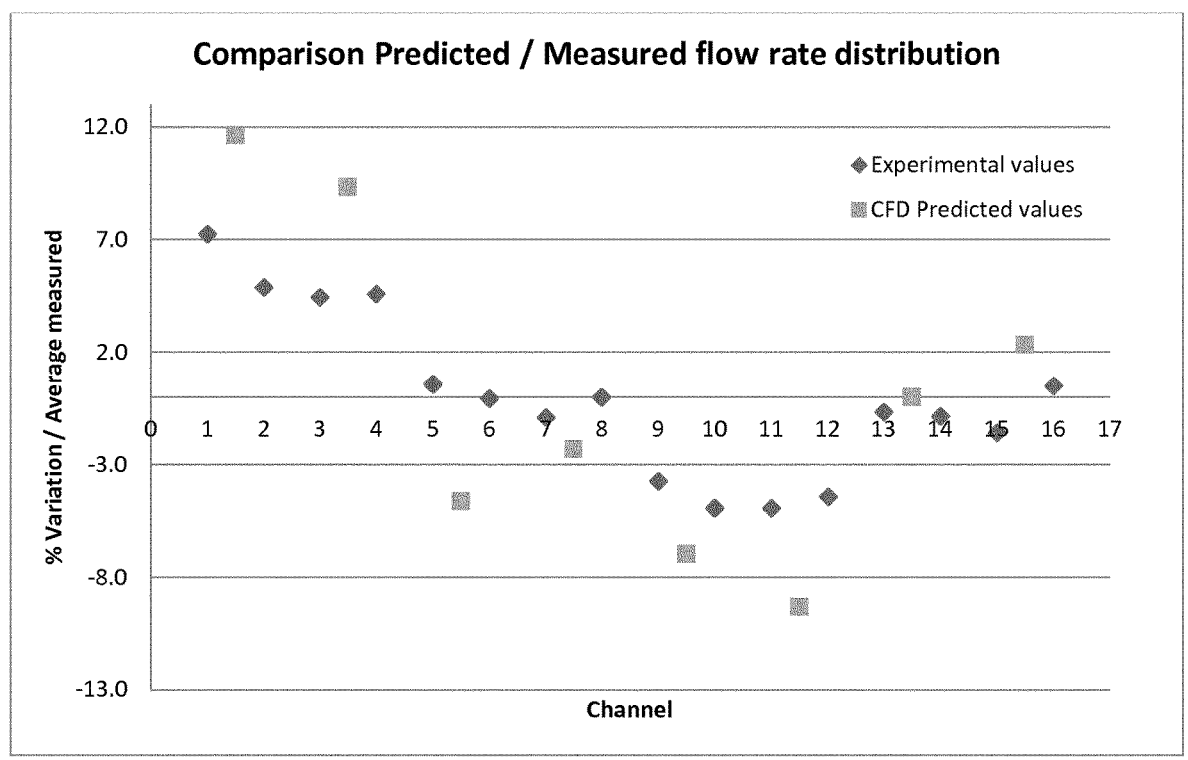
FIG. 30: Graph comparing the predicted values and the measured values of flow rate distribution

Following those results, CFD (Computational fluid dynamics) analysis was performed to predict the flow distribution along each segment of the manifold. The analysis showed that the initial elbow was inducing flow rate differences in the subsequent branches. These differences remained along the final branches. The predicted variation was plotted against the observed experimental values (from 200 ml/min testing) and shows the same general trends (FIG. 30).

The experimental finding for the first manifold that it was not able to distribute with desired homogeneity was confirmed with the CFD analysis.

Figure 31:
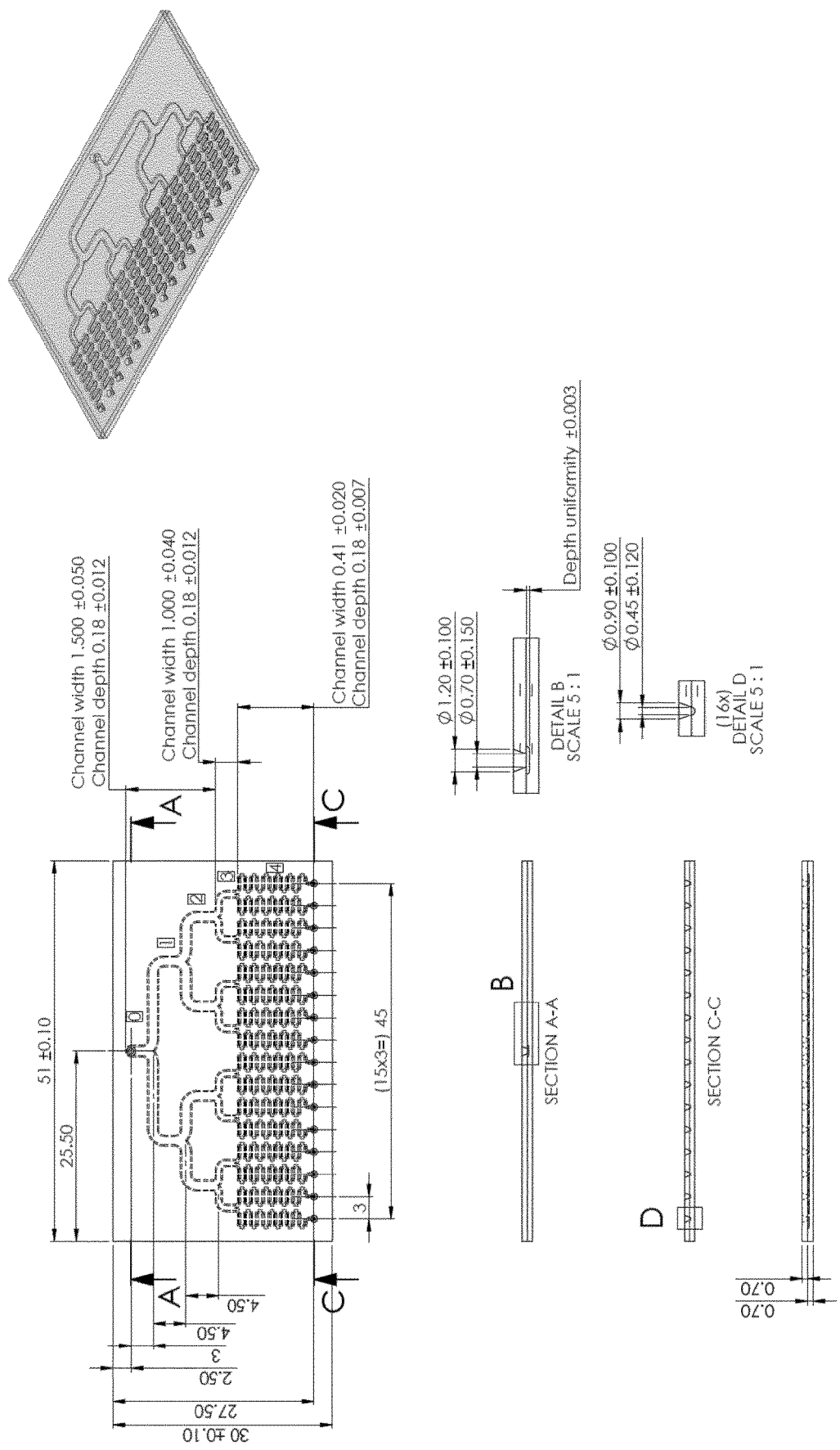
FIG. 31: Schematic of improved manifold design

Following these results, CFD was used as a tool to support the design of an improved second generation manifold (FIG. 31). Investigations led to removal of the initial elbow, shortening of first channel length, increasing the second and third channel lengths. Under these circumstances the velocity profile is more constant and circulations zones were removed almost completely.

Test of Improved Manifold

Figure 32:
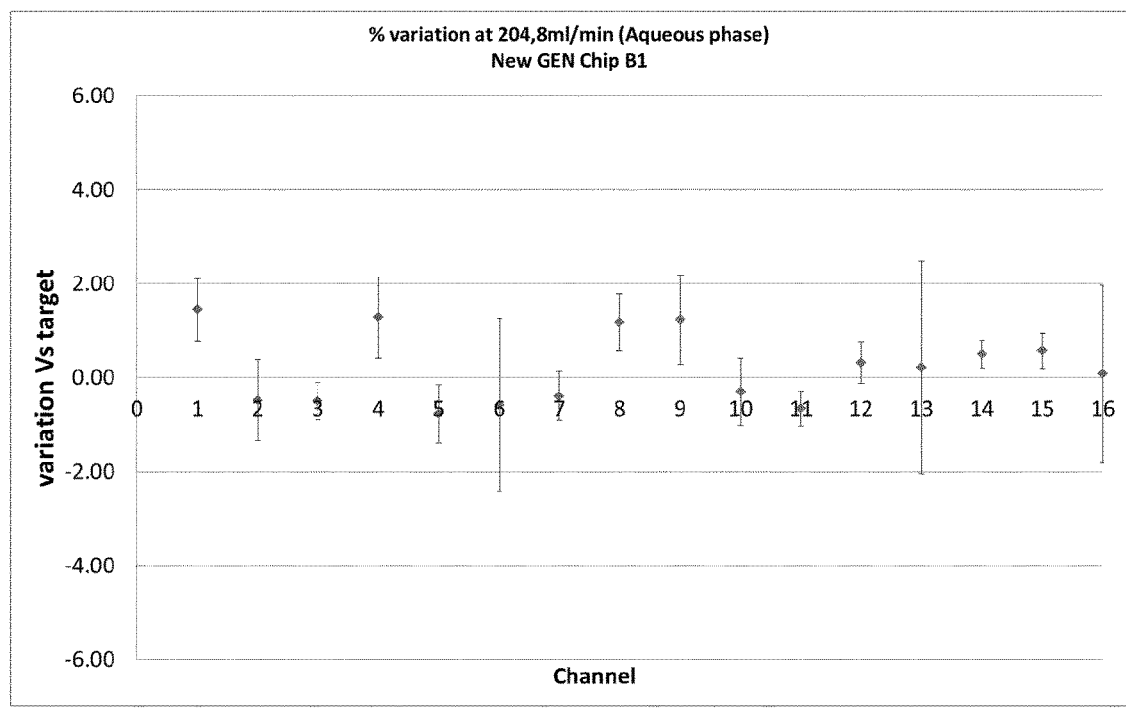
FIG. 32: Flow rate variation from average by each channel for improved manifold unit 1 ('B1')
Figure 33:
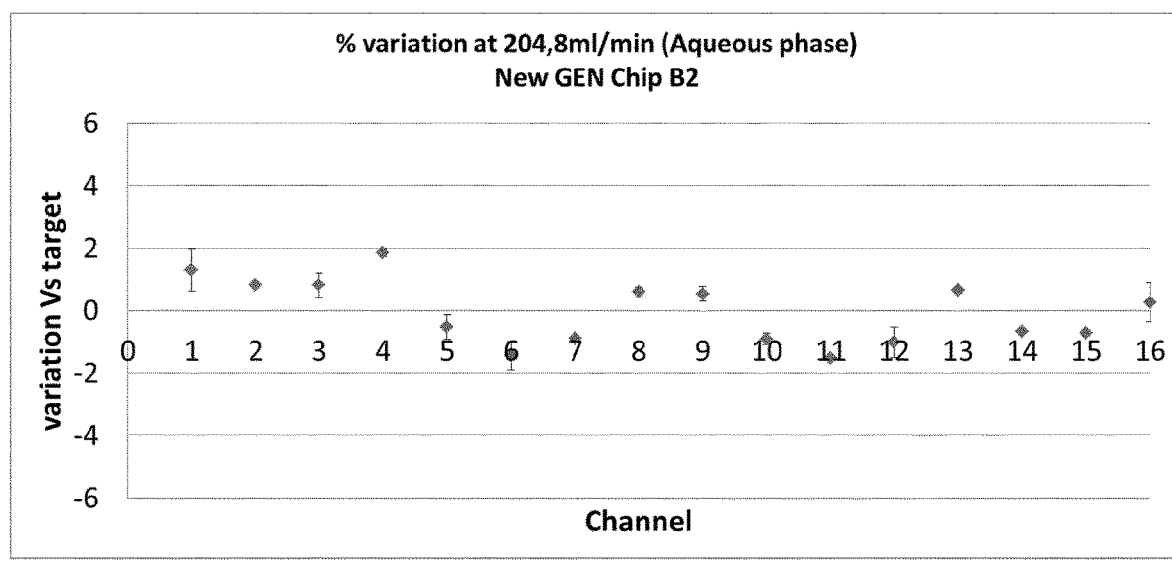
FIG. 33: Flow rate variation from average by each channel for improved manifold unit 2 ('B2')
Figure 34:
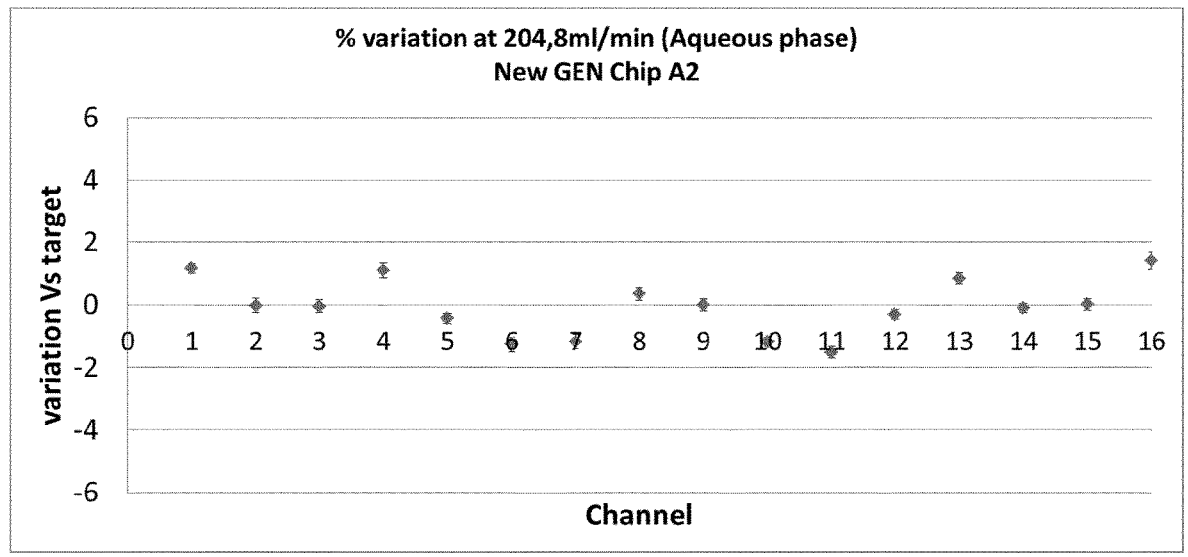
FIG. 34: Flow rate variation from average by each channel for improved manifold unit 3 ('A2')

The second manifold was tested with a similar procedure (12.8 ml/min/channel=204.8 total flow rate) and reproduced three times on each of three manifolds (designated B1, B2 and A2). FIGS. 32-34 show the experimental results obtained. In all cases the variation of individual channels was below the desired limit of 5%, in many cases the variation in measured flow rate was less than 2% from the average.

Liposome Production

Using the improved manifold, an experiment was performed to confirm that liposomes with the same profile as those produced with a single mixing chamber could be produced at commercial scale.

For the experiments, ISCO 1000D & 500D pumps were used in tandem. Only one cylinder of each pump was used, due to the limited run time. The pump heating jacket was connected to a waterbath (Julabo F33), one waterbath per pump. The control of the temperature was monitored using certified probes.

Two improved manifolds were connected to each pump at the inlet and to 2 microchips containing 8 mixing chambers each to provide a total of 16 mixing chambers in parallel. Tubing used was ETFE 1/16 0.04" ID, 29.5 cm in length. 29.5 cm of ETFE tubing (1/16 0.02" ID) was connected at the exit of each mixing chamber. The temperature of the prototype was not controlled directly but the apparatus was placed into controlled temperature area (at 20° C.) and allowed to acclimatise before any experiment.

The pumps were rinsed twice and emptied before filling with the appropriate organic (DOPC at 130 mg/ml, Cholesterol at 32.5 mg/ml solubilized in 80/20 Ethanol/Isopropanol) and aqueous phases (water for injection). The pumps were then primed to eliminate air in the system before connection to the distribution manifolds. Flow rates were set at 51.2 ml/min for the organic phase and 204.8 ml/min for the aqueous phase. When the system was primed and clear of air the first 2 ml from each chamber was discarded and the outlet of each chamber then harvested in in 16 separate containers (run time<30 seconds). 500 ul of product from each channel were pooled and subjected to DLS measurement after dilution 130× in PBS at pH 6.1.

After the run was performed on the multichambered prototype, the tubing from the pumps was disconnected from the multichambered prototype and connected to one mixing chamber. Flow rates were adapted to organic 3.2 ml/min and aqueous 12.8 ml/min. When the system was stabilized (no air), the first 2 ml exiting the mixing chamber was discarded and the subsequent ~2 ml harvested.ml).

Figure 35:
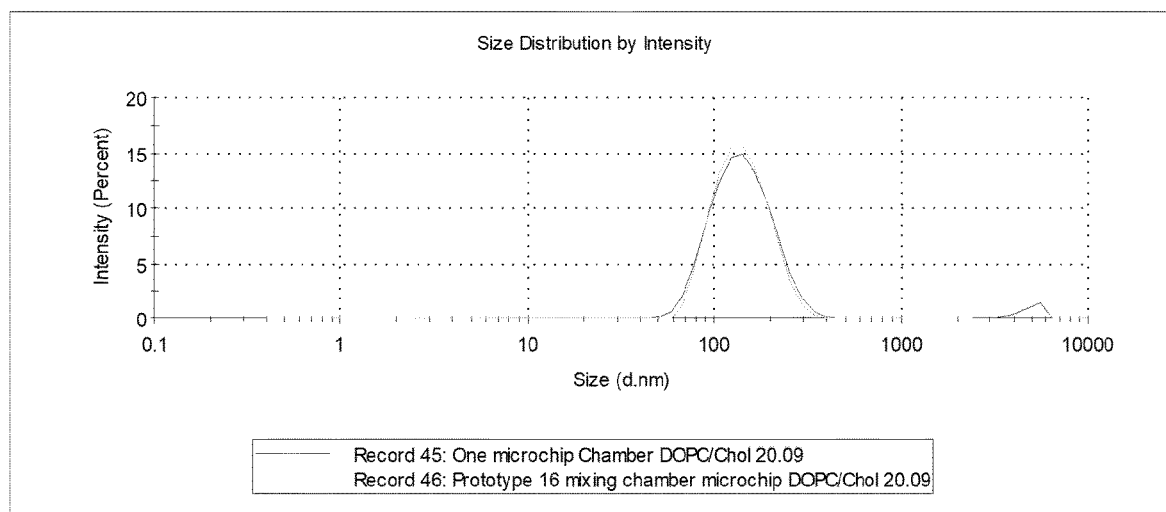
FIG. 35: Size distribution comparison between the 16 mixing chamber and single mixing chamber liposomes

Size measurements were calculated using Malvern ZS Nano series instruments (FIG. 35) and show the same trend for the pool of the 16-mixing chamber compared to the liposomes produced with the "one" mixing chamber. Sizes and polydispersity are also equivalent (Table 7).

The results show for the first time an equivalence for liposome production (DOPC-Cholesterol) between a prototype containing 16 mixing chambers (and the associated manifolds) suitable for use in commercial scale production with the one mixing chamber.

TABLE 7

DLS results of multichamber and single chamber liposomes

|  | Zav (nm) | PdI |
|---|---|---|
| Single mixing chamber | 141 | 0.22 |
| Pool of 16 mixing chambers | 143 | 0.23 |

Example 8: Adaptive Immune Responses Relative to Liposomes Produced by Thin Film Methods Method Adjuvant Preparation Three lots of liposomes were prepared using the single mixing chamber apparatus described previously. Organic phase comprising DOPC (130 mg/ml), cholesterol (32.5 mg/ml) and 3D-MPL (6.5 mg/ml) in 80/20 ethanol/IPA was mixed with aqueous phase containing QS-21 (1.625 mg/ml) in water for injection under conditions of a total flow rate of 16 ml/min and a flow rate ratio of 5 (1:4 organic:aqueous). The temperature was maintained at 20° C.

Solvent was removed by diafiltration using a Hydrosart 30 kDa membrane and six volumes of replacement buffer. Diafiltration time was approximately 40 minutes. Material was subsequently sterile filtered using a sterile filtration on 0.22 um PES membrane.

The resulting liposomal adjuvant concentrate can be diluted as necessary to provide the final adjuvant preparations.

Vaccination 6-8 week old-female C57B16 mice (6 mice per group, total 186 animals) were injected twice with a 14-day interval with gE antigen in a liposomal formulation with 3D-MPL and QS-21. A negative control group received gE with buffer alone over the same schedule.

The final vaccination mixture was prepared by dilution of adjuvant concentrate and mixing with gE as necessary. Five doses of adjuvant were evaluated (0.05, 0.1, 0.2, 0.4 and 1 ug of both 3D-MPL and QS-21 per animal per injection, corresponding to 1/1000, 1/500, 1/250, 1/125 and 1/50 of a typical 50 ug human dose (HD), respectively based on expected content of immunostimulant). Each animal received 5 ug of gE per injection. The injection volume was 20 ul. Three lots of microfluidic liposomal adjuvant were compared to three lots of liposomal adjuvant produced by thin film methods.

Due to space restrictions, the experiment was undertaken in two parts (i.e. 3 mice from each group of 6 received treatment in each part, with the results combined).

Spleen and sera were collected and analysed for T and B cell responses, respectively, 7 days post the second immunisation (day 21).

ICS and ELISA were undertaken using the methods provided in Example 5.

Results

Microfluidic Lot Characterisation

TABLE 8

DLS characterisation of microfluid lots

| Lot | After microfluidic mixing | | After Diafiltration and Sterilisation | | After Storage (4 deg C.) | | Time |
|---|---|---|---|---|---|---|---|
| | ZAV (nm) | Pdl | ZAV (nm) | Pdl | ZAV (nm) | Pdl | |
| 1 | 98 | 0.18 | 96 | 0.19 | 98 | 0.19 | 4.5 months |
| 2 | 100 | 0.21 | 100 | 0.22 | 99 | 0.21 | 4 months |
| 3 | 103 | 0.22 | 102 | 0.24 | 102 | 0.24 | 4 months |

TABLE 9

Microfluidic lot composition (after dilution of concentrate)

| Lot | DOPC (mg/ml) | Cholesterol (mg/ml) | QS21 (ug/ml) (Expected 100) | 3D-MPL (ug/ml) (Expected 100) | Residual alcohol (ug/500 ul dose) |
|---|---|---|---|---|---|
| 1 | 1.9 | 0.46 | 91 | 74 | 55 |
| 2 | 2 | 0.51 | 96 | 82 | 125 |
| 3 | 2 | 0.48 | 96 | 79 | 85 |

TABLE 10

Thin film lot characterisation

| Lot | DOPC (mg/ml) | Cholesterol (mg/ml) | QS21 (ug/ml) (Expected 100) | 3D-MPL (ug/ml) (Expected 100) | Residual alcohol (ug/500 ul dose) | Zav (nm) | Pdl |
|---|---|---|---|---|---|---|---|
| 1 | 2 | 0.49 | 99 | 84 | Not performed | 104 | 0.14 |
| 2 | 1.9 | 0.49 | 94 | 88 | Not performed | 108 | 0.14 |
| 3 | 2 | 0.48 | 101 | 84 | Not performed | 105 | 0.13 |

Figure 36:
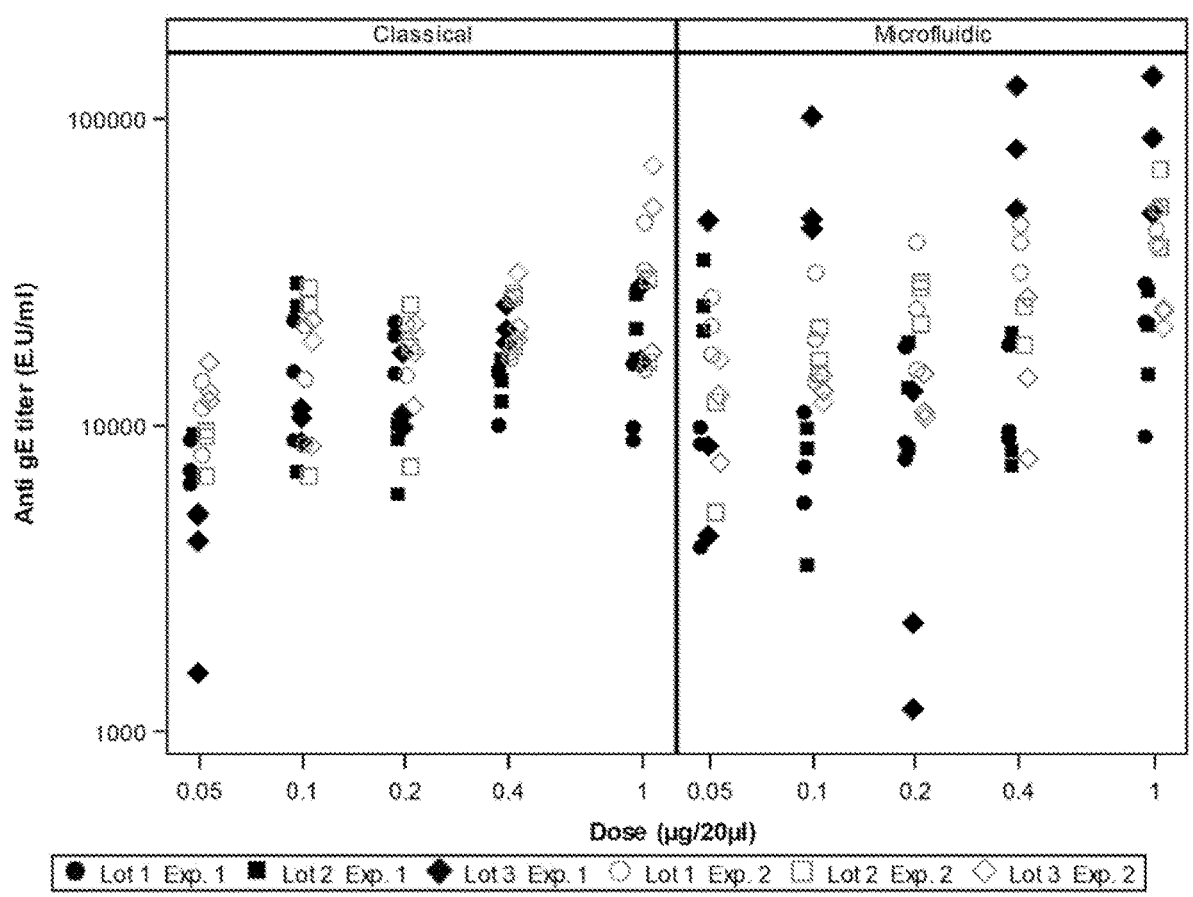
FIG. 36: gE-specific IgG titer comparison between microfluidic and thin film liposomal adjuvants
Figure 37:
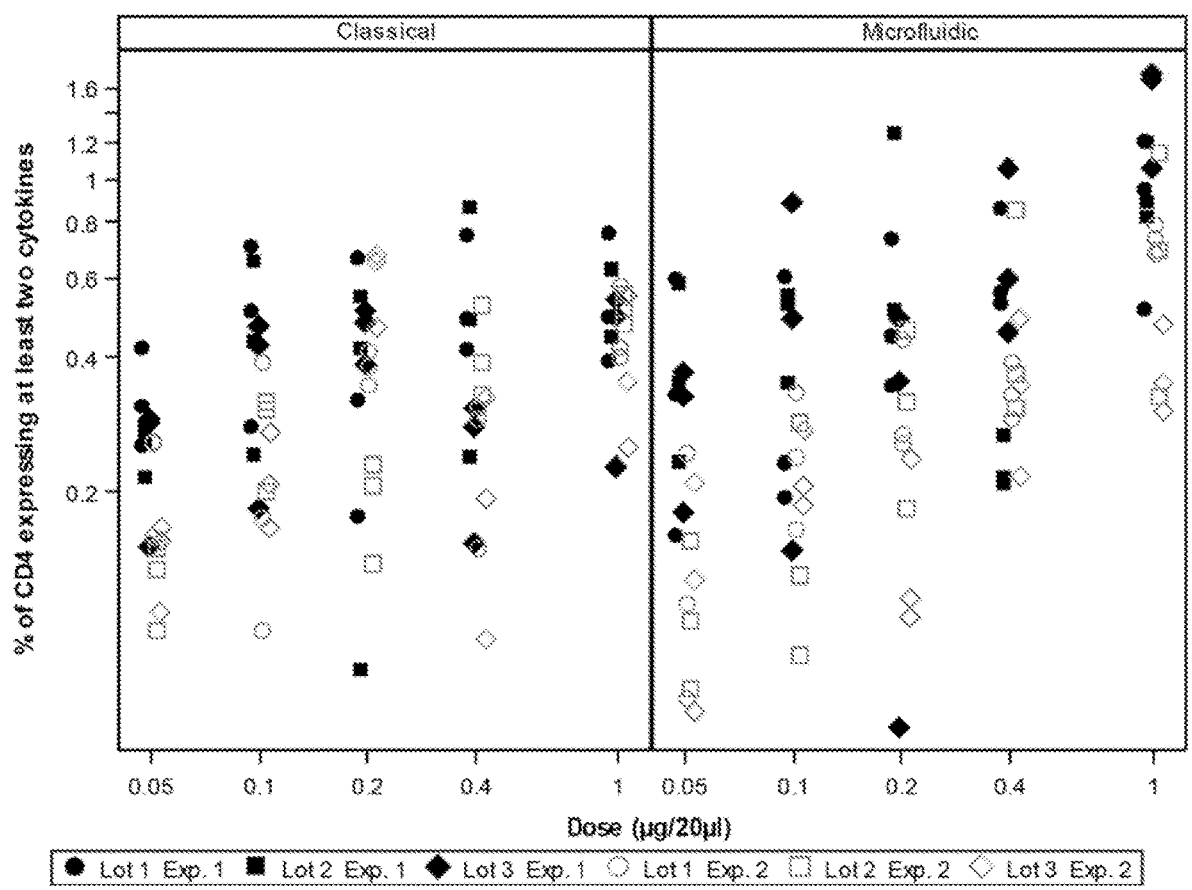
FIG. 37: gE-specific CD4+ T cells comparison between microfluidic and thin film liposomal adjuvants

ELISA results are shown in FIG. 36 and ICS results in FIG. 37.

Figure 38:
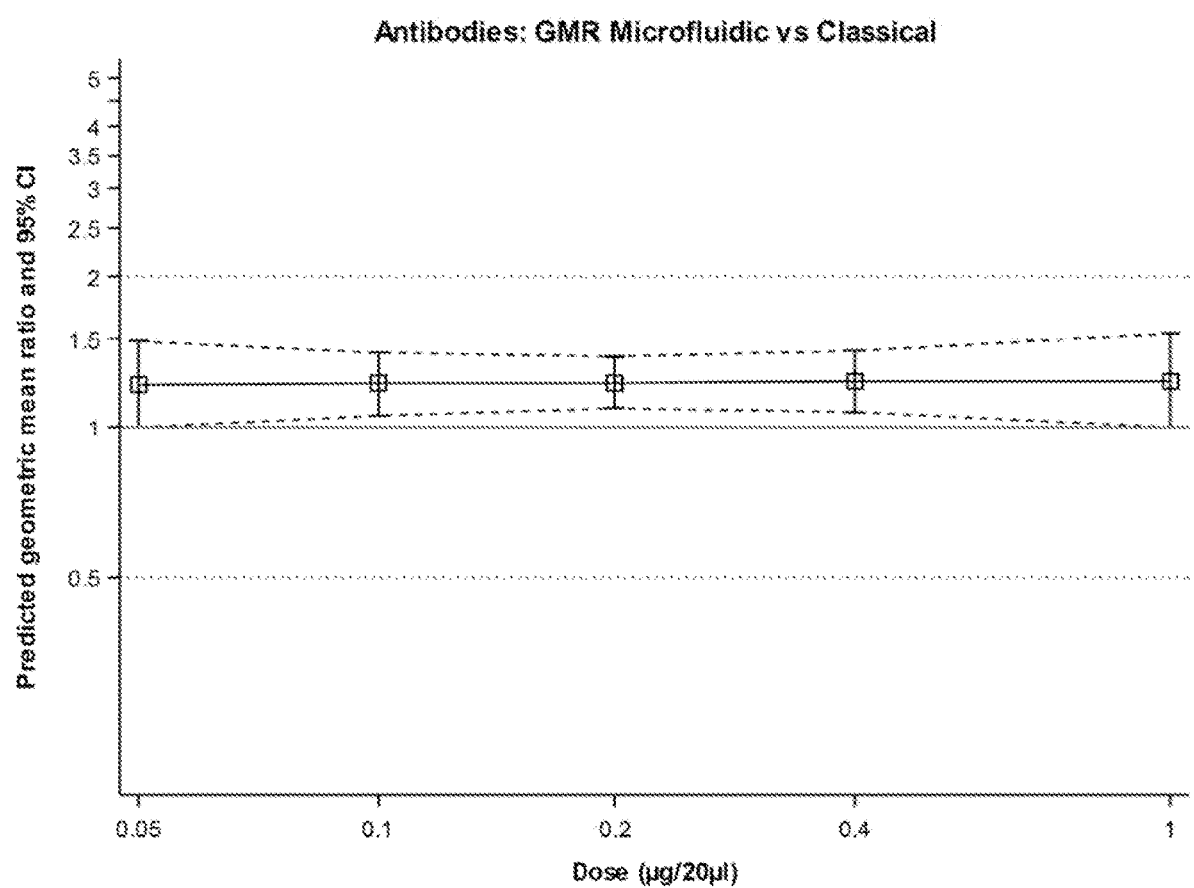
FIG. 38: gE-specific IgG titer GMR comparison between microfluidic and thin film liposomal adjuvants
Figure 39:
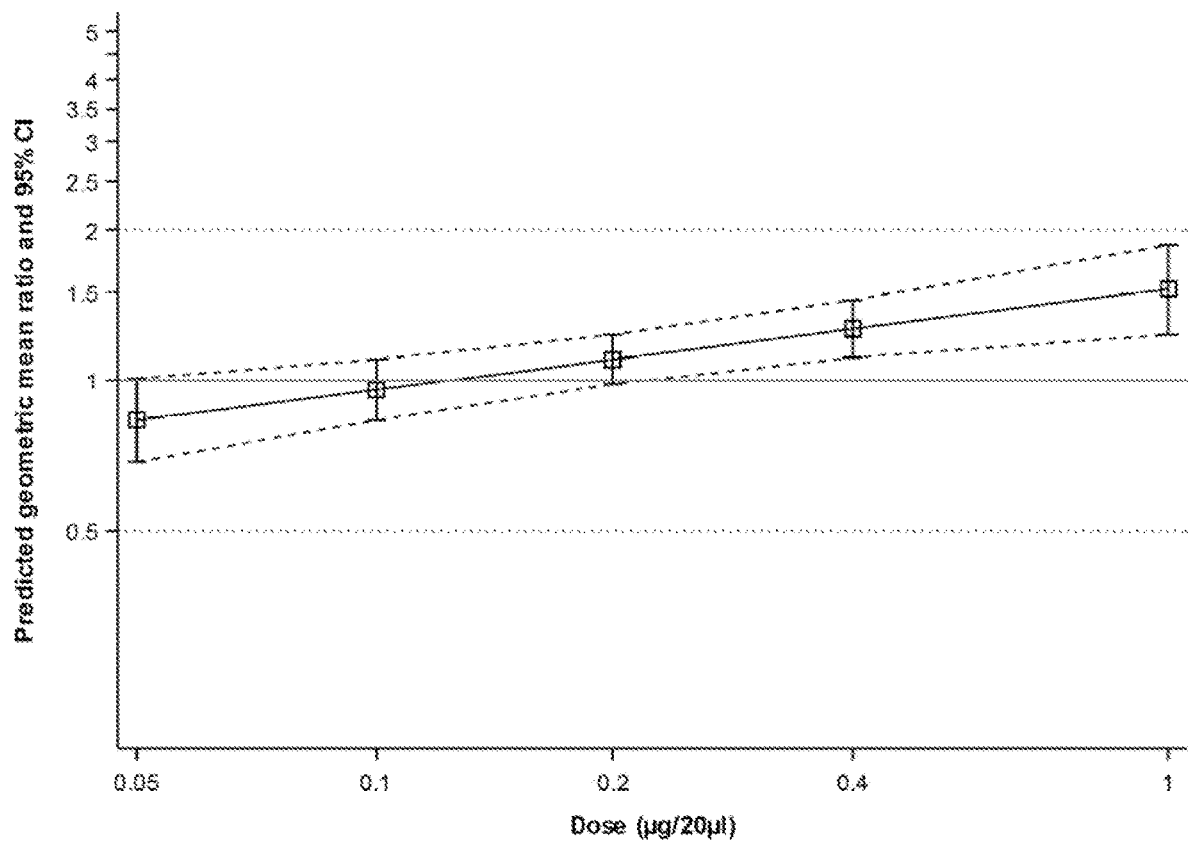
FIG. 39: gE-specific CD4+ T cells GMR comparison between microfluidic and thin film liposomal adjuvants

A model was used to compute and then retrieve the effect of the experiment part (Exp 1 vs Exp 2) and the lot (Lot 1, Lot 2 or Lot 3) from the data. A linear model was then fitted on these data separately for both processes. The associated predicted geometric means ratios between processes are presented in FIG. 38 and FIG. 39 (ELISA and ICS respectively).

Conclusions

Microfluidics-produced liposomes in conjunction with TLR4 agonist and saponin were capable of adjuvating the cellular and antibody responses to an exemplary antigen in a generally comparable manner to thin film produced liposomes.

Example 9: Adaptive Immune Responses Relative to Liposomes Produced by Thin Film Methods Following the successful scale up described in Example 7, the 16 channel microfluidic apparatus was used to prepare a batch of liposomal material including the saponin (QS21) and TLR4 (3D-MPL) immunostimulants.

Organic phase comprising DOPC (130 mg/ml), cholesterol (32.5 mg/ml) and 3D-MPL (6.5 mg/ml) in 80/20 ethanol/IPA was mixed with aqueous phase containing QS-21 (1.625 mg/ml) in water for injection under conditions of a total flow rate of 16 ml/min (per chamber) and a flow rate ratio of 5 (1:4 organic:aqueous). The temperature was maintained at 20° C.

An initial single chamber benchmark run was conducted using a single chamber (first 2 ml discarded).

Subsequently the system was operated with all 16 chambers in parallel and material from each chamber exit was individually collected (first 2 ml from each chamber discarded). A pool of the 16 chambers was prepared. A third run was performed the same single mixing chamber used for the benchmark conditions (not placed into the incubator), again the first 2 ml discarded.

Size measurements were undertaken by DLS after the microfluidic process (no solvent removal).

TABLE 11

DLS results of multichamber and single chamber liposomes

| | Zav (nm) | Pdl |
|---|---|---|
| Single mixing chamber benchmark | 105 | 0.21 |
| Pool of 16 mixing chambers | 103 | 0.20 |
| Single mixing chamber | 106 | 0.21 |

Figure 40:
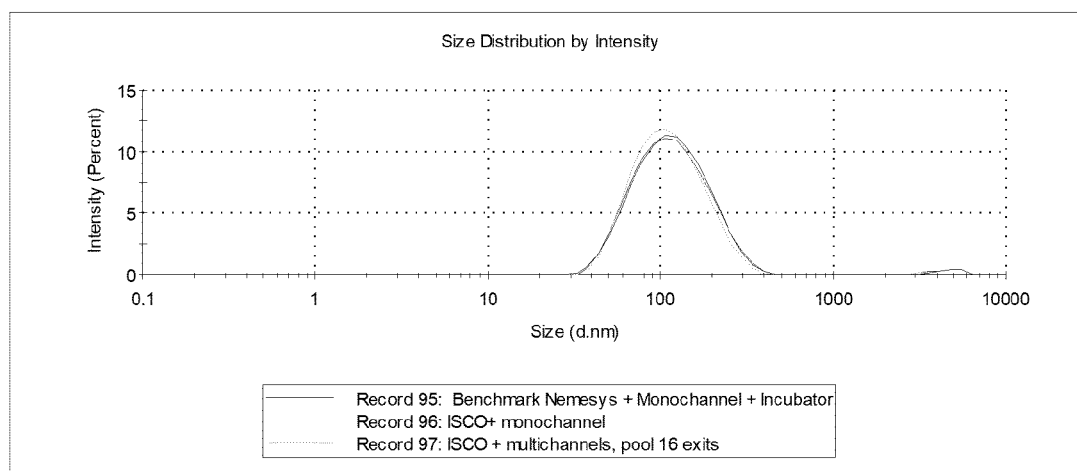
FIG. 40: Size distribution comparison between the 16 mixing chamber and single mixing chamber liposomes with saponin (QS21) and TLR4 agonist (3D-MPL)

The comparison of the sizes obtained on the three runs (FIG. 40) shows comparable profiles, confirming that the robust and scalable nature of the approaches set out in the present application.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The application of which this description and claims forms part may be used as a basis for priority in respect of any subsequent application. The claims of such subsequent application may be directed to any feature or combination of features described herein. Embodiments are envisaged as being independently, fully combinable with one another where appropriate to the circumstances to form further embodiments of the invention. They may take the form of product, composition, process, or use claims and may include, by way of example and without limitation, the claims which follow.

All publications, including but not limited to patents and patent applications, cited in this specification are herein incorporated by reference as if each individual publication were specifically and individually indicated to be incorporated by reference herein as though fully set forth.

BIBLIOGRAPHY

Arias M A et al. (2012) Glucopyranosyl Lipid Adjuvant (GLA), a Synthetic TLR4 Agonist, Promotes Potent Systemic and Mucosal Responses to Intranasal Immunization with HIVgp140. PLoS ONE 7(7): e41144. doi:10.1371/journal.pone.0041144

Black, S., E. De Gregorio, and R. Rappuoli. 2015. Developing vaccines for an aging population. *Science translational medicine.* 7:281ps288

Coler R N et al. (2011) Development and Characterization of Synthetic Glucopyranosyl Lipid Adjuvant System as a Vaccine Adjuvant. PLoS ONE 6(1): e16333. doi:10.1371/journal.pone.0016333

Dalsgaard et al. in 1974 ("Saponin adjuvants", Archiv. für die gesamte Virusforschung, Vol. 44, Springer Verlag, Berlin, p 243-254)

De Becker, G., V. Moulin, B. Pajak, C. Bruck, M. Francotte, C. Thiriart, J. Urbain, and M. Moser. 2000. The adjuvant monophosphoryl lipid A increases the function of antigen-presenting cells. *International immunology.* 12:807-815.

Dendouga, N., M. Fochesato, L. Lockman, S. Mossman, and S. L. Giannini. 2012. Cell-mediated immune responses to a varicella-zoster virus glycoprotein E vaccine using both a TLR agonist and QS-21 in mice. *Vaccine.* 30:3126-3135.

Didierlaurent A. M., Collignon C., Bourguignon P., Wouters S., Fierens K., Fochesato M., Dendouga N., Langlet C., Malissen B., Lambrecht B. N., Garcon N., Van Mechelen M., and S. Morel. 2014 Enhancement of Adaptive Immunity by the Human Vaccine Adjuvant AS01 Depends on Activated Dendritic Cells *Journal of Immunology* 193(4): 1920-1930.

Didierlaurent et al, 2017 Adjuvant system AS01: helping to overcome the challenges of modern vaccines *Expert Reviews of Vaccines* 16(1): 55-63

Dillon et al Infection and Immunity 1999 67(6): 2941-2950

Enhancement of Adaptive Immunity by the Human Vaccine Adjuvant AS01 Depends on Activated Dendritic Cells. *The Journal of Immunology.* 193

Garcon, N., and M. Van Mechelen. 2011. Recent clinical experience with vaccines using MPL- and QS-21-containing adjuvant systems. *Expert review of vaccines.* 10:471-486

Fochesato, M., Dendouga N. and Boxus M. 2016 *Hum Vaccin Immunother* 12(8):2092-2095

Haumont M., Jacquet A., Massaer M., Deleersnyder V., Mazzu P., Bollen A. and Jacobs P 1996 Purification, characterization and immunogenicity of recombinant varicella-zoster virus glycoprotein gE secreted by Chinese hamster ovary cells *Virus Res* 1996 40(2):199-204

Helminen M E, et al. (1993) Infect. Immun. 61:2003-2010

Hood, R. R.; DeVoe, D. L. 2015 High Throughput Continuous Flow Production of Nanoscale Liposomes by Microfluidic Vertical Flow Focusing. *Small Journal.* 11, No. 43, 5790-5799

Ismaili, J., J. Rennesson, E. Aksoy, J. Vekemans, B. Vincart, Z. Amraoui, F. Van Laethem, M. Goldman, and P. M. Dubois. 2002. Monophosphoryl lipid A activates both human dendritic cells and T cells. *Journal of immunology.* 168:926-932.

Kensil, C. R., U. Patel, M. Lennick, and D. Marciani. 1991. Separation and characterization of saponins with adjuvant activity from *Quillaja saponaria* Molina cortex. *Journal of immunology.* 146:431-437.

Kensil, C. R., and R. Kammer. 1998. QS-21: a water-soluble triterpene glycoside adjuvant. *Expert opinion on investigational drugs.* 7:1475-1482.

Kim Y T et al 2012 Mass production and size control of lipid-polymer hybrid nanoparticles through controlled microvortices. *Nano Letters* 12(7):3587-3591

Lambrecht, B. N., M. Kool, M. A. Willart, and H. Hammad. 2009. Mechanism of action of clinically approved adjuvants. *Current opinion in immunology.* 21:23-29.

Leroux-Roels I. et al. J. Infect. Dis. 2012, 206: 1280-1290

Li, H., S. B. Willingham, J. P. Ting, and F. Re. 2008. Cutting edge: inflammasome activation by alum and alum's adjuvant effect are mediated by NLRP3. *Journal of immunology.* 181:17-21.

Livingston, P. O., S. Adluri, F. Helling, T. J. Yao, C. R. Kensil, M. J. Newman, and D. Marciani. 1994. Phase 1 trial of immunological adjuvant QS-21 with a GM2 ganglioside-keyhole limpet haemocyanin conjugate vaccine in patients with malignant melanoma. *Vaccine.* 12:1275-1280.

Ragupathi, G., J. R. Gardner, P. O. Livingston, and D. Y. Gin. 2011. Natural and synthetic saponin adjuvant QS-21 for vaccines against cancer. *Expert review of vaccines.* 10:463-470

Martin, M., S. M. Michalek, and J. Katz. 2003. Role of innate immune factors in the adjuvant activity of monophosphoryl lipid A. *Infection and immunity.* 71:2498-2507.

Marty-Roix, R. et al. Identification of QS-21 as an Inflammasome-activating Molecular Component of Saponin Adjuvants. *J. Biol. Chem.* 291, 1123-36 (2016)

Mata-Haro, V., C. Cekic, M. Martin, P. M. Chilton, C. R. Casella, and T. C. Mitchell. 2007. The vaccine adjuvant monophosphoryl lipid A as a TRIF-biased agonist of TLR4. *Science.* 316:1628-1632.

McLellan et al., Science, Vol. 340: 1113-1117.

McLellan et al., Science, Vol 342: 592-598

Newman, M. J., J. Y. Wu, B. H. Gardner, K. J. Munroe, D. Leombruno, J. Recchia, C. R. Kensil, and R. T. Coughlin. 1992. Saponin adjuvant induction of ovalbumin-specific CD8+ cytotoxic T lymphocyte responses. *Journal of immunology.* 148:2357-2362.

Rigter et al., PLOS One, Vol. 8: e71072

Skeiky et al Infection and Immunity 1999 67(8): 3998-4007

Skeiky et al J. Immunol. 2004 172:7618-7628

Soltysik, S., J. Y. Wu, J. Recchia, D. A. Wheeler, M. J. Newman, R. T. Coughlin, and C. R. Kensil. 1995. Structure/function studies of QS-21 adjuvant: assessment of triterpene aldehyde and glucuronic acid roles in adjuvant function. *Vaccine.* 13:1403-1410.

Vafai A., Antibody binding sites on truncated forms of varicella-zoster virus gpl(gE) glycoprotein, *Vaccine* 1994 12:1265-9

The invention claimed is:

1. A solution comprising a solvent and 100-170 mg/ml phosphatidylcholine lipid, wherein the solvent comprises 70-90% v/v ethanol and 10-30% v/v isopropyl alcohol.

2. The solution according to claim 1, comprising 100-160 mg/ml phosphatidylcholine.

3. The solution according to claim 2, comprising 120-140 mg/ml phosphatidylcholine.

4. The solution according to claim 1, further comprising 20-50 mg/ml sterol.

5. The solution according to claim 4, comprising 30-40 mg/ml of sterol.

6. The solution according to claim 4, wherein the ratio of phosphatidylcholine to sterol is 3:1 to 5:1.

7. The solution according to claim 4, wherein the sterol is cholesterol.

8. The solution according to claim 1, further comprising a Toll-like receptor 4 (TLR4) agonist.

9. The solution according to claim 8, wherein the TLR4 agonist is a lipopolysaccharide.

10. The solution according to claim 9, wherein the lipopolysaccharide is 3-de-O-acylated monophosphoryl lipid A (3D-MPL).

11. The solution according to claim 8, wherein the TLR4 agonist is present at a concentration of 4-12 mg/ml.

12. The solution according to claim 1, wherein the solvent comprises 75-85% v/v ethanol.

13. The solution according to claim 1, wherein the solvent comprises 15-25% v/v isopropanol.

14. The solution according to claim 1, wherein the solvent comprises 78-82% v/v ethanol, and 18-22% v/v isopropyl alcohol.

15. The solution according to claim 1, wherein the phosphatidylcholine lipid contains saturated unbranched acyl chains having 12-20 carbon atoms.

16. The solution according to claim 15, wherein the lipid is dioleoyl phosphatidylcholine (DOPC).

17. A solution which consists essentially of a solvent and 100-160 mg/ml DOPC, 30-40 mg/ml cholesterol, 4-10 mg/ml TLR4 agonist, and wherein the solvent comprises 70-90% v/v ethanol and 10-30% v/v isopropyl alcohol.

18. The solution according to claim 17 wherein the TLR4 agonist is a lipopolysaccharide.

19. The solution according to claim 18, wherein the lipopolysaccharide is 3D-MPL.

* * * * *